United States Patent [19]
Doherty et al.

[11] Patent Number: 5,229,381
[45] Date of Patent: Jul. 20, 1993

[54] SUBSTITUTED AZETIDINONES AS ANTI-INFLAMMATORY AND ANTIDEGENERATIVE AGENTS

[75] Inventors: James B. Doherty, New Milford; Conrad P. Dorn, Plainfield; Paul E. Finke, Milltown; William K. Hagmann, Westfield; Malcolm MacCoss, Freehold; Shrenik K. Shah, Metuchen, all of N.J.

[73] Assignee: Merck & Co., Inc., Rahway, N.J.

[21] Appl. No.: 761,191

[22] Filed: Sep. 20, 1991

Related U.S. Application Data

[63] Continuation-in-part of Ser. No. 735,696, Jul. 25, 1991, abandoned, and a continuation-in-part of Ser. No. 719,653, Jun. 21, 1991, abandoned, said Ser. No. 735,696, Continuation of Ser. No. 597,617, said Ser. No. 719,653, Continuation of Ser. No. 388,771, is a continuation-in-part of Ser. No. 179,688, Apr. 11, 1988, abandoned, which is a continuation-in-part of Ser. No. 89,797, Aug. 27, 1987, abandoned, which is a continuation of Ser. No. 842,834, Mar. 27, 1986, abandoned, which is a continuation-in-part of Ser. No. 721,811, Apr. 10, 1985, Pat. No. 4,680,391, which is a continuation-in-part of Ser. No. 557,030, Dec. 11, 1983, abandoned.

[51] Int. Cl.[5] .................. A61K 31/395; C07D 205/08; C07D 205/09; C07D 405/12

[52] U.S. Cl. .................... 514/210; 540/355; 540/357; 540/359; 540/360; 540/362; 540/363; 540/364

[58] Field of Search ............... 514/210; 540/360

[56] References Cited

U.S. PATENT DOCUMENTS

| | | |
|---|---|---|
| 4,064,120 | 12/1977 | Krapcho et al. ............ 540/200 |
| 4,115,382 | 9/1978 | Krapcho et al. ............ 540/200 |
| 4,166,907 | 9/1979 | Krapcho et al. ............ 540/200 |
| 4,174,317 | 11/1979 | Krapcho ............ 540/200 |
| 4,260,743 | 4/1981 | Bose ............ 424/304 |
| 4,493,839 | 1/1985 | Doherty ............ 424/263 |
| 4,510,086 | 4/1985 | Ross et al. ............ 540/360 |
| 4,534,896 | 8/1985 | Treuner et al. ............ 514/210 |
| 4,559,335 | 12/1985 | Zahler ............ 514/210 |
| 4,576,749 | 3/1986 | Zahler et al. ............ 514/210 |
| 4,680,391 | 7/1987 | Firestone et al. ............ 540/357 |

FOREIGN PATENT DOCUMENTS

| | | |
|---|---|---|
| 295547 | 1/1972 | Austria . |
| 375640 | 8/1984 | Austria . |
| 0023097 | 1/1981 | European Pat. Off. . |
| 0042026 | 12/1981 | European Pat. Off. . |
| 0076621 | 4/1983 | European Pat. Off. . |
| 0199630 | 10/1986 | European Pat. Off. . |
| 0337549 | 10/1989 | European Pat. Off. . |
| 1945542 | 3/1971 | Fed. Rep. of Germany . |
| 2046822 | 3/1972 | Fed. Rep. of Germany . |
| 2046823 | 3/1972 | Fed. Rep. of Germany . |
| 2748827 | 5/1978 | Fed. Rep. of Germany . |
| 2824554 | 12/1978 | Fed. Rep. of Germany . |
| 2842466 | 4/1979 | Fed. Rep. of Germany . |
| 2911589 | 9/1979 | Fed. Rep. of Germany . |
| 3007298 | 9/1981 | Fed. Rep. of Germany . |
| 1192952 | 5/1970 | United Kingdom . |
| 1604752 | 12/1981 | United Kingdom . |
| 2093839 | 9/1982 | United Kingdom . |

OTHER PUBLICATIONS

Yoshifugi Chem. Abstracts, vol. 105, Abs. 97895t (1986).

Peitsch, Hartmut, Tetrahedron Letters No. 45 pp. 4053-4056 (1976).

Tanaka, et al Heterocycles vol. 24, No. 9, pp. 2539-2543 (1986).

*Primary Examiner*—Mark L. Bell
*Attorney, Agent, or Firm*—Curtis C. Panzer; Raymond M. Speer

[57] ABSTRACT

New substituted azetidinones of the general formula (A') which have been found to be potent elastase inhibitors and thereby useful anti-inflammatory and antidegenerative agents are described.

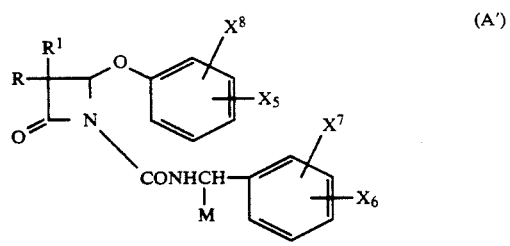

17 Claims, No Drawings

SUBSTITUTED AZETIDINONES AS ANTI-INFLAMMATORY AND ANTIDEGENERATIVE AGENTS

This application is a continuation-in-part of U.S. Ser. No. 735,696, filed Jul. 25, 1991 and U.S. Ser. No. 719,653, filed Jun. 21, 1991 (now abandoned). U.S. Ser. No. 735,696 is a continuation of U.S. Ser. No. 597,617 filed Oct. 15, 1990 now abandoned. U.S. Ser. No. 719,653 is a continuation of ID U.S. Ser. No. 388,771 filed Aug. 21, 1989, now abandoned; which is a CIP of U.S. Ser. No. 179,688 filed Apr. 11, 1988, now abandoned; which is a CIP of U.S. Ser. No. 089,797 filed Aug. 27, 1987, now abandoned; which is a continuation of U.S. Ser. No. 842,834 filed Mar. 27, 1986, now abandoned; which is a CIP of U.S. Ser. No. 721,811 filed Apr. 10, 1985, which issued as U.S. Pat. No. 4,680,391; which is a CIP of U.S. Ser. No. 557,030 filed Dec. 11, 1983, now abandoned.

BACKGROUND OF THE INVENTION

We have found that a group of new substituted azetidinones are potent elastase inhibitors and therefore are useful anti-inflammatory and antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, glomercular nephrihs, myocardiol infection/reperfusion injury osteoarthritis, spondylitis, lupus, psoriasis, atherosclerosis, sepsis, septicemia, shock, periodontitis, cystic fibrosis, myocardial infarction, reperfusion injury, meningitis, glomerulonephritis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and (3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am.* July 1974, pp. 74-88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of*

*Proteinases*, H. Holzer and H. Tschesche, eds. Springer-Verlag, Berlin, Heidelberg, N.Y., pp. 196-206, 1979.

BRIEF DESCRIPTION OF THE INVENTION

The instantly claimed invention is directed to specifically substituted azetidinones in which the N-substiuent is a phenylalkylaminocarbonyl group. This invention is also directed to pharmaceutical compositions and methods of using these specifically substituted azetidinones.

DETAILED DESCRIPTION OF THE INVENTION

This invention relates to potent elastase inhibitors of Formula (I), Formula A and Formula A' which are useful in the prevention, control and treatment of inflammatory and degenerative conditions especially arthritis and emphysema.

A large number of the azetidinone derivatives of Formula (I), Formula A and Formula A' are known antibiotics which have been described in patents and various publications.

A formula of the substituted azetidinones which are found to exhibit anti-inflammatory and antidegenerative activities by the present invention are represented as follows:

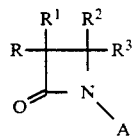

wherein: R can be at the α or the β-stereochemical configuration and is hydrogen, straight or branched loweralkyl, especially $C_{1-6}$alkyl, such as methyl, ethyl, n- or i-propyl, butyl, pentyl or hexyl; or loweralkyl substituted with a radical $R^4$ as defined below; or halo such as fluoro, chloro or bromo; $R^1$ can be at the α- or the β-stereochemical configuration and is (a) OB or —S(O)$_n$B wherein B is as defined below and n is 0, 1 or 2;
(b) Straight or branched loweralkenyl especially $C_{2-8}$alkenyl such as vinyl, allyl, —CH$_2$CH=C(CH$_3$)$_2$, and —CH$_2$CH$_2$CH=CH$_2$;
(c) loweralkyl as defined above;
(d) acylamino e.g.

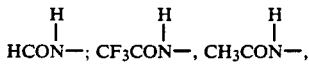
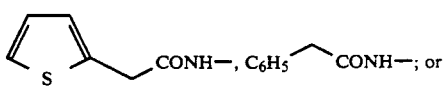

(e) amino;
(f) Straight or branched loweralkynyl group especially $C_{3-6}$alkynyl such as —C≡CH, —CH$_2$—C≡CH and —CH$_2$CH$_2$—C≡CCH$_3$;
(g) An aryl group having 6-14 carbon atoms as described below such as phenyl of formula

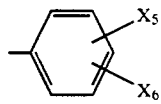

wherein $X_5$ and $X_6$ independently are:
1) Q, where Q is H, loweralkyl, haloloweralkyl, phenyl or substituted phenyl or naphthyl;
2) halo;
3) loweralkenyl;
4) loweralkynyl;
5) —SQ;
6) —OQ;
7) —CHQCOQ$^1$, where Q$^1$ is defined as Q and Q$^1$ can be the same as or different from Q;
8) —CHQCOOQ$^1$ such as CH$_2$COOH;
9) —CH$_2$SQ;
10) —CHQSQ$^1$;
11) —CH$_2$OQ or —CHQOQ$^1$ especially —CH$_2$OH and —CH$_2$OCH$_3$;
12) —COQ for example, —COCH$_3$ and —(CO)H;
13) —COOQ especially —COOH and COOt—Bu;
14) —OCOQ such as —OCOCH$_3$;
15) —NQQ$^1$;
16) —NQCOQ$^1$ especially —NHCOCH$_3$;
17) —CH$_2$NH$_2$ or —CH$_2$N$^+$(CH$_3$)$_3$I$^-$;
18) —CH$_2$OCOCH$_3$;
19) —NQSO$_2$Q$^1$;
20) —SO$_2$NQQ$^1$;
21) —SOQ;
22) —SO$_2$Q;
23) —SO$_3$Q;
24) —CN;
25) —NO$_2$;
26) —CONQQ$^1$;
27) —NO;
28) —CSQ;
29) —CSNQQ$^1$;
30) —CF$_2$SQ;
31) —CF$_2$OQ;
32) —NQCONHQ$^1$ or NQCONQ$^1$Q$^2$ where Q$^2$ is defined as Q$^1$ and Q$^2$ can be the same as or different from Q$^1$;
33) —CH$_2$Y wherein Y represents —CH(NHAC)-COO$^-$, CH(N$^+$H$_3$) COO$^-$, CH$_2$COOH, COOH, —N(CH$_3$)$_2$, OH, CH$_2$N(CH$_3$)$_2$, or CH$_2$OH;
34) —CH$_2$(C$_{1-6}$ alkyl);
35) —NH(CO)CH$_2$CH$_2$COOH;
36)

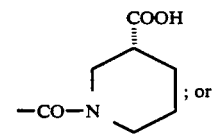

37) —CO—NH—SO$_2$phenyl or substituted phenyl such as p-chlorophenyl;
(h) heteroaryl such as unsubstituted or substituted furyl, thienyl, thiazolyl, pyrryl, pyrimidinyl, pyridyl, oxazolyl, tetrazolyl or imidazolyl wherein the substituents are as those described for substituted phenyls;
(i) aralkyl especially phenyl $C_{1-6}$alkyl such as benzyl of formula

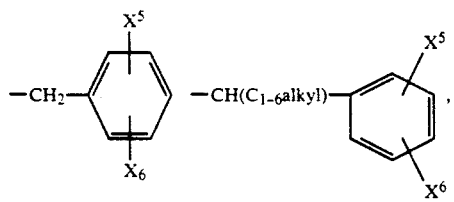

or phenethyl;

(j) halo such as F, Cl, Br or I;

(k) $N_3$;

(l) hydrogen;

(m) R and $R^1$ may join together and form a cycloalkyl such as a $C_{1-6}$cycloalkyl, e.g., cyclopentane, =C(B)(B$_1$) or =O (oxo) wherein B and $B_1$ independently are as defined below;

(n) —CH$_2$OC$_{1-6}$ alkyl especially —CH$_2$OCH$_3$ and —CH$_2$OC$_2$H$_5$;

(o) —CH$_2$CH$_2$OC$_{1-6}$alkyl especially —CH$_2$CH$_2$OC$_2$H$_5$;

$R^2$ and $R^3$ can be at the α or the β-position and independently are (a) B as defined below;

(b) —CONBB$_1$ wherein B and $B_1$ independently represent (1) H;

(2) straight or branched alkyl having from 1 to 20 carbon atoms, preferably $C_{1-6}$alkyl such as methyl, ethyl, isopropyl, t-butyl, pentyl or hexyl;

(3) aryl having from 6 to 14 carbon atoms such as phenyl or substituted phenyl of formula

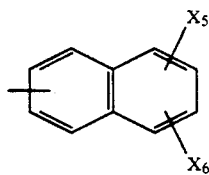

naphthyl or substituted naphthyl of formula

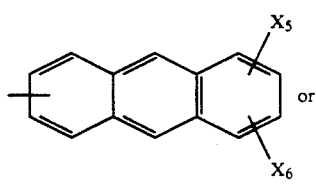

or anthracyl or substituted anthracyl of formula

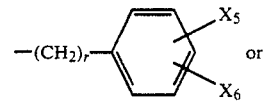

(4) cycloalkyl having from 3 to 8 carbon atoms especially cyclopropyl, cyclopentyl or cyclohexyl;

(5) straight or branched alkenyl having from 2 to 20 carbon atoms, for example, allyl;

(6) straight or branched alkynyl having from 2 to 20 carbon atoms, for example, =C≡CH;

(7) aralkyl, alkaryl, aralkenyl, aralkynyl, alkenylaryl or alkynylaryl wherein alkyl, aryl, alkenyl and alkynyl are as previously defined for example, $C_{1-6}$alkylphenyl of formula

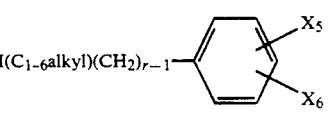

wherein r is 1 to 6, $C_{1-6}$alkyl naphthyl of formula

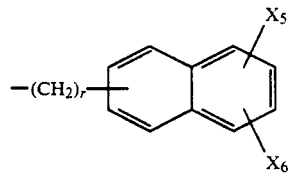

or

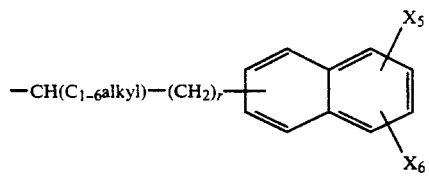

(8) heteroaryl comprising monoheteroaryl, di- or polyheteroaryl, or fused heteroaryl containing from 1 to 3 of any one or more of the heteroatoms N, S or O in each heteroaryl ring thereof, for example, pyridyl, pyrryl, such as

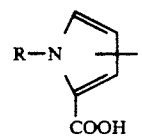

thienyl, isothiazolyl, imidazolyl such as

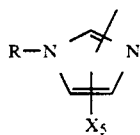

tetrazolyl such as

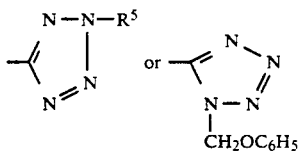

pyrazinyl, pyrimidyl, quinolyl, isoquinolyl, tetrahydroisoquinolyl such as

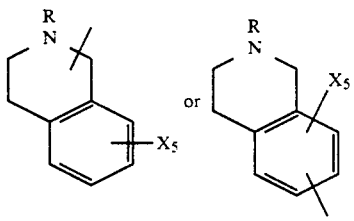

benzothienyl, benzofuryl such as

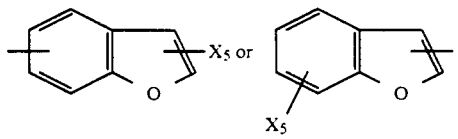

pyrazolyl, indolyl, purinyl, carbazolyl, isoxazolyl and the like;
(9) heteroarylalkyl such as 2-pyridylmethyl, 2-thienylmethyl and 3-isothiazolylethyl; or
(10) heterocycloalkyl e.g., 1,3-dioxacyclohex-4-yl, piperidino,

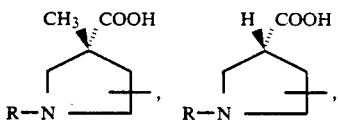

morpholino, oxacyclopropyl, pyrrolidino, benzothiazolino, imidazolidino, pyrazolidino, and piperazino;
(11) heterocycloalkenyl such as pyrrolino, 2-imidazolino, 3-pyrazolino or isoindolino;
(12) B and $B_1$ joined together and form a heterocyclic ring containing at least one N-atom and optionally 1 to 3 of the heteroatoms, N, S, or O, e.g.,

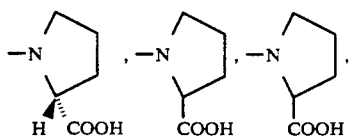

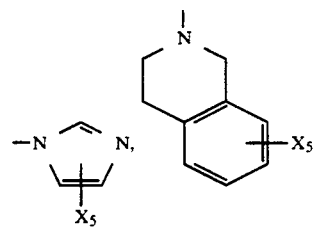

the above groups (1)–(12) can be unsubstituted or can be substituted by one or more radical $R^4$ selected from the group consisting of loweralkyl, hydroxy, aryloxy (OAr), alkoxy, halo, nitro, loweralkylthio, arylthio, mercapto, amino, monoalkyl or dialkyl substituted amino, cyano, carboxy, loweralkanoyl, Ar(C=O), aminosulfonyl, aminosulfenyl, aminosulfinyl, carbamoyl, carbamoyloxy, —S(O)$_n$R$^5$, SO$_3$R$^5$, —P(O)$_q$R$^5$ (where q is 1 or 2 and R$^5$ is H, C$_{1-6}$ alkyl, aralkyl or aryl as previously defined), azido, carboxamido or N-substituted carboxamido;
(c) —S(O)$_n$B;
(d) —S(O)$_n$NBB$_1$;
(e) —N(B)S(O)$_n$B$_1$;
(f) —P(O)$_q$BB$_1$;
(g) —C(O)B especially acetyl, benzoyl, e.g., p-chlorobenzoyl, p-methylbenzoyl and p-aminosulfonylbenzoyl;
(h) —OB especially —OC$_{1-6}$alkyl, phenoxy or substituted phenoxy of formula

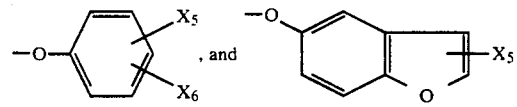

, and (i) —COOB, —OC(O)OB or OC(O)NBB$_1$;
(j) —O—C(O)—B especially C$_{1-6}$alkanoyloxy such as acetyloxy;
(k) cyano;
(l) —S—C(O)—B especially C$_{1-6}$alkanoylthio such as acetylthio; or
(m) $R^2$ and $R^3$ may join and form =C(B$_1$)(B), a C$_{1-6}$cycloalkyl for example, cyclopentyl, and =O(OXO);
A is
(a) —O—C(O)—B;
(b) —S(O)$_n$B;
(c) —S(O)$_n$NBB$_1$;
(d) —C(O)B;
(e) SO$_3$—M+ wherein M represents (a) an alkali anion such as Na+, K+; or (b) a quaternary ammonium group of formula N+(R$^5$)$_4$, for example, (n-Bu)$_4$N+;
(f) substituted or unsubstituted phosphoryl or phosphonyl such as —P(O)$_3$(R$^5$)$_2$ or —P(O)$_4$R$^5$;
(g) —C(O)NBB$_1$ especially —CON(CH$_3$) phenyl, —CON(C$_2$H$_5$)B$_1$ and —CONHB$_1$, wherein B$_1$ is
(1)—(CH$_2$)$_r$ Ph, or CH(C$_{1-6}$alkyl)(CH$_2$)$_{r-1}$Ph, e.g., —CH(C$_2$H$_5$)—Ph, —CH(C$_3$H$_7$)—Ph, —CH—(allyl)—Ph, —CH(C$_2$H$_5$)CH$_2$Ph, or —CH(CH$_3$)—Ph wherein Ph represents phenyl or substituted phenyl as previously defined, for examples, 4-methyl-phenyl, 4-methoxyphenyl, 4-ethoxyphenyl, 4-N,N-dimethylamino-phenyl, 4-benzyloxy-phenyl, 4- phenyl-phenyl, 3,4-methylenedioxyphenyl, and 3,4-dimethyl-phenyl;

(2) —(CH$_2$)$_r$(Naph) especially —CH$_2$(Naph) or —CH(C$_2$H$_5$)(Naph) wherein (Naph) is α or β-naphthyl or substituted naphthyl as previously defined;

(3) —(CH$_2$)$_r$(Ar) or CH(C$_{1-6}$alkyl) (CH$_2$)r—1(Ar) wherein Ar is as defined above especially —CH$_2$CH$_2$Ar or —CH$_2$Ar wherein Ar represents heteroaryl especially thienyl, furyl, substituted pyridyl, thienyl, 2-benzofuranyl, or benzofuranyl as well as substituted pyridyl, benzamidazole and other thienyls and furyls;

(4) —(CH$_2$)$_r$OPh especially —CH$_2$CH$_2$CH$_2$OPh;

(5) —(CH$_2$)$_r$CH(OH)Ph;

(6) —(CH$_2$)$_r$(CO)Ph;

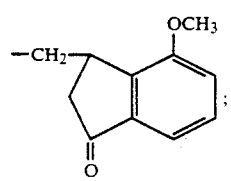 (7)

 (8)

—CH$_2$—Ph(p-CO—NH—SO$_2$—Ph(P—Cl)); (9)

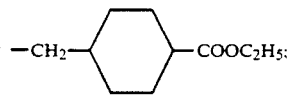 (10)

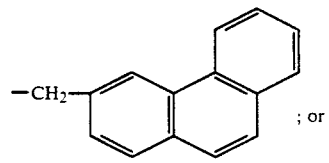 ; or (11)

(12) —CH(CH$_3$)—Ph(p-cyclohexyl);

(h) —C(O)OB expecially C$_{1-6}$ alkoxycarbonyl, e.g., methoxycarbonyl, and -ethoxycarbonyl or COOCH$_2$-Ph(p-COOC$_2$H$_5$);

(i) halo C$_{1-6}$alkyl such as trifluoromethyl;

(j) —OB especially —O—CH$_2$—(phenyl or substituted phenyl as previously defined), for example, —OCH$_2$C$_6$H$_5$; —OCH$_2$—C$_6$H$_4$—OCH$_3$; or OCH$_2$C$_6$H$_4$NO$_2$;

(k) silyl such as —Si(CH$_3$)$_2$(t—Bu);

(l) B especially H, C$_{1-6}$ alkyl, CH$_2$OH, —CH$_2$O(-CO)CH$_3$, phenyl or substituted phenyl, —CHR$^5$L where R$^5$ is as previously defined and L is a good leaving group comprising OAc, SAc, halogen, OR$^5$, SR$^5$, SOR$^5$, SO$_2$R$^5$, OTs, OCOCF$_3$, and mesyl wherein Ac is acetyl; and Ts is tosyl; or

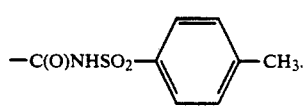 (m)

In one embodiment the instant invention is directed to the compounds of the Formula (A')

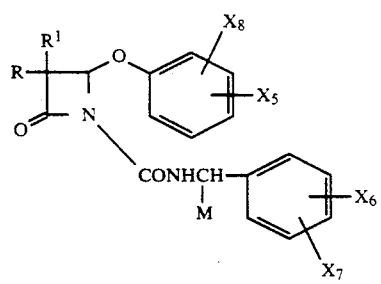 (A')

and pharmaceutically acceptable salts thereof wherein:

R is C$_{1-6}$ alkyl;

R$^1$ is C$_{1-6}$ alkyl or C$_{1-6}$ alkoxy-C$_{1-6}$ alkyl;

M is
(1) hydrogen,
(2) C$_{1-6}$ alkyl,
(3) hydroxy C$_{1-6}$ alkyl,
(4) halo C$_{1-6}$ alkyl,
(5) C$_{2-6}$ alkenyl, or
(6) C$_{1-6}$ alkoxy-C$_{1-6}$ alkyl;

X$_5$ is
(1) hydrogen,
(2) C$_{1-6}$ alkyl,
(3) halo-C$_{1-6}$ alkyl,
(4) C$_{2-6}$ alkenyl,
(5) C$_{2-6}$ alkynyl,
(6) carboxy,
(7) carboxy-C$_{1-6}$ alkyl,
(8) carboxy-C$_{1-6}$ alkylcarbonyl,
(9) carboxy-C$_{1-6}$ alkylcarbonylamino,
(10) carboxy-C$_{2-6}$ alkenyl,
(11) hydroxy-C$_{1-6}$ alkyl,
(12) C$_{1-6}$ alkylcarbonyl,
(13) C$_{1-6}$ alkylcarbonylamino, or
(14) hydroxymethylcarbonyl C$_{1-6}$ alkyl; and X$_6$ and X$_7$ are each independently
(1) hydrogen,
(2) C$_{1-6}$ alkyl,
(3) halo,
(4) carboxy,
(5) C$_{1-6}$ alkoxy,
(6) phenyl,
(7) C$_{1-6}$ alkylcarbonyl,
(8) di-(C$_{1-6}$alkyl)amino,
(9) phenoxy, or X$_6$ and X$_7$ are joined together to form a ring selected from furan, thiophene, and dioxacyclopentane; and X$_8$ is
(a) hydrogen,
(b) C$_{1-6}$ alkyl,
(c) halo,
(d) C$_{1-6}$ alkoxy, or
(e) hydroxy.

In one class of this embodiment, the instant invention concerns compounds of Formula A' wherein M is hydroxy C$_{1-6}$ alkyl, or halo C$_{1-6}$ alkyl.

One sub-class of this embodiment concerns compounds of Formula A' wherein X$_8$ is hydrogen, C$_{1-6}$ alkyl, fluoro or chloro.

A narrower sub-class of this embodiment concerns compounds of Formula A' wherein M is 1-hydroxy-n-propyl, 2-hydroxy-n-propyl, 1-fluoro-n-propyl or 2-fluoro-n-propyl.

A second embodiment of the instant invention is directed to the compounds of the Formula (A')

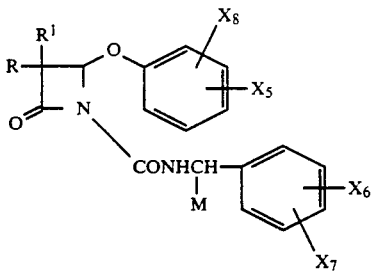

and pharmaceutically acceptable salts thereof wherein:
R is C$_{1-6}$ alkyl;
R$^1$ is C$_{1-6}$ alkyl or C$_{1-6}$ alkoxy-C$_{1-6}$ alkyl;
M is
 (1) hydrogen,
 (2) C$_{1-6}$ alkyl,
 (3) C$_{2-6}$ alkenyl, or
 (4) C$_{1-6}$ alkoxy-C$_{1-6}$ alkyl;
X$_5$ is
 (1) hydrogen,
 (2) C$_{1-6}$ alkyl,
 (3) halo-C$_{1-6}$ alkyl,
 (4) C$_{2-6}$ alkenyl,
 (5) C$_{2-6}$ alkynyl,
 (6) carboxy,
 (7) carboxy-C$_{1-6}$ alkyl,
 (8) carboxy-C$_{1-6}$ alkylcarbonyl,
 (9) carboxy-C$_{1-6}$ alkylcarbonylamino,
 (10) carboxy-C$_{2-6}$ alkenyl,
 (11) hydroxy-C$_{1-6}$ alkyl,
 (12) C$_{1-6}$ alkylcarbonyl, or
 (13) C$_{1-6}$ alkylcarbonylamino;
X$_8$ is hydrogen, halo or C$_{1-6}$alkyl; and
X$_6$ is
 (1) hydrogen,
 (2) C$_{1-6}$ alkyl,
 (3) halo
 (4) carboxy,
 (5) C$_{1-6}$ alkoxy,
 (6) phenyl,
 (7) C$_{1-6}$ alkylcarbonyl,
 (8) di-(C$_{1-6}$alkyl)amino, or
 (9) phenoxy; and
X$_7$ is hydrogen, or
X$_6$ and X$_7$ are joined together to form a ring selected from dioxcycloapentane and furan.

A class of this embodiment is the class of compounds of formula A' wherein

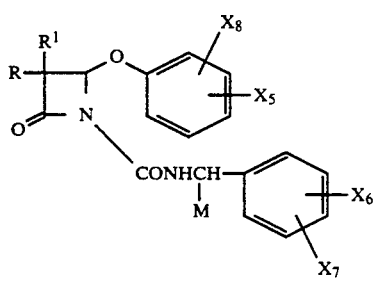

X$_5$ is carboxy or carboxy-C$_{1-6}$alkyl;
X$_8$ is hydrogen, F, Cl, CH$_3$ or CH$_2$CH$_3$;

M is C$_{1-3}$ alkyl or allyl; and
X$_6$ is hydrogen, C$_{1-6}$ alkyl, C$_{1-6}$alkoxy and
X$_7$ is hydrogen or
X$_6$ and X$_7$ are joined together to form a furan or dioxacyclopentane ring.

Exemplifying this class of the invention are the following compounds:

A compound which is (4S)-3,3-diethyl-1-[[(R)-1-(benzofuran-5-yl)butyl-amino]carbonyl]-4-](4-carboxymethyl)phenoxy]azetidin-2-one.

A compound which is (4S)-3,3-diethyl-1-[(R)-α-n-propyl-(4-methyl)benzylaminocarbonyl]-4-[(4-carboxy-3-chloro)phenoxy]azetidin-2-one.

A compound which is (4S)-3,3-diethyl-1-[(R)-α-n-propyl-(4-methyl)benzylaminocarbonyl]-4[(4-carboxy-3-fluoro)phenoxy]azetidin-2-one.

A compound which is (4S)-3,3-diethyl-1-[(R)-α-n-propyl-(4-methyl)benzylaminocarbonyl]-4-[(4-carboxy-3-methyl)-phenoxy]azetidin-2-one.

A compound which is (4S)-3,3-diethyl-1-[(R)-α-n-propyl-(4-ethoxy)benzylaminocarbonyl]-4-[(4-carboxymethyl)phenoxy]azetidin-2-one.

A compound which is (4S)-3,3-diethyl-1-[(R)-α-n-propyl-(4-methyl)benzylaminocarbonyl]-4-[(4-carboxymethyl-3-chloro)phenoxy]azetidin-2-one.

A compound which is (4S)-3,3-diethyl-1-[(R)-α-n-propyl-(4-methyl)benzylaminocarbonyl]-4-[(4-carboxymethyl-3-fluoro)phenoxy]azetidin-2-one.

Also within the scope of this invention are compounds of Formula A' wherein there is more than one X$_8$ group. Exemplifying is the compound (4S)-3,3-diethyl-1-[(R)-α-n-propyl-(1-(4-methylphenyl))-methylaminocarbonyl]-4-[(3,5-dimethyl-4-carboxy)-phenoxy]azetidin-2-one.

One second class within this embodiment is a compound of the formula (A)

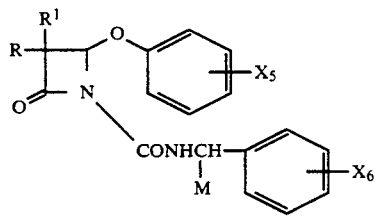

wherein:
R is C$_{1-6}$ alkyl;
R$^1$ is C$_{1-6}$ alkyl or alkoxy-C$_{1-6}$ alkyl;
M is
 (1) hydrogen,
 (2) C$_{1-6}$ alkyl,
 (3) C$_{2-6}$ alkenyl, or
 (4) C$_{1-6}$ alkoxy-C$_{1-6}$ alkyl;
X$_5$ is
 (1) hydrogen,
 (2) C$_{1-6}$ alkyl,
 (3) halo-C$_{1-6}$ alkyl,
 (4) C$_{2-6}$ alkenyl,
 (5) C$_{2-6}$ alkynyl,
 (6) carboxy,
 (7) carboxy-C$_{1-6}$ alkyl,
 (8) carboxy-C$_{1-6}$ alkylcarbonyl,
 (9) carboxy-C$_{1-6}$ alkylcarbonylamino,
 (10) carboxy-C$_{2-6}$ alkenyl,
 (11) hydroxy-C$_{1-6}$ alkyl,
 (12) C$_{1-6}$ alkylcarbonyl, or

(13) $C_{1-6}$ alkylcarbonylamino; and $X_6$ is (1) hydrogen, (2) $C_{1-6}$ alkyl, (3) halo, (4) carboxy, (5) $C_{1-6}$ alkoxy, (6) phenyl, (7) $C_{1-6}$ alkylcarbonyl, (8) di-($C_{1-6}$alkyl)amino, (9) phenoxy, or

(10) methylenedioxy; or a pharmaceutically acceptable salt thereof.

One class of this embodiment is the class of compounds of the formula (A) wherein $X_5$ is carboxy or carboxy-$C_{1-6}$ alkyl. A subclass of these compounds are those compounds of the class wherein M is $C_{1-3}$ alkyl or allyl and $X_6$ is hydrogen, $C_{1-6}$ alkyl, or 3,4-methylenedioxy or phenyl. Illustrating this subclass are those compounds wherein R is ethyl; and $R^1$ is methyl or ethyl. Exemplifying this invention are the following compounds:

(1) (4S)-3,3-diethyl-1-[(R)-α-ethylbenzyl-aminocarbonyl]-4-[(4-carboxymethyl)phenoxy]azetidin-2-one;

(2) (4S)-3,3-diethyl-1-[(R)-α-n-propylbenzylaminocarbonyl]-4-[(4-carboxymethyl)phenoxy]azetidin-2-one;

(3) (4S)-3,3-diethyl-1-[(R)-α-allyl-(4-methyl)benzylaminocarbonyl]-4-[(4-carboxymethyl)phenoxy]azetidin-2-one;

(4) (4S)-3,3-diethyl-1-[(R)-α-allyl-(3,4-methylenedioxy)-benzylaminocarbonyl]-4-[(4-carboxymethyl)-phenoxy]azetidin-2-one;

(5) (4S)-3,3-diethyl-1-[(R)-α-n-propyl-(3,4-methylenedioxy)-benzylaminocarbonyl]-4[(4-carboxymethyl)-phenoxy]azetidin-2-one;

(6) (4S)-3,3-diethyl-1-[(R)-α-n-propyl-(4-methyl)-benzylaminocarbonyl]-4-[(4-carboxy)phenoxy]azetidin-2-one; and (7) (4S)-3,3-diethyl-1-[(R)-α-n-propyl-(4-methyl)-benzylaminocarbonyl]-4-[(4-carboxymethyl)-phenoxy]azetidin-2-one.

The compounds of the invention are prepared by known methods or are prepared among other methods by the following representative schemes.

Scheme (a) as illustrated by Examples 16-19.

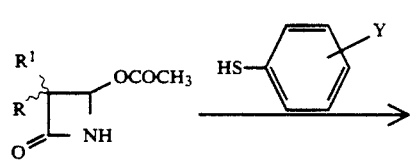

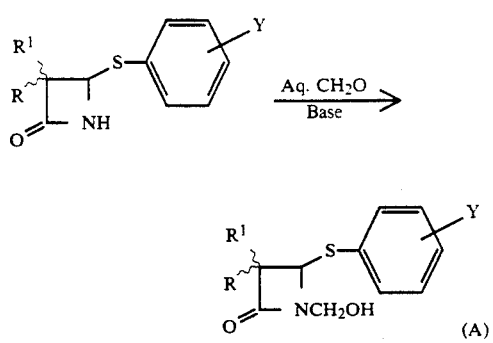

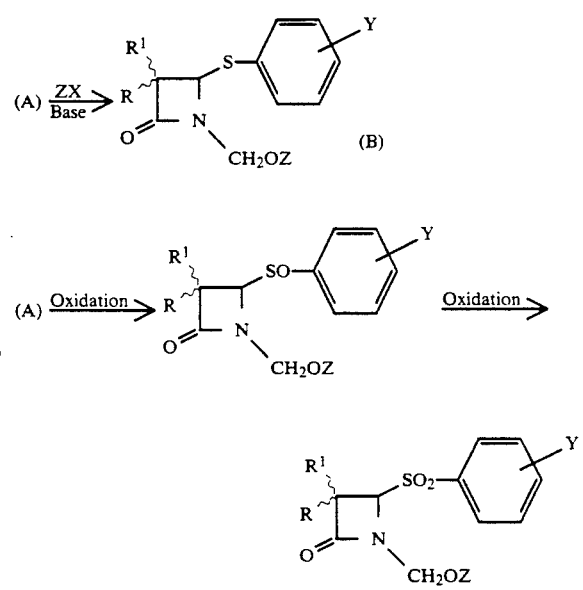

wherein

Y is —NO$_2$, —CH$_3$, —OCH$_3$, —Cl, —F, CO$_2$H, etc;

X is halo, e.g., Cl, Br or I;

Z is BCO or BSO$_2$.

Scheme (b) as illustrated by Examples 1-4.

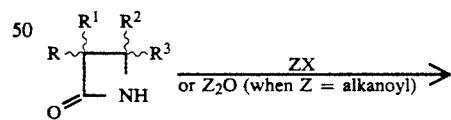

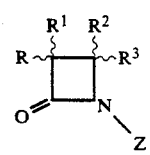

wherein

X is halo; Z is as previously defined, e.g., —SO$_2$—(-p—NO$_2$—Ph), —COCH$_3$, —CH$_2$OTs, CO$_2$Et, etc.

wherein Ph represents phenyl or substituted phenyl.

Scheme (c) as illustrated by Examples 5-15

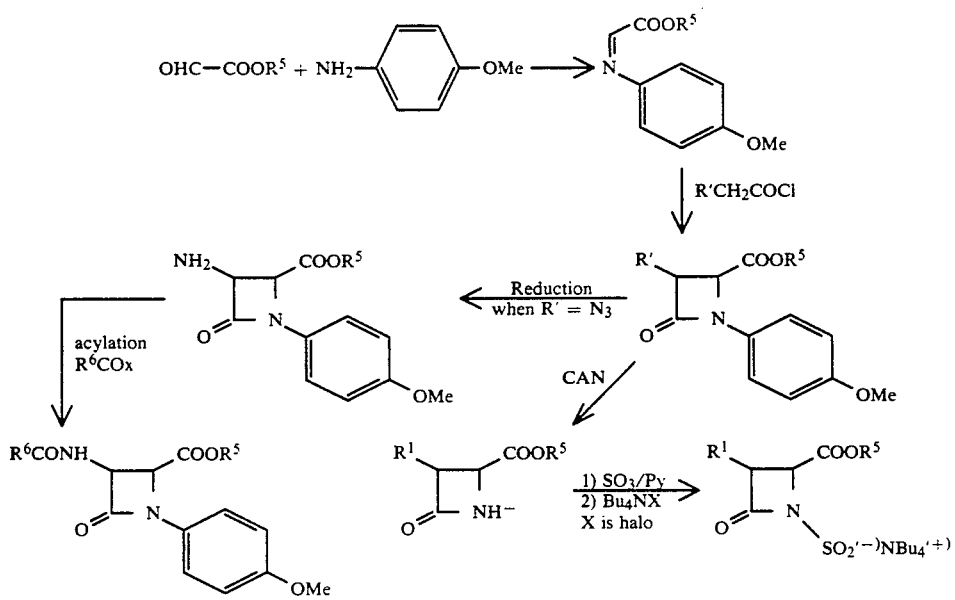

wherein
R[6] is H, CF$_3$, CH$_3$, etc.;
R[5] and R[1] are as previously defined; and CAN is ceric ammonium nitrate.
Scheme (d) as illustrated by Examples 2-3.

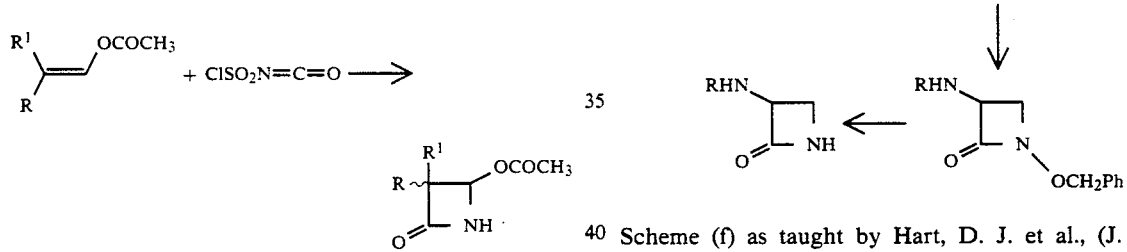

Scheme (e) as taught by M. A. Krook and M. J. Miller (J. Org. Chem., 1985, 50, 1126-1128), the following type of compounds can be prepared.

Scheme (f) as taught by Hart, D. J. et al., (J. Org. Chem., 48, pp. 289-294, 1983); the following class of compounds can be prepared.

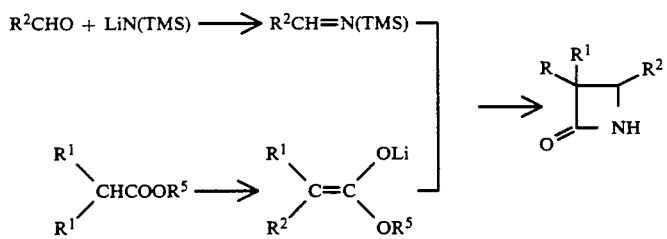

wherein R[5] is as previously defined; and TMS is trimethylsilyl.
Scheme (g) as taught by P. J. Reider and E. J. J. Grabowski (Tet. Lett., 23, p. 2293, 1982); the following groups of compounds can be prepared.

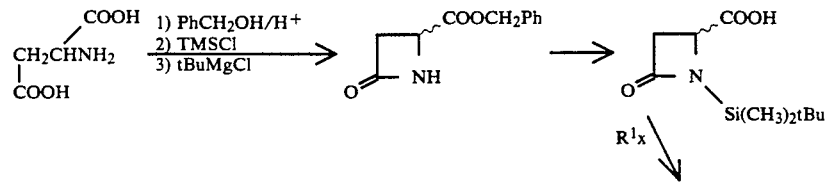

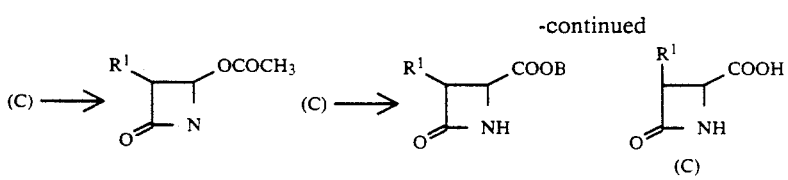

wherein $R^1$ is as previously defined.

The compounds of the instantly claimed invention are conveniently prepared according to the Scheme (h) as illustrated by Examples 20 and 21:

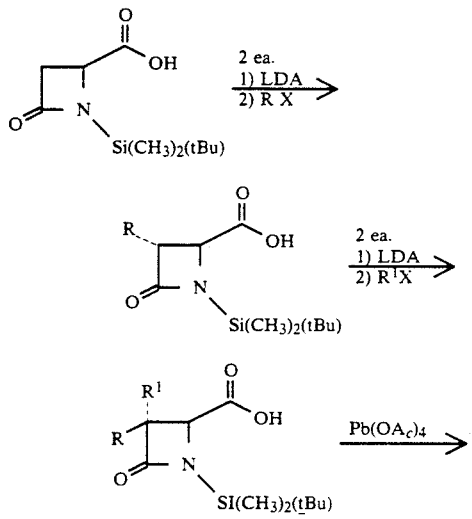

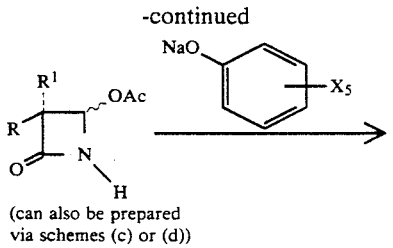

(can also be prepared via schemes (c) or (d))

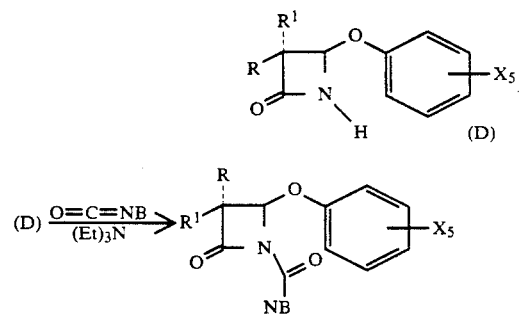

This invention also relates to a method of treating inflammation in patients using a compound of Formula (I), Formula A or Formula A', particularly a preferred compound as the active constituent.

It has been found that the compounds of Formula (I), Formula A or Formula A' are effective inhibitors of the proteolytic function of human granulocyte elastase as shown below:

TABLE I

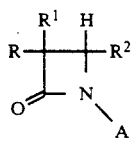

| R | $R^1$ | $R^2$ | A | $ID_{50}$ (mg/ml) | $K_i$ (mM) | $k_{obs}/I$ $(M^{-1} sec^{-1})$ |
|---|---|---|---|---|---|---|
| H | H | $SOCH_3$ | $COCH_3$ | 10.00 | | |
| H | H | $OCOCH_3$ | $COCH_3$ | 3.00 | | |
| H | $C_2H_5$ | $OCOCH_3$ | H | 15.00 | | |
| H | $C_2H_5$ | $OCOCH_3$ | $COCH_3$ | 0.10 | 0.36 | 15100 |
| H | n-propyl | $OCOCH_3$ | $COCH_3$ | 0.01 | | |
| H | $C_6H_5$ (trans) | $COOC_2H_5$ | H | 10.00 | | |
| H | H | $COOCH_2C_6H_5$ | $SO_2(p-C_6H_4-NO_2)$ | 3.00 | | |
| $CH_3$ | $CH_3$ | $OCOCH_3$ | $COCH_3$ | 0.50 | | |
| H | $C_6H_5$ (trans) | $COOC_2H_5$ | $SO_2(p-C_6H_4-NO_2)$ | 4.00 | | |
| H | $C_6H_5$ (cis) | $COOC_2H_5$ | $SO_2(p-C_6H_4-NO_2)$ | 3.00 | | |
| H | $CH_3O$ | $COOCH_2C_6H_5$ | $COCH_3$ | 2.00 | | |
| H | n-propyl | $OCOCH_3$ | $SO_3^-(Bu)_4N^+$ | 8.00 | | |
| H | $C_2H_3$ (cis) | $COOC_2H_5$ | $SO_2(p-C_6H_4-NO_2)$ | 0.02 | | |
| H | $C_2H_5$ (cis) | $COOC_2H_5$ | $SO_2(p-C_6H_4-NO_2)$ | 0.05 | | 3925 |
| H | $C_2H_5$ (trans) | $COOC_2H_5$ | $SO_2(p-C_6H_4-NO_2)$ | 0.05 | | 39300 |
| H | $C_2H_5$ (trans) | $COOC_2H_5$ | $SO_2(p-C_6H_4-CH_3)$ | 0.01 | | |
| H | n-propyl (trans) | $COOC_2H_5$ | $SO_2(p-C_6H_4-NO_2)$ | 0.06 | | |
| H | $CH_3CHCH$ (cis) | $COOC_2H_5$ | $SO_2(p-C_6H_4-NO_2)$ | 0.05 | | |
| H | $CH_2CH$ | $p-(C_6H_4-NO_2)$ | H | 1.50 | | |
| H | $C_2H_5$ | $OCOCH_2CH_2COOH$ | $COCH_3$ | | 2.00 | 4514 |
| H | $C_2H_5$ (trans) | $OCOPh$ | $COCH_3$ | | 0.19 | 81000 |
| H | $C_2H_5$ (cis) | $OCOPh$ | $COCH_3$ | | 0.21 | 28500 |
| H | $C_2H_5$ | $OCOCH_3$ | $COCH_2CH_2COOH$ | | 1.43 | 2250 |
| H | $C_2H_5$ (cis) | $OCOCH_3$ | $COPh$ | | 0.14 | |

TABLE I-continued

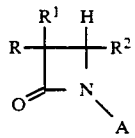

| R | R$^1$ | R$^2$ | A | ID$_{50}$ (mg/ml) | Ki (mM) | $k_{obs}$/I (M$^{-1}$sec$^{-1}$) |
|---|---|---|---|---|---|---|
| H | C$_2$H$_5$ (trans) | COCH$_3$ | COPh | | 0.34 | 76600 |
| H | C$_2$H$_5$ (trans) | OPh | COCH$_3$ | | 4.30 | 5270 |
| H | C$_2$H$_5$ (trans) | OC$_2$H$_5$ | COCH$_3$ | | 11.90 | 1670 |
| H | C$_2$H$_5$ (trans) | OPh-p-COOH | COCH$_3$ | | 3.40 | 8727 |
| H | C$_2$H$_5$ (trans) | OPh-p-COOH | COOC$_2$H$_5$ | | 2.10 | 8680 |
| H | C$_2$H$_5$ (trans) | OPh-p-COOH | CONHCH$_3$ | | 16.50 | |
| H | C$_2$H$_5$ (cis) | CON(CH$_2$)$_4$ | SO$_2$(p-C$_6$H$_4$—CH$_3$) | | 27.70 | 541 |
| H | C$_2$H$_5$ (cis) | COOCH$_2$C$_6$H$_4$-p-COOH | SO$_2$(p-C$_6$H$_4$—CH$_3$) | | 4.20 | 299 |
| H | C$_2$H$_5$ (cis) | CON(CH$_3$)CH$_2$COOH | SO$_2$(p-C$_6$H$_4$—CH$_3$) | | 22.00 | 165 |
| H | C$_2$H$_5$ (trans) | OCH$_2$COOH | COOC$_2$H$_5$ | | | 512 |
| H | C$_2$H$_5$ (cis) | OCH$_2$COOH | COOC$_2$H$_5$ | | | 796 |
| H | n-propyl (trans) | OCH$_2$COOH | COOC$_2$H$_5$ | | | 1504 |
| H | C$_2$H$_5$ (trans) | OCH$_2$CONHCH$_2$COOH | COOC$_2$H$_5$ | | | 1000 |
| H | C$_2$H$_5$ (cis) | OCH(CH$_3$)COOH | COOC$_2$H$_5$ | | | 346 |
| H | C$_2$H$_5$ (cis) | COOCH$_2$COOH | SO$_2$(P—C$_6$H$_4$—CH$_3$) | | | 1554 |

ID$_{50}$ is the effective dosage in micrograms per milliliter (mg/ml) for 50% inhibition of the enzyme activity two minutes after time zero. Ki is the concentration of the inhibitor (micromolar, mM) giving 50% of the control enzyme activity. $k_{obs}$/I (M$^{-1}$ sec$^{-1}$) is the second order rate constant of inactivation of the enzyme.

TABLE II

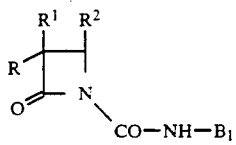

| R | R$^1$ | R$^2$ | B$_1$ | $k_{obs}$/I |
|---|---|---|---|---|
| C$_3$H$_7$ | CH$_3$ | O-(4-COOH—Ph) | CH$_2$Ph | 1900 |
| C$_2$H$_5$ | CH$_3$ | O-(4-COOH—Ph) | CH(CH$_3$)Ph | 15,000 |
| C$_3$H$_7$ | H | O-(4-COOH—Ph) | CH$_2$Ph | 5,000 |
| C$_2$H$_5$ | C$_2$H$_5$ | O-(4-CO(CH$_2$)$_2$COOH—Ph) | CH$_2$(4-Ph—Ph) | 107,045 |
| C$_2$H$_5$ | C$_2$H$_5$ | O-(4-COOH—Ph) | CH$_2$(4-Ph—Ph) | 37,000 |
| C$_2$H$_5$ | CH$_2$OCH$_3$ | O-(4-COOH—Ph) | CH$_2$(4-Ph—Ph) | 44,533 |
| C$_2$H$_5$ | C$_2$H$_5$ | O-(4-NO$_2$—Ph) | CH$_2$Ph | 6,847 |
| C$_2$H$_5$ | C$_2$H$_5$ | O-(4-COOH—Ph) | CH$_2$ (2-Anthracene) | 36,177 |
| C$_2$H$_5$ | C$_2$H$_5$ | O-(2-CH$_2$OH—Ph) | CH$_2$Ph | 2961 |
| C$_2$H$_5$ | C$_2$H$_5$ | O-(4-CH$_2$COOH—Ph) | CH$_2$Ph | 3175 |
| C$_2$H$_5$ | C$_2$H$_5$ | O-(4-CH$_2$CH—NH$_3^+$—Ph) CO$_2^-$ | CH$_2$Ph | 2540 |
| C$_2$H$_5$ | C$_2$H$_5$ | O-(4-NHCOCH$_3$—Ph) | CH$_2$Ph | 3503 |
| C$_2$H$_5$ | C$_2$H$_5$ | O-(4-NHCOCH$_2$CH$_2$COOH—Ph) | CH$_2$Ph | 2568 |
| C$_2$H$_5$ | C$_2$H$_5$ | O-(4-CH$_3$CO—Ph) | CH$_2$-(4-COOH—Ph) | 2807 |
| C$_2$H$_5$ | C$_2$H$_5$ | O-(4-CH$_3$CO—Ph) | CH$_2$(4-CH$_3$CO—Ph) | 5916 |
| C$_2$H$_5$ | C$_2$H$_5$ | O-(4-COOH—Ph) | CH$_2$-(2-furyl) | 5223 |
| C$_2$H$_5$ | C$_2$H$_5$ | O-(4-COOH—Ph) | CH$_2$-(2-thienyl) | 4925 |
| C$_2$H$_5$ | C$_2$H$_5$ | O-(4-COOH—Ph) | n-C$_9$H$_{19}$ | 8300 |
| C$_2$H$_5$ | C$_2$H$_5$ | O-(4-COOH—Ph) | (CH$_2$)$_3$Ph | 4537 |
| C$_2$H$_5$ | C$_2$H$_5$ | O-(4-COOH—Ph) | CH$_2$Naph | 21,269 |
| C$_2$H$_5$ | C$_2$H$_5$ | O-(4-COOH—Ph) | (CH$_2$)$_4$Ph | 10,894 |
| C$_2$H$_5$ | C$_2$H$_5$ | O—Ph | CH$_2$-(4-COOH—Ph) | 1501 |
| C$_2$H$_5$ | C$_2$H$_5$ | O-(4-COOH—Ph) | CH$_2$-cyclohexyl | 1424 |
| C$_2$H$_5$ | H | O-(4-COOH—Ph) | CH$_2$Ph | 4000 |
| C$_2$H$_5$ | CH$_3$ | O-(4-COOH—Ph) | CH$_2$Ph | 2000 |
| CH$_2$CH=CH$_2$ | H | O-(4-COOH—Ph) | CH$_2$Ph | 5400 |
| C$_3$H$_7$ | C$_2$H$_5$ | O-(4-COOH—Ph) | CH$_2$Ph | 3280 |
| cyclopentane (R and R$^1$ combined and form the cyclopentane ring) | | O-(4-COOH—Ph) | CH$_2$Ph | 1900 |
| C$_2$H$_5$ | CH$_2$OCH$_3$ | O-(4-COOH—Ph) | CH$_2$Ph | 1900 |
| C$_2$H$_5$ | CH$_3$ | O-(4-COOH—Ph) | CH$_2$CH(CH$_3$)Ph | 2553 |
| C$_2$H$_5$ | C$_3$H$_7$ | O-(4-COOH—Ph) | CH$_2$-(2-Naph) | 51,000 |
| C$_2$H$_5$ | C$_2$H$_5$ | O-(4-COOH—Ph) | CH(CH$_3$)-(1-Naph) | 14,128 |
| C$_2$H$_5$ | C$_2$H$_5$ | O-(4-COOH—Ph) | CH$_2$-(4-Cl—Ph) | 3419 |
| C$_2$H$_5$ | C$_2$H$_5$ | O-(4-COOH—Ph) | CH$_2$(4-CH$_3$—Ph) | 3965 |
| C$_2$H$_5$ | C$_2$H$_5$ | O-(4-COOH—Ph) | CH$_2$(4-F—Ph) | 2337 |
| C$_2$H$_5$ | C$_2$H$_5$ | O-(4-COOH—Ph) | CH$_2$(4-OCH$_3$—Ph) | 5162 |

TABLE II-continued $$\begin{array}{c} R^1 \; R^2 \\ R-\!\!\!\!\diagup \\ O\!=\!\!\!\diagdown N \\ \phantom{O=}|\\ \phantom{O=}CO-NH-B_1 \end{array}$$

| R | R$^1$ | R$^2$ | B$_1$ | k$_{obs}$/I |
|---|---|---|---|---|
| C$_2$H$_5$ | C$_2$H$_5$ | O-(4-COOH—Ph) | CH$_2$(4-NO$_2$—Ph) | 5075 |
| C$_2$H$_5$ | C$_2$H$_5$ | O-(4-COOH—Ph) | CH(CH$_3$)-(3-Cl-4-cyclo-hexyl-Ph) | 20,776 |
| C$_2$H$_5$ | CH$_2$OCH$_3$ | O-(4-COOH—Ph) | CH$_2$-(3,4-methylene-dioxy-Ph) | 16,984 |
| C$_2$H$_5$ | C$_2$H$_5$ | O-(4-COOH—Ph) | CH$_2$-(2-benzofuran) | 13,151 |
| C$_2$H$_5$ | C$_2$H$_5$ | O-(2-(6-COOH-Naph)) | CH$_2$Ph | 5561 |
| C$_2$H$_5$ | C$_2$H$_5$ | O-(4-COOH—Ph) | CH$_2$(4-(4-Cl—Ph)-SO$_2$NHCO—Ph) | 1730 |
| C$_2$H$_5$ | C$_2$H$_5$ | O-(3-CO—NHCH$_2$—Ph) | CH$_2$Ph | 3047 |
| C$_2$H$_5$ | C$_2$H$_5$ | O-(3-COOH—Ph) | CH$_2$Ph | 1763 |
| C$_2$H$_5$ | C$_2$H$_5$ | O-(4-COOH—Ph) | CH$_2$-(4-PhO—Ph) | 12,036 |
| C$_2$H$_5$ | C$_2$H$_5$ | O-(4-COOH—Ph) | CH$_2$-(4-HN(CH$_3$)$_2$—Ph) "CF$_3$COO$^-$ | 9983 |
| C$_2$H$_5$ | C$_2$H$_5$ | O-(4-COOH—Ph) | (CH$_2$)$_4$OPh | 3447 |
| C$_2$H$_5$ | C$_2$H$_5$ | O-(4-COOH—Ph) | (CH$_2$)$_4$CH(OH)Ph | 4200 |
| C$_2$H$_5$ | C$_2$H$_5$ | O-(4-N(CH$_3$)$_3$I$^-$Ph | CH$_2$Ph | 1700 |
| C$_2$H$_5$ | C$_2$H$_5$ | -1-imidazolyl | CH$_2$Ph | 200 |
| C$_2$H$_5$ | C$_2$H$_5$ | (4-O-Ph)-N-pyrrolidinyl-CO, with CO$_2$H on α-carbon | CH$_2$Ph— | 2000 |
| C$_2$H$_5$ | C$_2$H$_5$ | O-Ph-CONHSO$_2$-(4-Cl-Ph) | CH$_2$Ph | 6300 |
| C$_2$H$_5$ | C$_2$H$_5$ | O-Ph-CH(CO$_2$H)(NHCOCH$_3$) | CH$_2$Ph | 2422 |
| C$_2$H$_5$ | H | O-(4-COOH—Ph) | Ph-4-COOH | 13,563 |
| C$_3$H$_7$ | C$_3$H$_7$ | O-(4-COOH—Ph) | CH$_2$Ph | 2,500 |
| allyl | C$_2$H$_5$ | O-(4-COOH—Ph) | CH$_2$Ph | 1974 |
| CH$_2$Ph | C$_2$H$_5$ | O-(4-COOH—Ph) | CH$_2$Ph | 87 |
| C$_2$H$_5$ | CH$_2$OCH$_3$ | O-(4-COOH—Ph) | CH$_2$-2-Naph | 50,000 |
| C$_2$H$_5$ | H | Ph-4-COOH | CH$_2$Ph | 900 |
| H | OMe | Ph-4-COOH | CH$_2$-2-Naph | 1340 |
| C$_2$H$_5$ | C$_3$H$_7$ | O-(4-COOH—Ph) | CH$_2$Ph-3-CF$_3$ | 55,000 |
| C$_2$H$_5$ | CH$_3$ | O-(4-COOH—Ph) | CH(Et)-5-benzofuryl | 750,000 |
| C$_2$H$_5$ | CH$_3$ | O-(4-COOH—Ph) | CH(Et)-3-thienyl | 78,800 |
| C$_2$H$_5$ | CH$_2$OCH$_3$ | O-(4-COOH—Ph) | CH(nPr)Ph | 75,000 |
| C$_2$H$_5$ | C$_3$H$_7$ | O-(4-CO(CH$_2$)$_2$COOH—Ph) | CH(Et)Ph | 87,000 |
| C$_2$H$_5$ | C$_3$H$_7$ | O-(4-CH$_2$COOH—Ph) | CH(Et)Ph | 54,000 |
| C$_2$H$_5$ | CH$_3$ | O-(4-COOH—Ph) | Cyclopentyl | — |
| C$_2$H$_5$ | CH$_3$ | O-(4-COOH—Ph) | CH(CH$_3$)CH$_2$CH$_2$CH$_3$ | — |
| C$_2$H$_5$ | CH$_3$ | O-(4-CONH$_2$Ph) | CH$_2$Ph | 12,500 |
| C$_2$H$_5$ | CH$_3$ | O-(4-COOH—Ph) | CH$_2$(3,5-diMe-4-COOH—Ph) | 5,600 |
| C$_2$H$_5$ | CH$_3$ | O-(4-CONH$_2$Ph) | CH$_2$(3,5-diMe-4-COOH—Ph) | 30,000 |
| C$_2$H$_5$ | CH$_3$ | O-(4-COOH—Ph) | CH$_2$(3,4-diMeO—Ph) | 11,300 |

Me represents CH$_3$
Ph represents phenyl
Pr represents propyl
Bu represents butyl

TABLE III

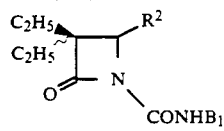

| $R^2$ | $B^1$ | $k_{obs}/I$ |
|---|---|---|
| OCH$_2$COOH | CH$_2$Ph-4-Ph | 2901 |
| O-(4-COOH—Ph) | 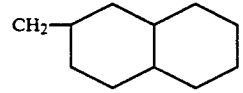 CH$_2$-decahydronaphthyl | 4157 |
| O-(allyl) | CH$_2$Ph-4-Ph | 12,545 |
| -1-imidazole | CH$_2$Ph-4-Ph | 461 |
| 1-triazolyl | CH$_2$Ph-4-Ph | 2144 |
| (1-methyl-tetrazol-5-yl)thio | CH$_2$Ph | 3658 |
| (1-H-triazol-3-yl)thio | CH$_2$Ph | 116 |
| 1-tetrazolyl | CH$_2$Ph | 948 |
| [2H-1-pyridonyl] | CH$_2$Ph | 357 |
| O—Ph-4-CONH$_2$ | CH$_2$-2-Naph(6-COOH) | 40,650 |
| 1-benzimidazolyl | CH$_2$Ph | 69 |
| 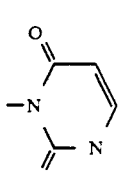 pyrimidine-dione | CH$_2$Ph | 351 |
| O-glyceryl | CH$_2$Ph | 818 |
| OCH$_2$CONH$_2$ | CH$_2$—Ph-4-Ph | 51,802 |
| NH—COOMe | CH$_2$Ph | 496 |

TABLE III-continued

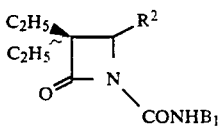

| $R^2$ | $B^1$ | $k_{obs}/I$ |
|---|---|---|
| OCH$_2$—COOH | CH—(Et)—Ph | 5711 |
| OCH$_2$—CONH$_2$ | CH—(Et)—Ph | 102,974 |
| O-(4-COOH—Ph) | nBu | — |
| O-(4-COOH—Ph) | cyclopentyl | — |
| O—CH$_2$CON(Et) | CH(Et)Ph | — |
| O-(4-COOH—Ph) | CH$_2$Ph(2-OH) | 1461 |
| O-(4-COOH—Ph) | CH$_2$Ph(4-tBu) | 21,774 |
| O-(4-COOH—Ph) | CH$_2$Ph(4-(3-COOH)Ph) | 14,727 |
| O-(4-COOH—Ph) | CH$_2$Ph(4-CO—N-morpholino) | 2036 |
| O-(4-COOH—Ph) | CH$_2$Ph(4-CH$_2$Ph) | 8032 |
| O-(4-COOH—Ph) | CH$_2$Ph(3-CH$_3$) | 6932 |
| O-(4-COOH—Ph) | CH$_2$Ph(3,4-(CH$_2$)$_4$) | 62,883 |
| O-(4-COOH—Ph) | CH$_2$Ph(3,4-DiMe) | 20,600 |
| O-(4-COOH—Ph) | CH$_2$Ph(4-i-Pr) | 18,846 |
| O-(4-COOH—Ph | CH$_2$Ph(4-S(O)$_2$Me) | 3350 |
| O-(4-COOH—Ph) | CH$_2$Ph(4-COMe) | 5916 |
| O-(4-COOH—Ph) | CH$_2$Ph(4-OMe-3-Me) | 13,126 |
| O-(4-COOH—Ph) | CH$_2$—Ph(4-OCH$_2$Ph) | 12,036 |
| O-(4-CH(COOH)NHAc—Ph) | CH$_2$Ph | 1676 |
| O-(4-CH(OH)COOH—Ph) | CH$_2$Ph(3,4-DiMe) | 17,626 |
| O-(3-OH-4-COOH—Ph) | CH$_2$Ph(4-Me) | 9252 |
| O-(2-(CH$_2$)$_3$NMe$_2$—Ph) | CH$_2$Ph | 629 |
| O-(4-CH$_2$COOH—Ph) | CH$_2$Ph(4-Ph) | 28,870 |

TABLE IV

| R | $R^1$ | $R^2$ | B | $k_{obs}/I$ |
|---|---|---|---|---|
| C$_2$H$_5$ | —CH$_3$ | O-(4-COOH—Ph) | tetrahydroisoquinolinyl (CH$_2$ linker) | 4376 |
| C$_2$H$_5$ | —H | O-(4-COOH—Ph) | tetrahydroisoquinolinyl | 10,066 |
| C$_3$H$_7$ | C$_3$H$_7$ | O-(4-COOH—Ph) | —NH—CH(CH$_3$)(Ph) 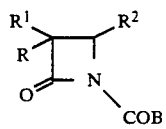 | 1446 (lower R$_f$ isomer) / 4324 (higher R$_f$ isomer) |
| C$_2$H$_5$ | H | O-(4-COOH—Ph) | -N(CH$_2$Ph)$_2$ | 5977 |
| C$_2$H$_5$ | H | O-(4-COOH—Ph) | -OCH$_2$-(4-COOC$_2$H$_5$—Ph) | 227,460 |
| C$_2$H$_5$ | C$_2$H$_5$ | O-(4-COOH—Ph) | -OCH$_2$-(4-COOC$_2$H$_5$—Ph) | 14,331 |
| C$_2$H$_5$ | H | O-(4-COOH—Ph) | -N(C$_2$H$_5$)(CH$_2$Ph) | 82,956 |

TABLE IV-continued

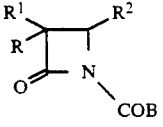

| R | R¹ | R² | B | | $k_{obs}/I$ |
|---|---|---|---|---|---|
| $C_2H_5$ | $C_2H_5$ | O-(4-$CH_2$COOH—Ph) | 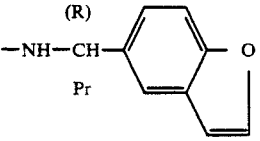 | | 847,000 |

TABLE V

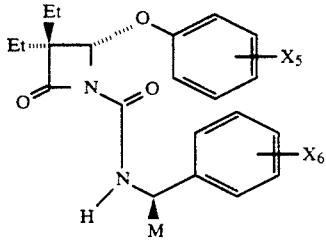

| $X_5$ | M | $X_6$ | $k_{obs}/I$ |
|---|---|---|---|
| 4-COOH | Et | H | 92,000 |
| 4-COOH | $CH_2$OMe | H | 6,094 |
| 4-$CH_2$COOH | Et | H | 140,000 |
| 4-COOH | Me | 4-Me | 47,000 |
| 4-COOH | Et | 4-Me | — |
| 4-COOH | $PhCH_2$ | H | 25,000 |

TABLE V-continued

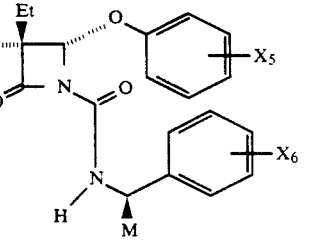

| $X_5$ | M | $X_6$ | $k_{obs}/I$ |
|---|---|---|---|
| 4-$CH_2$COOH | nPr | H | 227,000 |
| 4-COOH | nPr | $CH_3$ | — |
| 4-COOH | nPr | H | 120,000 |
| 4-COOH | Et | 3,4-($OCH_2$O) | — |
| 4-$CH_2$COOH | nBu | H | — |
| 4-COOH | allyl | H | — |

TABLE VI

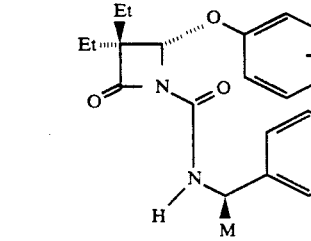

| $X_5$ | M | $X_6$ | $k_{obs}/I$ |
|---|---|---|---|
| 4-COOH | Me | H | 4016 |
| 4-COOH | Me | 4-Ph | 74,000 |
| 4-$CH_2$COOH | Me | H | 8,373 |
| 4-COOH | Me(s) | 4-Ph | 49246 |
| 4-COOH | Ph | 4-Ph | 67754 |
| 4-COOH | Me | 4-(2'-Cl—Ph) | 245130 |
| 4-COOH | Et | 4-Ph | 26382 |
| 4-COOH | Et | H | 76204 |
| 4-CO—($CH_2$)$_2$—COOH | Me | H | 37084 |
| 4-CO—($CH_2$)$_2$COOH | Et | H | 272190 |
| 3,5-$Me_2$-4-COOH | Et | H | 24,994 |
| 4-$CH_2$COOH | Et | H | 126,000 |
| 3-OH-4-COOH | Et | H | 124560 |
| 3-$CH_2$COOH | Me | H | 5885 |
| 4-CH=CH—COOH | Me | H | 9101 |
| 4-COOH | $CH_2$OMe(s) | H | 6981 |
| 4-$CH_2$COOH | $CH_2$OMe(s) | H | — |
| 4-COOH | Me | 4-Me | 10680 |
| 4-COOH | iPr(S) | H | 4743 |
| 4-COOH | iPr | H | 177075 |
| 4-$CH_2$COOH | nPr | H | 188,000 |
| 4-$CH_2$COOH | $CH_2$OMe(R) | H | 11004 |
| 3,5-$Me_2$-4-COOH | nPr | H | |
| 3-$CH_2$COOH | Et | 4-Me | |
| 4-($CH_2$)$_2$COOH | Me | H | 9481 |

TABLE VI-continued

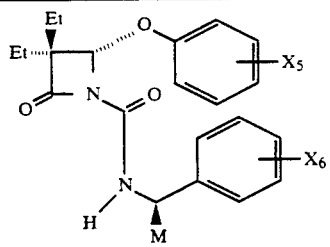

| $X_5$ | M | $X_6$ | $k_{obs}/I$ |
|---|---|---|---|
| 3-CH$_2$COOH | Et | H | 81018 |
| 4-COOH | CH$_2$OMe(R) | H | 6981 |
| 4-COOH | Et | 3-Me | |
| 4-CH$_2$COOH | Et | 3-Me | |
| 4-CO(CH$_2$)$_2$COOH | allyl | 4-Me | |
| 4-COOH | Me | 4-Me | |
| 4-CH$_2$COOH | Et | 3-Cl | |
| 4-COOH | Et | 3-Cl | |
| 4-COOH | allyl | 3-Me | |
| 4-COOH | nPr | 3-Me | |
| 4-CH$_2$COOH | allyl | 4-Me | 664,000 |
| 3-CH$_2$COOH | allyl | 4-Me | |
| 4-CH$_2$COOH | allyl | 3-Me | |
| 4-CH$_2$COOH | nPr | 3-Me | |
| 4-CO(CH$_2$)$_2$COOH | nPr | 4-Me | |
| 3-CH$_2$COOH | allyl | H | |
| 3-CH$_2$COOH | CH$_2$OMe(S) | H | |
| 4-COOH | allyl | H | |
| 4-CH$_2$COOH | allyl | H | |
| 4-COOH | Et | 4-Me | |
| 4-COOH | Et(S) | 4-Me | |
| 4-COOH | allyl | 4-Me | |
| 4-COOH | nPr | 4-Me | 389,000 |
| 3-CH$_2$COOH | nPr | 4-Me | |
| 4-CH$_2$COOH | nPr | 4-Me | 557,000 |
| 3-CH$_2$COOH | Et | 4-Cl | |
| 4-COOH | Et | 4-Cl | |
| 4-CH$_2$COOH | Et | 4-Me | |
| 3-CH$_2$COOH | Et | 3-Cl | |
| 4-COOH | allyl | 3,4-methylenedioxy | |
| 4-COOH | nPr | 3,4-methylenedioxy | |
| 4-CH$_2$COOH | allyl | 3,4-methylenedioxy | 605,000 |
| 4-CH$_2$COOH | nPr | 3,4-methylenedioxy | 867,000 |
| 3-CH$_2$COOH | CH$_2$COOH | 4-Me | |
| 3-CH$_2$COOH | nPr | H | |
| 4-COOH | Et | 3,4-methylenedioxy | |
| 4-CH$_2$COOH | Et | 3,4-methylenedioxy | |
| 4-COOH | Et | 3,4-Me$_2$ | |
| 4-COOH | CH$_2$C=CCH$_3$ | H | |
| 4-CH$_2$COOH | CH$_2$C=CCH$_3$ | H | |
| 4-COOH | nBu | H | |
| 2-NO$_2$-4-CH$_2$COOH | Et | H | |
| 4-COOH | Et | 4-F | |
| 4-COOH | Et | 3-Me-4-OMe | |
| 3-F,4-COOH | nPr | 4-Me | 464,500 |
| 3-Cl,4-COOH | nPr | 4-Me | 621,000 |
| 3-Me,4-COOH | nPr | 4-Me | 186,500 |
| 3-F,4-CH$_2$COOH | nPr | 4-Me | 637,000 |
| 3-Cl,4-CH$_2$COOH | nPr | 4-Me | 589,000 |
| 3-Me,4-CH$_2$COOH | nPr | 4-Me | 998,000 |
| 4-Ch$_2$—(OOH) | nPr | 3,4(-CH=CH—O—) | 848,000 |

Enzyme Assays for the Inhibition of Human Polymorphonuclear Leukocyte Elastase Via Hydrolysis of N-t-Boc-alanyl-alanyl-prolylalanine-p-nitroanilide (Boc-AAPAN) or N-t-Boc-alanyl-prolylvaline-p-nitroanilide (Boc-AAPVN) Reagent:

0.05M TES (N-tris[hydroxymethyl]methyl-2-aminoethanesulfonic acid) Buffer, pH 7.5.

0.2 mM Boc-AAPAN or Boc-AAPVN.

To prepare substrate, the solid was first dissolved in 10.0 ml DMSO. Buffer at pH 7.5 was then added to a final volume of 100 ml.

Crude extract of human polymorphonuclear leukocytes (PMN) containing elastase activity.

Inhibitors (azetidinones) to be tested dissolved in DMSO just before use.

To 1.0 ml of 0.2 mM Boc-AAPAN in a cuvette, 0.01–0.1 ml of DMSO with or without inhibitor was added. After mixing, a measurement was taken at 410 m$\mu$ to detect any spontaneous hydrolysis due to presence of test compound. 0.05 Milliliters of PMN extract was then added and the $\Delta$OD/min at 410 m$\mu$ was measured and recorded. Beckman model 35 spectrophotometer was used.

Results in Table I were reported as $ID_{50}$, effective dosage in micrograms per milliliter (μg/ml) for 50% inhibition of the enzyme activity 2 minutes after zero time.

Results were also expressed as Ki, the micromolar concentration of the inhibitor (μM) giving 50% of the control enzyme activity; or as $k_{obs}/I$ which is the second order rate constant in per mole per second for inactivation of the enzyme.

The elastase activity in the crude PMN extract may vary from one preparation to another. A control of each new batch is run, and the volume added in the assay procedure is adjusted according to activity.

Accordingly, the compounds of Formula (I), Formula A, and Formula A' can be used to reduce inflammation and/or relieve pain in diseases such as emphysema, rheumatoid arthritis, osteoarthritis, gout, bronchial inflammation, chronic or acute bronchitis, cystic fibrosis, adult respiratory distress syndrome, atherosclerosis, sepsis, septicemia, shock, periodontitis, glomerular nephritis or nephosis, myocardial infarction, reperfusion injury, infectious arthritis, rheumatic fever and the like, and may reduce hemorage in acute promyelocytic leukemia and the like.

As appreciated by those of skill in the art, therapy comprising administration of compounds of formula I may actually include co-administration of one or more additional active agents. Classes of active agents include, but are not limited to $\beta_2$-adrenergic agonists; anti-cholinergic agents; steroids; non-steroidal anti-inflammatory agents (NSAID's); mucolytic agents; most all stabilizers; and antibacterials.

For purposes of this specification, $\beta_2$-adrenergic agonists are intended to include, but are not limited to, metaproterenol, terbutaline, isoetharine, albuterol, and ritodrine, carbuterol, fenoterol, quinterenol, rimiterol, salmefamol, soterenol, and tretoquinol.

For purposes of this specification, anticholinergic agents are intended to include, but are not limited to, atropine, and iptratropium-bromide.

For purposes of this specification, mucolytic agents are intended to include, but are not limited to acetylcysteine and guattenesin.

For purposes of this specification, steroids are intended to include, but are not limited to, prednisone, beclomethasone, budesonide, solumedrol, triamcinolone, and methyl-prednisolone.

For purposes of this specification most cell stabilizers are intended to include, but are not limited to cromolyn and ketotafin.

For purposes of this specification, non-steroidal anti-inflammatory agents are intended to include, but are not limited to aspirin, diflunisal, naphthylsalicylate, phenylbutazolone, oxyphenbutazolone, indomethacin, sulindac, mefenamic acid, meclofenamate sodium, tolmetin, ibuprofen, naproxen, fenoprofen and piroxicam.

For the purposes of this specification, antibacterial agents are intended to include the broad classes of penicillins, cephalosporins and other beta-lactams, aminoglycosides, quinolones, macrolides, tetracyclines, sulfonamides, lincosamides and polymyxins. The penicillins, in turn, are intended to include, but are not limited to penicillin G, penicillin V, methicillin, nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams are intended to include, but are not limited to cephalothin, cephapirin, cephalexin, cephradine, cefazolin, cefadroxil, cefaclor, cefamandole, cefotetan, cefoxitin, ceruroxime, cefonicid, ceforadine, cefixime, cefotaxime, moxalactam, ceftizoxime, cetriaxome, ceftizoxime, ceftriaxone, cephoperazone, ceftazidime, imipenem and aztreonam. The aminoglycosides are intended to include, but are not limited to streptomycin, gentamicin, tobramycin, amikacin, netilmicin, kanamycin and neomycin. The quinolones are intended to include, but are not limited to nalidixic acid, norfloxacin, enoxacin, ciprofloxacin, ofloxacin, sparfloxacin and temafloxacin. The macrolides are intended to include, but are not limited to erythomycin, spiramycin and azithromycin. The tetracyclines are intended to include, but are not limited to doxycycline, minocycline and tetracycline. The sulfonamides are intended to include, but are not limited to sulfanilamide, sulfamethoxazole, sulfacetamide, sulfadiazine, sulfisoxazole and co-trimoxazole (trimethoprim/-sulfamethoxazole). The lincosamides are intended to include, but are not limited to clindamycin and lincomycin. The polymyxins (polypeptides) are intended to include, but are not limited to polymyxin B and colistin.

For treatment of inflammation, fever or pain, the compounds of Formula (I), Formula A or Formula A' may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution glucose in water and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I), Formula A and Formula A' may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

The amount of active ingredient that may be combined with the carrier materials to produce a single dosage form will vary depending upon the host treated and the particular mode of administration. For example, a formulation intended for the oral administration of humans may contain from 5 mg to 2000 mg or 5000 mg of active agent compounded with an appropriate and convenient amount of carrier material which may vary from about 5 to about 95 percent of the total composition. For purposes of this specification, this broad dosage range is specifically intended to include, but is not limited to, range of 5 mg to 2000 mg; 25 mg to 2000 mg; 5 mg to 1000 mg; 25 mg to 1000 mg; 5 mg to 500 mg; and 25 mg to 500 mg. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following example illustrates the preparation of the compounds useful in the method of treatment of the present invention, but does not limit the scope of the invention.

EXAMPLE 1

1-p-nitrophenylsulfonyl-4-benzyloxycarbonyl azetidin2-one

Diazabicycloundecane (152 mg, 1 mM) was added to a mixture of 205 mg (1 mM) 4-benzyloxycarbonyl azetidin-2-one and 181 mg (1 mM) p-nitrobenzenesulfonyl chloride in 10 ml methylene chloride at room temperature. After stirring 2½ hours, the orange solution was washed with water, dried over MgSO$_4$, and concentrated in vacuo. The residue was chromatographed on silica gel in hexane/ethyl acetate to yield 64 mg (17%) of 1-p-nitrophenylsulfonyl-4-benzyloxycarbonyl azetidin-2-one.

NMR (CDCl$_3$): δ 3.3 (2H, doublet-quartet), 4.8 (qt. 1H), 5.2 (s, 2H), 7.2 (s, 5H), 8.2 (mlt. 4H).

EXAMPLE 2

1-Acetyl-3,3-dimethyl-4-acetoxyazetidin-2-one

Step A: Preparation of 2-methyl-prop-1-enylacetate

A mixture of 72 g (1M) isobutyraldehyde, 153 g (1.5M) acetic anhydride and 12 g (0.125M) potassium acetate was refluxed seven hours. The cooled reaction mixture was washed with water and stirred with 300 ml saturated $NaHCO_3$ at 0° C. for 45 minutes. The organic phase was dried over $K_2CO_3$ to yield a yellow oil which was distilled at atmospheric pressure to give 35.41 g (31%) of 2-methyl-prop-1-enylacetate, b.p. 122°–126°.

NMR ($CDCl_3$): δ 1.6 (s, 6H), 2.1 (s, 3H), 6.9 (mlt. 1H).

Step B: Preparation of 3,3-dimethyl-4-acetoxyazetidin-2-one

Chlorosulfonyl isocyanate (16 ml) was added to a solution of 22.8 g (0.2M) 2-methyl prop-1-enyl acetate in 50 ml methylene chloride at 0° under nitrogen. After stirring at 0° for 20 hours, the reaction mixture was added to a mixture of 20 ml water, 90 g ice, 48 g $NaHCO_3$ and 16.6 g $Na_2SO_3$ and stirred at 0° for 30 minutes. This was then extracted with 300 ml $CH_2Cl_2$ and the organic phase washed with brine, dried over $MgSO_4$ and concentrated in vacuo to give 27.75 g oil which was chromatograhed on silica gel in hexane/ethyl acetate to yield 2.17 g (8.5%) of 3,3-dimethyl-4-acetoxyazetidin-2-one.

NMR ($CDCl_3$): δ 1.2 (s, 3H), 1.3 (s, 3H), 2.2 (s, 3H), 5.6 (s, 1H).

Step C: Preparation of 1-acetyl-3,3-dimethyl-4-acetoxyazetidin-2-one

A mixture of 283.3 mg (1.8 mM) 3,3-dimethyl-4-acetoxyazetidin-2-one, 2 ml pyridine and 2 ml acetic anhydride was heated to 100° in a sealed tube for 36 hours. The reaction mixture was concentrated in vacuo and the residue chromatographed on silica gel in hexane/ethyl acetate to yield 295 mg (82%) of 1-acetyl-3,3-dimethyl-4-acetoxyazetidin-2-one.

NMR ($CDCl_3$): δ 1.2 (s, 3H), 22 (s, 3H), 2.5 (s, 3H), 6.1 (s, 1H).

EXAMPLE 3

1-Acetyl-4-acetoxy-3-n-propylaztidin-2-one

Step A: Preparation of Pent-1-enyl acetate

A mixture of 86 g (1M) valeraldehyde, 153 g (1.5M) acetic anhydride, and 12 g (0.125M) potassium acetate, was refluxed for 8 hours. The cooled mixture was then stirred with 100 ml saturated aqueous $NaHCO_3$ for one hour. The organic phase is separated, dried over $K_2CO_3$, and distilled at 40 mm to yield 46.15 g (45%) of pent-1-enylacetate, b.p. 89° C.

NMR ($CDCl_3$): δ 1.0 (tr, 3H), 1.2–2.0 (mlt., 4H), 2.1 (s, 3H), 4.7–5.6 (mlt. 1H), 7.0–7.3 (mlt., 1H).

Step B: Preparation of 4-acetoxy-3-n-propylazetidin-2-one

Eight hundred microliters of chlorosulfonyl isocyanate was added to a solution of 1.28 g (10 mM) pent-1-enyl acetate in 5 ml methylene chloride at 0° under nitrogen. After stirring at 0° 5 days, the reaction mixture was added dropwise to a mixture of 5 g ice, 1.15 ml water, 2.82 g $NaHCO_3$ and 1.0 g $Na_2SO_3$ and stirred at 0° for 30 minutes. The mixture was extracted with 2×25 ml methylene choride and the combined organic phases washed with brine, dried over $MgSO_4$, and concentrated in vacuo. The residue was chromatographed on silica gel in hexane/ethyl acetate to yield 60 mg trans 4-acetoxy-3-n-propylazetidin-2-one (3.4%).

NMR ($CDCl_3$): δ 1.0 (mlt., 3H), 1.7 (mlt., 4H), 2.2 (s, 3H), 3.2 (tr, 1H), 5.6 (s, 1H), 6.7 (lrs, 1H).

Step C: Preparation of 1-acetyl-4-acetoxy-3-n-propylazetidin-2-one

A mixture of 56 mg (0.33 mM) 4-acetoxy-3-propylazetidin-2-one, 1 ml acetic anhydride and 1 ml pyridine was stirred at 100° in a sealed tube for 24 hours. After concentrating in vacuo the residue was chromatographed on silica gel in hexane/ethyl acetate, to yield 16 mg (23%) 1-acetyl-4-acetoxy-3-n-propyl-azetidine-2-one.

NMR ($CDCl_3$): δ 1.0 (br tr, 3H), 1.7 (mlt., 4H), 2.2 (s, 3H), 2.4 (s, 3H), 3.2 (tr, 1H), 6.1 (d, 1H).

EXAMPLE 4

1-Acetyl-4-methylsulfonylazetidin-2-one

Step A: Preparation of 1-acetyl-4-methylthioazetidin-2-one

A mixture of 300 mg (2.6 mM) 4-methylthioazetidin-2-one, 10 ml acetic anhydride and 10 ml pyridine was stirred at 100° in a sealed tube 24 hours. After concentrating in vacuo, the residue was chromatographed on silica gel in hexane/ethyl acetate to yield 324 mg (78%) of 1-acetyl-4-methylthioazetidine-2-one.

NMR ($CDCl_3$): δ 2.4 (s, 3H), 2.41 (s, 3H), 3.2 (doublet-quartet, 2H), 5.1 (doublet-doublet, 1H).

Step B: Preparation of N-acetyl-4-methylsulfinylazetidin-2-one

A mixture of 130 mg (0.82 mM) N-acetyl-4-methylthioazetidinone and 200 mg (0.93 mM) 80% m-chloroperbenzoic acid in 5 ml methylene chloride was stirred at room temperature 5 minutes. After removing the solvent in vacuo. The residue was chromatographed on 2–2000µ silica gel plates in hexane/ethyl acetate to yield 57 mg (40%) of 1-acetyl-4-methylsulfinylazetidine-2-one.

NMR ($CDCl_3$): δ 2.4 (s, 3H), 2.6 (s, 3H), 3.5 (mlt., 2H), 4.9 (mlt., 1H).

EXAMPLE 5

3-Azido-4-carboethoxy-1-(p-methoxyphenyl)-azetidin-2-one

To a solution of 3.06 g of azidoacetyl chloride in 50 ml of $CH_2Cl_2$ was added dropwise a solution of 3.57 ml of triethylamine and 5.3 g of the imine formed from ethylglyoxalate and p-anisidine in 50 ml $CH_2Cl_2$, with cooling at such a rate that the reaction temperature remained below 5°. The reaction was then stirred at room temperature for three hours and then washed sequentially with 1N HCl, saturated aqueous sodium bicarbonate, and saturated aqueous sodium chloride. The organic phase was dried over magnesium sulfate, filtered, and evaporated, and the crude residue was recrystallized from carbon tetrachloride/hexane to afford 3.7 g. of 3-azido-4-carboethoxy-1-(p-methoxyphenyl)azetidine-2-one; m.p. 80°–85°.

NMR ($CDCl_3$): δ 7.2 (d, J=9, 2H), 6.75 (d, J=9, 2H), 4.9 (d, J=6, 1H), 4.6 (d, J=6, 1H), 4.25 (q, J=8, 2H), 3.7 (s, 3H), 1.25 (t, J=8, 3H).

EXAMPLE 6

4-Carboethoxy-3-chloro-1-(p-methoxyphenyl)-azetidine-2-one 4-carboethoxy-3-chloro-1-(p-methoxyphenyl)-azetidine-2-one was prepared by following the same procedure as described in Example 5 but using chloroacetyl chloride and the imine formed from ethylglyoxalate and p-anisidine as the starting material. The crude product was recrystallized from ether (hexane) to give 3.1 g of 4-carboethoxy-3-chloro-1-(p-methoxyphenyl)azetidine-2-one, m.p. 99°–100°.

NMR (CDCl$_3$): δ 7.2 (d, J=9, 2H), 6.8 (d, J=9, 2H), 5.1 (d, J=6, 1H), 4 7 (d, J=6, 1H), 4.25 (q, J=7, 2H), 3.7 (s, 3H), 1.25 (t, J=7, 3H).

EXAMPLE 7

4-Carboethoxy-3-methoxy-1-(p-methoxyphenyl)-azetidine-2-one

4-Carboethoxy-3-methoxy-1-(p-methoxyphenyl)-azetidine-2-one was prepared by following the same procedure as described in Example 5 but using methoxyacetyl chloride as the starting material. After chromatography the compound crystallized as a white solid; m.p. 116°–118°.

NMR (CDCl$_3$): δ 7.2 (d, J=9, 2H), 6.75 (d, J=9, 2H), 4.7 (d, J=5, 1H), 4.6 (d, J=5, 1H), 4.2 (q, J=5, 2H), 3.7 (s, 3H), 3.5 (s, 3H), 1.2 (t, J=5, 3H).

EXAMPLE 8

4-Carboethoxy-1-(p-methoxyphenyl)-3-phenyl-azetidin-2-one

To a solution of 17 ml of triethylamine and 5.0 g of the imine formed from ethyl glyoxalate and p-anisidine in 100 ml of refluxing 1,2-dichloroethane was added dropwise over 2 hours a solution of 16 ml of freshly distilled phenylacetyl chloride in 50 ml of dichloroethane. After refluxing for three hours the reaction was worked-up as per the 3-azidoazetidinone. The crude residue was chromatographed to yield the cis and trans isomers of 4-carboethoxy-1-(p-methoxyphenyl)-3-phenylazetidin-2-one as oils; cis: NMR (CDCl$_3$): δ 7.2 (m, 7H), 6.7 (d, J=9, 2H), 4.7 (s, 2H), 3.6 (s, 3H), 3.6 (q, J=7, 2H), 0.7 (t, J=7, 3H); trans: NMR (CDCl$_3$): δ 7.3 (m, 7H), 6.8 (d, J=9, 2H), 4.5 (d, J=2, 1H), 4.45 (d, J=2, 1H), 4.1 (q, J=7, 2H), 3.6 (s, 3H), 1.2 (t, J=7, 3H).

EXAMPLE 9

4-Carboethoxy-1-(p-methoxyphenyl)-3-vinylazetidin-2-one

4-Carboethoxy-1-(p-methoxyphenyl)-3-vinylazetidine-2-one was prepared by following the same procedure as described in Example 8 but using crotonyl chloride as the reagent. After chromatography the cis and trans isomers of the compound were obtained; cis (m.p. 70°–72°), NMR (CDCl$_3$): δ 7.2 (d, J=9, 2H), 6.8 (d, J=9, 2H), 5.2–5.8 (m, 3H), 4.6 (d, J=6, 1H), 4.2 (m, 3H), 3.7 (s, 3H), 1.2 (t, J=7, 3H); trans (oil), NMR (CDCl$_3$): δ 7.25 (d, J=9, 2H), 6.8 (d, J=9, 2H), 5.7–6.2 (m, 1H), 5.2–5.5 (m, 2H), 4.25 (br.s., 1H), 4.2 (q, J=7, 2H), 3.9 (dd, J=1, Jz=6, 1H), 3.75 (s, 1H), 1.25 (t, J=7, 3H).

EXAMPLE 10

4-Carboethoxy-3-ethyl-1-(p-methoxyphenyl)azetidin2-one

The cis and trans isomers of 4-carboethoxy-3-vinyl-1-(p-methoxyphenyl)azetidine-2-one are each hydrogenated with palladium on carbon in ethanol to yield the corresponding cis and trans isomers of 4-carboethoxy-3-ethyl-1-(p-methoxy-phenyl)azetidine-2-one.

EXAMPLE 11

4-Carboethoxy-1-(p-methoxyphenyl)-3-(N-methyl-trifluoroacetamido)azetidin-2-one

A solution of 2.16 g of 3-azido-4-carboethoxy-1-(p-methoxyphenyl)-azetidine-2-one in ethanol was hydrogenated with palladium to yield 4-carboethoxy-1-(p-methoxyphenyl)-3-aminoazetidin-2-one. This amine was acylated with 1.1 ml of trifluoro acetic anhydride in 10 ml CH$_2$Cl$_2$ containing 1.5 ml pyridine, followed by methylation using 1 ml dimethyl sulfate in 30 ml acetone containing 3 g potassium carbonate. After isolation, the crude product was crystallized to give 2.2 g of 4-carboethoxy-1-(p-methoxyphenyl)-3-(N-methyltrifluoroacetamido)-azetidine-2-one, m.p. 102°–104°.

NMR (CDCl$_3$): δ7.2 (d, J=9, 2H), 6.75 (d, J=9, 2H), 5.5 (d, J=6, 1H), 4.7 (d, J=6, 1H), 4.2 (q, J=7, 2H), 3.7 (s, 3H), 3.2 (br.s., 3H), 1.2 (t, J=7, 3H).

EXAMPLE 12

4-Carboethoxy-3-methoxyazetidin-2-one

To a solution of 1.4 g of 4-carboethoxy-3-methoxy-1-(p-methoxyphenyl)azetidine-2-one in 50 ml acetonitrile at 0° was added a solution of 8.23 g of cerric ammonium nitrate in 50 ml H$_2$O over 3 minutes. After stirring at 0° for 1 hour the solution was poured into 200 ml of 10% sodium sulfite and extracted with 3×75 ml of ethyl acetate. The combined organic extracts were washed with 10% sodium sulfite and saturated sodium chloride solutions and dried over sodium sulfate. Filtration and evaporation gave an amber oil which was recrystallized from methylene chloride/hexane to give 700 mg of 4-carboethoxy-3-methoxyazetidine-2-one; m.p. 91°–92°.

NMR (CDCl$_3$): δ7.1 (br.s, 1H), 4.7 (dd, J$_1$=2, J$_2$=5, 1H), 4.3 (d, J=5, 1H), 4.15 (q, J=7, 2H), 3.4 (s, 3H), 1.25 (t, J=7, 3H).

Following substantially the same procedure as described in Example 12 but using an appropriate 3-substituted azetidinone compounds (a)–(f) were prepared:

(a) 4-Carboethoxy-3-chloroazetidin-2-one

NMR (CDCl$_3$): δ 7.3 (br.s., 1H), 5.0 (dd, J$_4$=2, J$_2$=6, 1H), 4.4 (d, J=6, 1H), 4.2 (q, J=7, 2H), 1.3 (t, J=7, 3H).

(b) 4-Carboethoxy-3-phenylazetidin-2-one-2-(cis and trans)

NMR (CDCl$_3$): cis: δ 7.2 (s, 5H), 6.4 (br.s., 1H), 4.7 (d, J=6, 1H), 4.4 (d, J=6, 1H), 3.7 (q, J=7, 2H), 0.75 (t, J=7, 3H); trans: δ 7.2 (s, 5H), 6.9 (br.s, 1H), 4.3 (br.d, J=2, 1H), 4.1 (q, J=7, 2H), 4.0 (d, J=2, 1H), 1.2 (t, J=7, 3H).

(c) 4-Carboethoxy-3-(N-methyltrifluoroacetamido) azetidin-2-one

NMR (CDCl$_3$): δ 7.2 (br.s., 1H), 5.4 (d, J=6, 1H), 4.5 (d, J=6, 1H), 4.15 (q, J=7, 2H), 3.2 (s, 3H), 1.2 (t, J=7, 3H).

(d) 4-Carboethoxy-3-vinylazetidin-2-one(cis and trans)

NMR (CDCl$_3$) cis: δ 7.1 (br.s., 1H), 5.2–5.8 (m, 3H), 4.0–4.4 (m, 4H), 1.25 (t, J=7, 3H); trans: δ=7.25 (br.s., 1H), 5.0–6.2 (m, 3H), 4.1 (q, J=7, 2H), 3.9 (d, J=2, 1H), 3.7 (dd, J$_1$=2, J$_2$=7, 1H), 1.2 (t, J=7, 3H).

(e) 4-Carboethoxy-3-ethylazetidin-2-one

Cis: NMR(CDCl$_3$): δ 6.9 (br. s., 1H); 4.2 (m, 3H); 3.4 (dd, J$_1$=6, J$_2$=8, 1H); 1.51 (q, J=8, 2H); 1.2 (t, J=7, 3H); 1.0 (t, J=8, 3H).

Trans: NMR(CDCl$_3$): δ 6.8 (br. s., 1H); 4.2 (q, J=7, 2H); 3.8 (d, J=2, 1H); 3.2 (dd, J$_1$=2, J$_2$=7, 1H); 1.8 ((dq, J$_1$=2, J$_2$=8, 2H); 1.2 (t, J=7, 3H); 1.0 (t, J=8, 3H).

(f) 3-Azido-4-carboethoxyazetidin-2-one

EXAMPLE 13

4-Carboethoxy-3-(N-methyltrifluoroacetamido)-azetidine-2-one-1-sulfonic acid tetrabutylammonium salt To a solution of 140 mg of 4-carboethoxy-3-(N-methyltrifluoroacetamido)azetidine-2-one in 5 ml of pyridine at 80° was added 250 mg of sulfur trioxide pyridine complex, and the resulting mixture was stirred for 30 minutes at 80°. The solution was poured into 100 ml of 0.5N $KH_2PO_4$ and extracted with 2×25 ml of methylene chloride. The combined organic washes were back-extracted with 25 ml of $KH_2PO_4$ solution. The combined aqueous phases were then treated with 680 mg of tetrabutylammonium hydrogen sulfate and extracted with 3×50 ml of methylene chloride. After drying (sodium sulfate) and evaporation of the organic phase the crude 4-carboethoxy-3-(N-methyltrifluoroacetamido)azetidine-2-one-1-sulfonic acid tetrabutylammonium salt was chromatographed to yield an oil.

NMR ($CDCl_3$): δ 5.3 (d, J=6, 1H), 4.7 (d, J=6, 1H), 4.15 (q, J=7, 2H), 3.2 (m, 11H), 0.8-1.8 (m, 31H).

Applying the same procedure as described above, the following tetrabutylammonium salts of other azetidine derivatives were prepared:

(a) 4-Carboethoxy-3-methoxyazetidin-2-one-1-sulfonic acid tetrabutylammonium salt NMR ($CDCl_3$): δ 4.55 (d, J=6, 1H), 4.5 (d, J=6), 1H), 4.1 (q, J=7, 2H), 3.4 (s, 3H), 3.2 (m, 8H), 0.8-1.8 (m, 31H).

(b) 4-Carboethoxy-3-vinylazetidin-2-one-1-sulfonic acid tetrabutylammonium salt

EXAMPLE 14

4-Carboethoxy-1-(p-nitrobenzenesulfonyl)-3-phenylazetidin-2-one

To a solution of 720 mg of 4-carboethoxy-3-trans-phenylazetidin-2-one in 20 ml methylene chloride at 0° were added sequentially 595 mg of p-nitro-benzenesulfonyl chloride and 0.48 ml of DBU. The solution was stirred for several hours, diluted with 50 ml of methylene chloride, washed once with water and dried over sodium sulfate. Filtration and evaporation gave a crude residue which was chromatographed to yield pure 4-carboethoxy-1-(p-nitrobenzenesulfonyl)-3-phenyl-azetidin-2-one.

NMR ($CDCl_3$): δ 8.3 (d, J=9, 2H), 8.2 (d, J=9, 2H), 7.2 (br.s., 5H), 4.0 (q, J=7, 2H), 3.7 (m, 2H), 1.2 (t, J=7, 3H). Similarly prepared was the corresponding cis-3-phenyl compound. NMR (CDCl3): δ 8.4 (d, J=9, 2H), 8.25 (d, J=9, 2H), 7.2 (s, 5H), 5.0 (s, 1H), 3.7 (m, 3H), 0.85 (t, 5=7, 3H).

Following the same procedure as described above but using appropriate reagents, the following compounds were prepared:

(a) 4-Carboethoxy-1-(p-nitrobenzensulfonyl)-3-vinylazetidin-2-one

NMR ($CDCl_3$):cis: δ 8.3 (d, J=9, 2H), 8.2 (d, J=9, 2H), 5.2-6.0 (m, 3H), 4.0-4.6 (m, 4H), 1.2 (t, J=7, 3H); trans: δ 8.2 (d, J=9, 2H), 8.15 (d, J=9, 2H), 5.2-6.0 (m, 3H), 3.9-4.4 (m, 4H), 1.25 (t, J=7, 3H).

(b) 4-Carboethoxy-3-ethyl-1-(p-nitrobenzenesulfonyl)-azetidin-2-one (c) 3-Azido-4-carboethoxy-1-(p-nitrobenzenesulfonyl)-azetidin-2-one (d) 4-Carboethoxy-3-chloro-1-(p-nitrobenzensulfonyl)-azetidin-2-one

EXAMPLE 15

4-Carboethoxy-3-phenyl-1-trifluoromethanesulfenylazetidin-2-one

To a mixture of 1.2 g of 4-carboethoxy3-phenylazetidin-2-one and 1.2 ml of triethylamine in 25 ml of methylene chloride at 0° was added dropwise over 10 minutes 11.25 ml of a 10% solution of trifluoromethanesulfenyl chloride in ether. After stirring for several hours the solution was washed with water, dried over sodium sulfate, filtered and evaporated. The crude residue was chromatographed to yield pure 4-carboethoxy-3-phenyl-1-trifluoromethanesulfenylazetidin-2-one as an oil.

NMR ($CDCl_3$): δ 7.2 (s, 5H), 4.6 (d, J=3, 1H), 4.3 (m, 3H), 1.3 (t, J=7, 3H).

EXAMPLE 16

1-Tosyloxymethyl-3-n-Propyl-4-p-nitrophenylthioazetidin-2-one

Step A: Preparation of 3-Propyl-4-p-nitrophenylthio azetidin-2-one

3-Propyl-4-acetoxy azetidinone, 171 mg, is refluxed with 200 mg p-nitrophenol thio in 10 ml benzene for 6 hours. The solution is washed 3× with aqueous $Na_2CO_3$, dried with $MgSO_4$, filtered and evaporated. The residue is chromatographed on silica gel, eluting with 10:1 $CHCl_3$-EtOAc, affording 3-propyl-4-p-nitrophenylthioazetidin-2-one.

Step B: Preparation of 1-Tosyloxymethyl-3-n-propyl-4-p-nitrophenylthio azetidin-2-one 3-Propyl-4-p-nitrophenylthioazetidine-2-one, 266 mg, is stirred overnight at room temperature with 0.25 ml aqueous formalin (37%) and 17 mg $K_2CO_3$, Water and formaldehyde are removed in vacuo, and flushed with 2 ml pyridine. The residue is taken up in 4 ml pyridine and treated for 1 hour at room temperature with 200 mg p-toluenesulfonyl chloride. The pyridine is evaporated and replaced with 5 ml benzene. The solution is washed with aqueous $H_3PO_4$ and then aqueous $K_2HPO_4$, dried with $MgSO_4$, filtered and evaporated. The residue is chromatographed on silica gel, eluting with 25:1 $CHCl_3$-EtOAc, providing 1-tosyloxymethyl-3-n-propyl-4-p-nitrophenylthioazetidin-2-one.

EXAMPLE 17

1-Tosyloxymethyl-3-n-propyl-4-p-nitrophenylsulfinylazetidin-2-one

1-Tosyloxymethyl-3-n-propyl-4-p-nitrophenylsulfinylazetidin-2-one, 450 mg, is treated for ½ hour in 10 ml $CH_2Cl_2$ with 172 mg m-chloroperbenzoic acid. The solution is washed with aqueous $K_2HPO_4$, dried with $MgSO_4$, filtered and evaporated, leaving pure 1-tosyloxymethyl-3-n-propyl4-p-nitrophenylsulfinylazetidine-2-one.

EXAMPLE 18

1-Acetoxymethyl-4-p-nitrophenylsulfinyl-3-n-propylazetidin-2-one

Step A: Preparation of 3-n-propyl-4-p-nitrophenylthioazetidin-2-one 3-n-Propyl-4-acetoxyazetidinone (1.164 g, 6.58 mmole) and 1.02 g (6.58 mmole) p-nitrothiophenol were heated in a tube in the steam bath for 3.5 hours. The reaction mixture was cooled, diluted with 100 ml ethyl acetate, and the organic phase was washed with 100 ml water, 70 ml 1M H₃PO₄ and 3×100 ml saturated K₂CO₃. The organic phase was dried over magnesium sulfate, filtered, and solvent removed in vacuo to yield 1.53 g of yellow crystals which were chromatographed on a silica gel column in chloroform-ethyl acetate (4:1) to give 359 mg (19%) of 3-n-propyl-4-p-nitrophenylthioazetidin-2-one.

NMR (CDCl₃): δ 0.92 (tr, 3H), 1.2–1.6 (br m, 4H), 3.10 (tr, 1H), 4.91 (d, 1H), 7.0 (br s, 1H), 7.50 (d, 2H), 8.20 (d, 2H).

Step B: Preparation of 1-Acetoxymethyl-4-p-nitrophenylthio-3-n-propylazetidin-2-one A mixture of 273 mg (0.94 mmole) azetidinone from Step A, 26.3 mg paraformaldehyde and 178 mg (0.56 mmole) cesium carbonate was stirred in 20 ml dry tetrahydrofuran at ambient temperature 16.5 hours under nitrogen. A mixture of 430 μl pyridine and 2.56 ml acetic anhydride was added to the reaction mixture and the stirring continued 5 more hours. The solvents were removed in vacuo to give 604 mg crude product which was chromatographed on a silica gel flash column in hexane-ethyl acetate 3/1. This gave 102 mg (30%) of 1-acetoxymethyl-4-p-nitrophenylthio-3-n-propylazetidin-2-one.

NMR (CDCl₃): δ 1.0 (tr, 3H), 1.2–1.85 (br m, 4H), 2.1 (s, 3H), 3.22 (tr, 1H), 4.95 (d, 1H), 5.18 (ABBA pattern, J₁=30H₃, J₂=5H₃, 2H), 7.65 (d, 2H), 8.22 (d, 2H).

Step C: Preparation of 1-Acetoxymethyl-4-p-nitrophenylsulfinyl-3-n-propylazetidin-2-one To a solution of 46 mg (0.127 mmole) azetidinone from Step B in 4 ml CH₂Cl₂ and 4 ml saturated aqueous NaHCO₃ was added 27 mg (0.127 mM) 80% m-chloroperbenzoic acid and the reaction mixture stirred vigorously 15 minutes. The phases were separated and the organic phase was dried over MgSO₄, filtered and stripped to yield 57 mg crude product which was chromatographed on a 1000μ silica gel prep TLC plate in chloroform-ethyl acetate 4:1 to yield 15 mg (31%) of 1-acetoxymethyl-4-p-nitrophenylsulfinyl-3-n-propylazetidin-2-one.

NMR (CDCl₃): δ 0.93 (tr, 3H), 1.2–1.8 (br m, 4H), 2.1 (s, 3H), 3.55 (tr, 1H), 4.66 (d, 1H), 5.04 (AB pattern, J₁=3.4H_z, J₂=6H_z, 2H), 8.2 (d, 2H), 8.52 (d, 2H).

EXAMPLE 19

4-Acetoxy-3-n-propylazetidin-2-one-1-sulfonic acid tetrabutylammonium salt

A solution of 82 mg (0.463 mmole) 3-propyl-4-acetoxy azetidin-2-one in 5 ml pyridine was heated to 80°. 221 Mg (1.39 mmole) sulfur trioxide-pyridine complex was added and the reaction mixture stirred at 80° one hour. It was then poured into 100 ml 0.5M KH₂PO₄ (aqueous) and washed with 2×25 ml CH₂Cl₂. The combined organic washes were backwashed with 25 ml 0.5M KH₂PO₄. 157 Mg (0.463 mmole) Bu₄N-HSO₄ was added to the combined aqueous phases. This was extracted with 2×25 ml CH₂Cl₂ and the combined extracts were dried over MgSO₄, filtered, and stripped in vacuo to yield 12.4 mg of an oily residue which was chromatographed on a small silica gel column, eluted first with 75 ml hexane/ethyl acetate (3:1) to remove starting material, then with 100 ml ethyl acetate/methanol (4:1) to yield 13 mg (5.7%) 4-acetoxy-3-n-propylazetidin-2-one-1-sulfonic acid tetrabutylammonium salt.

NMR (CDCl₃): δ 1.0 (m, 16H), 1.75 (br m, 20H), 2.16 (s, 3H), 2.90 (br s, H), 3.1 (tr, 1H), 3.3 (tr, 8H), 4.08 (br tr, 1H), 6.18 (s, 1H).

EXAMPLE 20

(3R,4S)-1-(benzylaminocarbonyl)-3-ethyl-3-methyl-4-(4-carboxy)phenoxyazetidin-2-one Step A: Preparation of (3R,4S)-1-t-butyldimethylsilyl-3-methylazetidin-2-one-4-carboxylic acid To a solution of 27.5 ml of diisopropylamine in 150 ml of THF at −20° C. was added 73.5 ml of 2.4N n-butyl lithium in hexane. After 15 minutes, the solution was cooled to −70° C. and a solution of 20 gm of (4S)-1-t-butyldimethylsilylazetidin-2-one-4-carboxylic acid in 75 mL of THF was added. The solution was warmed to −20° C. for 15 minutes before a solution of 13.5 mL of methyl iodide in 20 mL of THF was added. After 30 minutes at −20° to 0° C., the reaction was diluted with 300 mL of ether and then poured into a mixture of ice and 400 mL of 1N HCl. The layers were separated and the aqueous layer extracted with ether. The ether layers were washed with brine, dried over sodium sulfate and evaporated. The residue was crystallized from hexane to give 12–15 gms of (3R,4S)-1-t-butyldimethylsilyl-3-methylazetidin-2-one-4-carboxylic acid.

NMR (CDCl₃): δ 0.14 (2, 3H), 0.32 (s, 3H), 0.91 (d, 3H), 0.98 (s, 9H), 3.34 (dq, 1H), 3.71 (d, 1H)

Step B: Preparation of (3R,4S)-1-t-butyldimethylsilyl-3-ethyl-3-methylazetidin-2-one-4-carboxylic acid To a solution of 13 mL of diisopropylamine in 75 mL of THF at −20° C. was added 35 mL of 2.4M n-butyl lithium in hexane. After 15 minutes the solution was cooled to −70° C. and a solution of 10 gms of (3R,4S)-1-t-butyldimethylsilyl-3-methylazetidin-2-one-4-carboxylic acid in 50 mL of THF was added. The solution was warmed to −20° C. for 15 minutes and a solution of 6.7 mL of ethyl iodide in 10 mL of THF was added. After 30 minutes at −20° to 0° C. the reaction was diluted with ether and poured into a mixture of ice and 1N HCl. The layers were separated and the aqueous layer extracted with ether. The ether layers were each washed with brine, dried over sodium sulfate and evaporated. The residue was crystallized from a minimum amount of hexane to give 8.8 gms of (3R,4S)-1-t-butyldimethylsilyl-3-ethyl-3-methylazetidin-2-one-4-carboxylic acid.

NMR(CDCl₃): δ 0.15 (s, 3H), 0.31 (s, 3H), 0.98 (s, 9H), 1.04 (t, 3H), 1.22 (s, 3H), 1.78 (q, 2H), 3.94 (s, 1H).

Step C: Preparation of (3R, 4S)-3-ethyl-3-methyl-4-(4-carbo-t-butoxy)phenoxyazetidin-2-one To a solution of 13.0 gms of (3R, 4S)-1-t-butyldimethylsilyl-3-ethyl-3-methylazetidin-2-one-4-carboxylic acid in 75 mL of DMF and 15 mL of acetic acid under N₂ was added 23 gms of lead tetraacetate. The reaction was heated at 45°–50° C. for 18 hours and then poured into ice water and extracted into 2 portions of ether. The ether layers were washed with water, dilute sodium bicarbonate solution and brine, dried over sodium sulfate and evaporated to give 13 gm of crude oil containing a mixture of (3R, 4S) and (3R, 4R)-4-acetoxy-3-ethyl-3-methylazetidin-2-one. To this mixture in 50 mL of acetone was slowly added a solution of 14 gms of t-butyl 4-hydroxybenzoate in 50 mL of acetone, 5 mL of water and 29 mL of 2N sodium hydroxide. The reaction was stirred at room temperature for 64 hours and then diluted with water and extracted with 2 portions of ether. The ether layers were washed with brine, dried over sodium sulfate and evaporated. The residue was prep LC'ed with 15-25% ethylacetate/hexanes to give 6.3 gm of the higher $R_f$(4R) ether and 1.5 gm of the desired (3R, 4S)-3-ethyl-3-methyl-4-(4-carbo-t-butoxy)-phenoxyazetidin-2-one.

NMR (CDCl$_3$): δ 1.0 (t, 3H), 1.38 (s, 3H), 1.54 (s, 9H), 1.6–2.0 (m, 2H), 5.30 (s, 1H) 6.7 (brs, 1H), 6.78 (d, 2H), 7.90 (d, 2H).

Step D: Preparation of (3R, 4S)-1-(benzylaminocarbonyl)-3-ethyl-3-methyl-4-(4-carbo-t-butoxy)phenoxyazetidin-2-one To a solution of 1.5 gm of (3R, 4S)-3-ethyl-3-methyl-4-(4-carbo-t-butoxy)phenoxyazetidin-2-one in 25 mL of methylene chloride was added 1.2 mL of benzylisocyanate, 1.4 mL of triethylamine and 10 mg of 4-dimethylaminopyridine. The reaction was stirred at room temperature for 16 hours and then evaporated. The residue was flash chromatographed eluting with 10 to 25% EtOAc/Hexane to give 2.3 gm of (3R, 4S)-1-(benzylaminocarbonyl)-3-ethyl-3-methyl-4-(4-carbo-t-butoxy)phenoxy azetidin-2-one.

NMR (CDCl$_3$): δ 0.98 (t, 3H), 1.36 (s, 3H), 1.50 (s, 9H), 1.62 (m, 1H), 1.84 (m, 1H), 4.42 (d, 2H), 5.64 (s, 1H), 6.80 (brt, 1H), 7.06 (d, 2H), 7.24 (brs, 5H), 7.90 (d, 2H).

Step E: Preparation of (3R, 4S)-1-(benzylaminocarbonyl)-3-ethyl-3-methyl-4-(4-carboxy)phenoxyazetidin-2-one To 2.3 gm of (3R, 4S)-1-(benzylaminocarbonyl)-3-ethyl-3-methyl-4-(4-carbo-t-butoxy) phenoxyazetidin-2-one in an ice bath under N$_2$ was added 5 mL of anisole and then 25 mL of precooled trifluoroacetic acid. After 1.5 hours at 0° C., the volatiles were removed in vacuo without heating and the residue flash chromatographed using hexane, then 15% EtoAc/Hexane, then 1% HoAc in 15% EtoAc/hexanes to give after ether trituration 1.8 gm of (3R, 4S)-1-(benzylaminocarbonyl)-3-ethyl-3-methyl-4-(4-carboxy)phenoxyazetidin-2-one.

NMR (CDCl$_3$): δ 1.03 (t, 3H), 1.46 (s, 3H), 1.66 (m, 1H), 1.94 (m, 1H), 4.50 (d, 2H), 5.76 (s, 1H), 6.9 (brt, 1H), 7.05 (d, 2H), 7.25 (brs, 5H), 7.98 (d, 2H).

EXAMPLE 21 t-Butyl 4-hydroxy-phenylacetate

A solution of H$_2$SO$_4$ (5 ml) in dioxane (80 ml) was added to 4-hydroxyphenylacetic acid (20 gm, 0.13 mol) in a pressure bottle. Isobutylene (250 ml) was added and the bottle was sealed and the mixture was stirred for 24 hr. The reaction mixture was poured into saturated NaHCO$_3$ solution and extracted with EtOAc. The combined organic extracts were washed successively with saturated NaHCO$_3$, H$_2$O (twice) and brine before being dried over Na$_2$SO$_4$ and evaporated to dryness. Crystals formed after standing overnight and they were filtered, washed with cold hexane and dried to give 20.99 gm of the title compound. M.pt. 95°–96° C.

NMR: δ1.45 (s, 9H), 3.45 (s, 2H), 4.60 (brs, 1H), 6.72 (d, 2H), 7.10 (d, 2H).

EXAMPLE 22

(R,S)-3,3-Diethyl-4-[(4-t-butoxycarbonylmethyl)-phenoxy]azetidin-2-one

Step A: Preparation of 1-acetyloxy-2-ethyl-1-butene

A solution of 2-ethylbutyraldehyde (600 gm, 5.99 mol), acetic anhydride (900 ml, 8.15 mol) and sodium acetate (61.5 gm) was heated to reflux under N$_2$ atmosphere. After 2 days the reaction was poured into a mixture of CH$_2$Cl$_2$ (1 liter), H$_2$O (1 liter) and ice (500 gm). The solution was neutralized by adding solid Na$_2$CO$_3$ and the layers were separated. The aqueous layer was further extracted with CH$_2$Cl$_2$ and the pooled organic layers were washed with saturated NaCl, dried over Na$_2$SO$_4$ and evaporated to dryness. Distillation of the residue in vacuo gave 464.5 gm of the title compound.

Step B: Preparation of 4-acetyloxy-3,3-diethylazetidin-2-one

A solution of the material prepared in Step A (169 gm, 1.19 mol) in CH$_2$Cl$_2$ (300 ml) was cooled in an ice-ethanol bath under N$_2$ and chlorosulfonyl isocyanate (200 gm, 1.41 mol) was added via an addition funnel. The solution was allowed to rise to room temperature and stirred overnight. The reaction mixture was then diluted with Et$_2$O and added to ice-cold NaHCO$_3$ solution containing Na$_2$SO$_3$, keeping the solution below 5° C. during the addition. After the evolution of gas had ceased, the layers were separated and the aqueous layer was extracted with Et$_2$O. The combined ether extracts were washed with H$_2$O, brine and then dried over Na$_2$SO$_4$ before being evaporated to dryness. This gave a dark oil which was diluted with hexane (100 ml) and cooled in the freezer for 2 days. The low melting white solid which formed was filtered off and washed with cold hexane to give 79.2 gm of the title compound.

NMR: δ 0.99 (t, 3H), 1.02 (t, 3H), 1.72 (m, 4H), 2.13 (s, 3H), 5.58 (s, 1H), 6.40 (brs, 1H).

Step C: Preparation of (R,S)-3,3-diethyl-4-[(4-t-butoxycarbonylmethyl)-phenoxy]azetidin-2-one Material prepared in Example 21 (20.8 gm, 0.1 mol) was dissolved in 2N NaOH (100 ml) by stirring for 15 min. and a solution of the material prepared in Step B above (18.5 gm, 0.1 mol) in toluene (100 ml) and hexane (100 ml) was added. The reaction mixture was vigorously stirred for 1 hr and then the layers were separated and the aqueous layer was extracted with EtOAc. The organic layer was washed with water, brine and dried over Na$_2$SO$_4$ before being evaporated to dryness. The residue so obtained was purified by preparative LC using 20% EtOAc-hexane to give 17.5 gm of the title compound.

NMR: δ 1.00 (t, 3H), 1.05 (t, 3H), 1.43 (s, 9H), 1.71–2.00 (m, 4H), 3.46 (s, 2H), 5.32 (s, 1H), 6.74 (brs, 1H), 6.82 (d, 2H), 7.20 (d, 2H).

EXAMPLE 23

Benzyl 4-hydroxy-phenyl acetate

To a solution of 4-hydroxyphenylacetic acid (3.969 Kg, 26.09 mol) in DMF (15.9 L) was added lithium carbonate (2.12 Kg, 28.7 mol) and the resulting mixture was stirred at room temperature for 10 minutes. Benzyl bromide (3.723 L, 31.3 mol) was added and the mixture was heated to 100° C. (internal temperature) for 3 hours. The reaction was cooled to 60° C., 2N HCl (20 L) was added and the solution was extracted with EtOAc (2×10 L). The combined organic extracts were washed successively with saturated NaHCO$_3$ (16 L) and H$_2$O (3×16 L). Any emulsions formed during these extractions were broken up by the addition of toluene (20 L total). The EtOAc was removed by distillation until the level of EtOAc was <0.3% (additional toluene (5 L) was added during distillation). The volume of the mixture was reduced to 16 L and allowed to cool to room temperature when crystallization occurred. The slurry was diluted with hexane (20 L) and aged at ambient temperature overnight, before being cooled to 0° C. The solid was filtered, washed with a cold mixture of toluene/hexane (1:1, 4 L) and dried in vacuo to give 5.283 Kg of the required product.

EXAMPLE 24

(R,S)-3,3-Diethyl-4-[(4-benzyloxycarbonylmethyl)-phenoxy]azetidin-2-one

Method A:

Step A: Preparation of 1-propionyloxy-2-ethyl-1-butene

A reaction vessel was charged sequentially with $Et_3N$ (12.8 L), propionic anhydride (14.48 L), dimethylaminopyridine (94 gm) and 2-ethylbutyraldehyde (7.5 L). The mixture was stirred and heated under gentle reflux (120°–135° C.) for 5 hours in a nitrogen atmosphere. The reaction was then cooled to 70° C. and $H_2O$ (13.5 L) was added slowly. On complete addition, the mixture was heated at reflux for 45 minutes and then cooled to room temperature before hexane (7.5 L) was added. The aqueous layer was separated and re-extracted with hexane (5 L) and the combined organic layers were washed with saturated $NaHCO_3$ (2×7.5 L) before being evaporated in vacuo at 40° C. The residue (10 Kg) so obtained was fractionally distilled (b.p. 75°–80° C., 30–40 mm Hg) to give the required product (7.712 Kg) as a mobile liquid.

Step B: Preparation of 4-propionyloxy-3,3-diethylazetindin-2-one

The product (2.5 Kg) prepared as described above in Example 24, Method A, Step A, was dissolved in nitromethane (1.25 L) and the solution was allowed to cool to −2° C. overnight. Chlorosulfonyl isocyanate (2.1 L) was added over 30 minutes, maintaining the temperature below 6° C. On complete addition, the yellow solution was cooled to 0° C. and stored under a nitrogen atmosphere for 30 hours. The reaction mixture was then diluted with $Et_2O$ (4 L) and then added slowly over 30 minutes to a mixture of $H_2O$ (70 L), $Na_2SO_3$ (7.5 Kg) and $NaHCO_3$ (12.5 Kg) at 5° C., maintaining the temperature below 5° C. throughout the addition. An additional 2.5 L of $Et_2O$ was used for washing-in. The reaction wa then allowed to rise to 15° C. over 1 hour, after which time gas evolution had ceased. The reaction mixture was then filtered and rinsing was carried out with $H_2O$ (10 L) and t-butylmethylether (15 L). The lower layer was separated and and further extracted with t-butylmethylether (15 L). The combined organic extracts were washed with brine (20 L), dried over $Na_2SO_4$, filtered and evaporated to dryness (temperature below 35° C. to give the product (2.64 Kg) as a yellow oil suitable for use in the next step.

Step C: Preparation of (R,S)-3,3-diethyl-4-[(4-(benzyloxycarbonylmethyl)phenoxy]azetidin-2-one A solution of benzyl 4-hydroxy-phenyl acetate (2.68 Kg, 11.07 mol, prepared as described above in Example 23) in toluene (65 L) was heated at 40° C. until a solution was obtained and $Ba(OH)_2.8H_2O$ (4.20 Kg, 13.31 mol) was then added. This slurry was stirred at 40° C. for 10 minutes and then a solution of 4-propionyloxy-3,3-diethylazetidin-2-one (2.57 Kg, 11.73 mol, prepared as described above in Example 24, Step B) in toluene (10 L) was added over 15 minutes. After 1.5 hours a second portion 4-propionyloxy-3,3-diethylazetidin-2-one (70 gm) was added. After an additional 30 minutes the mixture was cooled to 15° C. and 2N HCl (30 L) was added. The organic layer was washed successively with saturated $NaHCO_3$ (2×30 L) and brine (20 L), and then was concentrated in vacuo to give 3.805 Kg of the product as a viscous yellow oil.)

Method B:

Step A: Preparation of 1-(2-ethylpropionyloxy)-2-ethylbutene 2-Ethylbutyric anhydride (4.34 L), 2-ethylbutyraldehyde (2.28 L), triethylamine (2.62 L), and 4-dimethylaminopyridine (210 g) were mixed and stirred under a $N_2$ blanket and the temperature was successively raised to 120° C. over 1.5 hr, then 140° C. over 8 hr, followed by maintenance at 140° C. for 10 hr. The mixture was then cooled to 90° C., $H_2O$ (2 L) was added and the mixture was then heated at reflux for 1 hr before being allowed to cool to 25° C. To this material was then added $H_2O$ (2 L) and hexanes:EtOAc (3:1; 3 L) and, after mixing, the layers were separated and the organic layer was washed successively with cold 2N HCl (3 L) and sat. $NaHCO_3$ (3×2 L) before being concentrated in vacuo and then flushed with EtOAc (500 mL). This afforded 3.7 kg of crude product which was purified by distillation (b.p. 80° C./1 mm Hg) to give 3.3 kg of the title compound as a clear colorless oil.

Step B: Preparation of 3,3-diethyl-4-(2-ethylpropionyloxy)-azetidin-2-one

The material prepared above in Example 24, Method B, Step A (3.3 kg) was cooled to 5° C. under a $N_2$ blanket and chlorosulfonyl isocyanate (2.1 L) was added with stirring over 1 hr. The mixture was then stirred at 8° C. for 45 hr and then cooled to 0° C., diluted with toluene (5 L), and then added to a mixture of $H_2O$ (60 L), ice (20 L), $NaHCO_3$ (13 kg) and $Na_2SO_3$ (7.5 kg). This mixture was stirred at 20° C. for 13 hr before being filtered through Celite. The pad was washed with EtOAc (7 L) and the two layers of the filtrate were separated. The aqueous layer was further extracted with EtOAc (12 L) and the combined organic layers were washed with brine (8 L) before being concentrated in vacuo. Toluene (2 L) was then added to the residue and the solution was re-concentrated to dryness to give 4.57 kg of a light yellow oil which was of sufficient purity for use in the next step.

Step C: Preparation of (R,S)-3,3-diethyl-4-[(4-benzyloxycarbonylmethyl)phenoxy]-azetidin-2-one Benzyl 4-hydroxyphenylacetate (2.6 kg) was dissolved in DMF (20 L) and $H_2O$ (2.8 L) and milled $K_2CO_3$ (4.5 kg) were added. To this mixture (at 35° C.) was added the material prepared above in Example 24, Method B, Step B (3.15 kg of β-lactam). The resulting mixture was cooled and stirred at 30°–31° C. for 1 hr, followed by stirring at 18° C. for an additional hr before being quenched by the addition of 2N HCl (15 L) and EtOAc (15 L). The layers were separated and the aqueous phase (pH 8.2) was further extracted with EtOAc (18 L). The combined organic layers were washed successively with sat. $NaHCO_3$ (13 L), $H_2O$ (10 L), and brine (10 L) before being concentrated in vacuo to afford the title compound as a yellow-orange oil (5.4 kg) which was of sufficient purity for use in the next step.

Method C:

A solution of the material prepared in Example 24, Method A, Step B (2.2 gm, 11.9 mmol), benzyl 4-hydroxyphenylacetate (2.93 gm, 12.1 mmol), cinchonin (0.35 gm, 1.2 mmol) and powdered anhydrous $Na_2CO_3$ (1.28 gm, 12.1 mmol) in toluene (25 ml) was heated to 60° C. for 72 hr. After cooling, EtOAc (100 ml) was added and the solution was washed successively with 1N HCl (3×25 ml), sat. $NaHCO_3$ solution (25 ml), $H_2O$ (25 ml), and brine (25 ml). The solution was then dried over Na$_2$SO$_4$, filtered and evaporated to dryness to give a clear, yellow oil which was purified by flash chromatography (silica gel, 25% EtOAc in hexanes) to give the title compound as a slightly yellow oil (3.05 gm). [α]$_D$ −23.70 NMR (CDCl3): δ 1.08 (t, 3H), 1.12 (t, 3H), 1.64-2.14 (m, 4H), 3.48 (s, 2H), 5.18 (s, 2H), 5.38 (s, 1H), 6.90 (d, 2H), 7.28 (d, 2H), 7.40 (s, 5H).

EXAMPLE 25

(R,S)-3,3-Diethyl-4-[(4-carboxymethyl)phenoxy]-azetidin-2-one (R,S)-3,3-Diethyl-4-[(4-benzyloxycarbonylmethyl)-phenoxy]azetidin-2-one (5.24 Kg, (14.26 mol) prepared as described above in Example 24, Method A was dissolved in alcohol (34.5 L) and cyclohexene (10.5 L) containing 10% PdC (524 gm). The mixture was stirred and heated under reflux for 3 hours and then allowed to cool to room temperature before being filtered through Whatman GFA paper to remove the catalyst. The pad was washed with EtOAc and the combined filtrates were evaporated to dryness to give a viscous oil. This was partitioned between 10% aq. K$_2$CO$_3$ (6 L) and EtOAc (7 L) and the lower layer was re-extracted with EtOAc (7 L). The aqueous layer was acidified with 5N HCl (N4.8L) and extracted with EtOAc (10 L). The lower aqueous layer was separated and re-extracted with EtOAc (7 L). The pooled organic layers were washed with H$_2$O (5 L), dried over Na$_2$SO$_4$, filtered and evaporated in vacuo to give a viscous oil which solidified upon storage in the cold room giving 3.55 Kg of the required product.

EXAMPLE 26

(S)-3,3-Diethyl-4-[(4-carboxymethyl)phenoxy]azetidin-2-one, (S)-(−)-α-methylbenzylamine salt The racemate (253.3 gm, 0.91 mol) prepared as described above in Example 25 was dissolved in EtOAc (1.27 L) and (R)-(+)-α-methylbenzylamine (117.7 mL, 0.91 mol) was added followed by a seed crystal of (R)-3,3-diethyl-4-[(4-(carboxymethyl)phenoxy]azetidin-2-one, (R)-(+)-α-methylbenzylamine salt. This mixture was stirred at room temperature overnight and then chilled to 0°-5° C. for 1 hour, filtered, washed with a little cold EtOAc and dried in air. This material was swished in EtOAc (1.2 L) at 60° C. for 1 hour and then cooled to 0°-5° C. for 1.5 hour, filtered and washed with a little fresh solvent. All of the filtrates and the swish were combined and washed successively with 2N HCl (3×350 mL) and brine (1×350 mL). The organic layer was dried (Na$_2$SO$_4$), filtered and evaporated to give a viscous oil (187 gm). This oil was dissolved in EtOAc (935 mL) and treated with (S)-(−)-α-methylbenzylamine as described above for the crystallization of the unwanted isomer with (R)-(+)-α-methylbenzylamine. This gave 119.84 gm of the desired (S)-3,3-diethyl-4-[(4-carboxymethyl)-phenoxy]azetidin-2-one, (S)-(−)-α-methylbezylamine salt with an enantiomeric purity 98%. Reworking of the mother liquors gave an additional 18.8 gm (i.e. total yield of 138.64 gm).

EXAMPLE 27

(S)-3,3-Diethyl-4-[(4-benzyloxycarbonylmethyl)-phenoxy]azetidin-2-one

The resolved material prepared as described above in Example 26, (3.35 Kg, 8.41 mol) was partitioned between EtOAc (21 L) and 2N HCl (4.2 L), with stirring for 15 min. The organic layer was washed successively with 2N HCl (2×4.2 L) and H$_2$O (2×5 L) and then dried over Na$_2$SO$_4$, filtered and evaporated to dryness to give 2.36 Kg of the resolved acid. This oil was dissolved in DMF (11.8 L) and stirred overnight with ground K$_2$CO$_3$ (698 gm, 5.05 mol) and benzyl bromide (1.02 L, 8.57 mol) at room temperature. Water (26 L) was then added and the mixture was extracted with t-butylmethyl ether (14 L). The lower layer was re-extracted with t-butylmethyl ether (14 L) and the combined organic layers were washed with H$_2$O (2×10 L), dried (Na$_2$SO$_4$), filtered and evaporated to dryness to give the product (2.87 Kg) as a viscous oil. [α]$_D$= −60.8° (c=1.0, 1,1,1-trichloroethane).)

EXAMPLE 28

(R)-α-Allyl-4-methylbenzyl isocyanate

Method A:

Step A: Preparation of (R)-α-allyl-4-methylphenyl-benzylamine, L-pyroglutamic acid salt A solution of lithium bistrimethylsilylamide was prepared as follows. To hexamethyldisilazane (4.04 Kg, 5.28 L, 25 mol) was added anhydrous THF (4 L). The solution was cooled to −5° C. and n-BuLi (2.4M in hexanes, 9.7 L) was added over a period of 1.5 hr, while maintaining the reaction temperature between −5° and 0° C. The mixture was then aged for 10–15 min, allowed to rise to room temperature and stored under N$_2$ overnight.

A solution of p-tolualdehyde (2.91 Kg, 24.27 mol) in THF (10 L) was cooled under N$_2$ to −8° C. and the solution of lithium bistrimethylsilylamide prepared above was added via an addition funnel, while maintaining the reaction temperature between −8° and 0° C. The mixture was then warmed to 10° C. and allylmagnesium chloride (2M, 12.5 L, 25 mol) was added, while maintaining the temperature between 15°-20° C. After aging for 15 min the reaction mixture was cooled to 10° C. and transferred to a larger vessel containing H$_2$O (85 L) and NH$_4$Cl (12 Kg) at 10° C. An additional 5 L of THF was used to complete the transfer and the quench mixture exothermed to 25° C. during the transfer. After stirring for 30 min the lower aqueous layer separated and was removed. The organic layer was washed with brine (20 L) and then the bulk solvent was removed in vacuo at 30°-35° C. and the remaining solution (8–10 L) was dried over Na$_2$SO$_4$, filtered and evaporated to dryness to give the product racemic amine in quantitative yield.

This racemate (3.95 Kg, 23.8 mol) was dissolved in EtOAc (40 L) and this solution was added to a solution (warming to 50° C. was necessary to effect complete dissolution) of L-pyroglutamic acid (1.84 Kg, 14.26 mol) in methanol (8 L). The mixture was heated to reflux and solvent (20 L) was distilled from the vessel. EtOAc (30 L) was added and more solvent (30 L) was distilled off. A further charge of EtOAc (40 L) was added and the reaction mixture was concentrated to 39 L. The mixture was allowed to cool to 65° C. and seeded before being allowed to cool further (to 50° C. over 30 min) to form a thick slurry. The slurry was then reheated to reflux and aged for 30 min. After cooling to room temperature over 1 hr, and further aging at 15° C. for 1 hr, the amine salt was filtered, washed with EtOAc (3 L) and dried in vacuo at 50° C. This material was recrystallized from EtOAc (23 L), filtered, washed succesively with EtOAc (2×2 L) and Et$_2$O (1 L) and then dried in vacuo overnight at 50° C. to give the title amine salt with an R:S ratio (GC of menthyl carbamate derivatives) of 95:5.

Step B: (R)-α-Allyl-4-methylbenzyl isocyanate

The amine salt prepared above in Example 28, Method A, Step A (2.655 Kg) was dissolved in a mixture of t-butylmethyl ether (7.38 L) and H$_2$O (7.38 L) and 5M NaOH (3 L) was added. This mixture was stirred for 15 min and the aqueous layer was separated and re-extracted with t-butylmethyl ether (7.38 L). The pooled orgnaic extracts were washed with brine (2×4 L), dried (Na$_2$SO$_4$), filtered and evaporated to dryness to give the free amine (1.5 Kg) as a mobile liquid. This material was dissolved in EtOAc (8.86 L) and cooled to 0°–5° C. and to this was added a solution of EtOAc/HCl (prepared separately by adding absolute EtOH (1.062 L) dropwise over 50 min to an ice cold solution of acetyl chloride (1.298 L) in EtOAc (3.54 L), while maintaining the temperature below 10° C. during the addition) dropwise over 50 min, maintaining the temperature below 20° C. The resulting amine hydrochloride slurry was heated to 70° C. and a solution of 1.93M phosgene in toluene (11 L, 21.1 mol) was added over 1.75 hr at this temperature. The resulting solution was heated at 70° C. for a further 1.75 hr and then cooled to room temperature. A mixture of brine (6 L) and H$_2$O (6 L) was added and the mixture allowed to separate. The organic phase was washed successively with saturated NaHCO$_3$ solution (2×10 L) and brine (10 L) before being dried over Na$_2$SO$_4$, filtered and evaporated to dryness to give the title compound as a mobile liquid.

Method B:

Step A: Preparation of (R)-α-allyl-4-methylbenzylamine

A solution of lithium bistrimethylsilylamide was prepared by adding 208 ml of 2.5M n-BuLi to a solution of bistrimethylsilylamine (110 ml, 0.52 mol) in THF (140 ml) at 0° C. After stirring for 15 min, this solution was added via a cannula to a solution of p-tolualdehyde (59 ml, 0.5 mol) in THF (100 ml), while keeping the temperature between −40° and −50° C. The reaction mixture was then allowed to warm up to 10° C. over 30 min. A 2M solution of allyl magnesium chloride (260 ml) in THF was added, keeping the temperature of the reaction between 10° and 15° C. After stirring for 30 min the reaction was poured into a solution prepared by dissolving NH$_4$Cl (150 gm) in H$_2$O (1 liter). The layers were separated and the aqueous layer was extracted with Et$_2$O-hexane. The organic layer was washed with brine, dried over Na$_2$SO$_4$ and evaporated to dryness. The residual oil was added to a solution of (1R)-(−)-10-camphorsulfonic acid (62.5 gm) in EtOAc (1 liter) with cooling. On standing overnight at room temperature, crystals were formed and these were filtered off and washed with EtOAc. The solid was stirred with refluxing EtOAc (300 ml), filtered and washed again with EtOAc. The pure product so formed weighed 60.7 gm (59%). [α]$_D$ −27.16 (c=0.5, EtOH).

Step B: (R)-α-allyl-(4-methylphenyl)methyl isocyanate

A slurry of 50 gm (0.122 mol) of material prepared as described above in Step A was added to 2N NaOH (75 ml) and Et$_2$O (150 ml). After stirring for 5 min the layers were separated and the aqueous layer was extracted with Et$_2$O. The pooled organic layers were washed with brine, dried over Na$_2$SO$_4$, filtered and evaporated to dryness.

A 3-necked flask equipped with a gas inlet tube, a condenser, and an addition funnel without sidearm was charged with EtOAc (100 ml) and this was heated on a 60° C. bath while phosgene gas was bubbled through the solution. A solution of the amine obtained above in 20 ml of EtOAc was added dropwise at a rate such that the white solid did not build up in the reaction mixture. Phosgene was continued for 5 additional minutes after all the amine had been added and the solution was clear. The bath was then heated to 110° C. and EtOAc was removed by distillation. The title compound was so obtained as a yellow residue (24.99 gm) and was used without further purification.

EXAMPLE 29

(4S)-3,3-Diethyl-1-[(R)-α-n-propyl-(4-methyl)benzylaminocarbonyl]-4-[4-(carboxymethyl)phenoxy]azetidin-2-one Step A: Preparation of (4S)-3,3-Diethyl-1-[(R)-α-allyl-(4-methyl)benzylaminocarbonyl]-4-[4-(benzyloxycarbonylmethyl)phenoxy]azetidin-2-one To a vessel charged with DMF (14.23 L) was added the material prepared above in Example 27 (2.845 Kg, 7.74 mol) and the material prepared above in Example 28, Method A (8.17 mol). Ground, anhydrous K$_2$CO$_3$ (108 gm, 0.78 mol) was added and the resulting mixture was stirred at room temperature, under N$_2$, for 2.5 hr. The reaction mixture was then diluted with EtOAc (25 L) and stirred with H$_2$O (25 L) for 5 min. The layers were separated and the organic layer was washed with H$_2$O (25 L). An emulsion formed which was broken up by the addition of saturated brine (5 L) and the organic layer was further washed with H$_2$O (2×20 L). Again emulsions were formed and this time they were broken up by the addition of t-butylmethyl ether (10 L). The organic layer was finally washed with brine (10 L) and then concentrated in vacuo to 12 L, dried over Na$_2$SO$_4$, filtered and evaporated to dryness to give the title compound as a viscous orange oil which was suitable for use in the next step.

Step B: (4S)-3,3-Diethyl-1-[(R)-α-n-propyl-(4-methyl)benzylaminocarbonyl]-4-[4-(carboxymethyl)phenoxy]azetidin-2-one, isobutanolamine salt The material prepared above in Example 29, Step A (1.547 Kg), was dissolved in a mixture of t-butanol (7.347 Kg) and H$_2$O (387 mL) containing 10% Pd/C (150 gm) and hydrogenated at 50 psi for 1 hr at 20° C. The mixture was then filtered through Hyflo and the pad was washed with EtOAc. The filtrate was evaporated to dryness to give the title compound (free acid) as a viscous oil in essentially quantitative yield. Two more runs gave a total of 4.2 Kg of crude free acid (estimated 3.5 Kg of desired material by LC and NMR analysis) which was dissolved in t-butylmethyl ether (50 L) at room temperature. A solution of 2-amino-2-methyl-1-propanol (670 gm) in t-butylmethyl ether (13 L) was added over 20 min at room temperature. The solution was seeded and the resulting slurry was stirred at room temperature overnight. The mixture was then chilled at 0° C. for 1 hr, filtered, washed with t-butylmethyl ether (12 L) and dried in vacuo at room temperature. This product was recrystallized twice from EtOAc to give the title compound (3.159 Kg) as a crystalline white powder. m.p. 138.5°–140° C.

EXAMPLE 30

(S)-3,3-Diethyl-4-[(4-allyloxycarbonylmethyl)-phenoxy]azetidin-2-one

Method A:

The resolved material prepared above in Example 26, (19.9 gm, 0.05 mol) was added to a mixture of ice-H₂O (300 mL), conc. HCl (5 mL), and Et₂O and mixed thoroughly until dissolution occured. The layers were separated and the aqueous layer was extracted with Et₂O. The pooled Et₂O layers were washed successively with H₂O and sat. NaCl before being dried over Na₂SO₄, filtered and evaporated to dryness. This residual oil was dissolved in DMF (100 mL) and powdered K₂CO₃ (7.1 gm, 0.051 mol) was added, followed by allyl bromide (4.6 mL, 0.053 mol). This mixture was stirred overnight at room temperature and was then partitioned between H₂O and Et₂O. The layers were separated and the aqueous layer was extracted with Et₂O. The pooled Et₂O layers were washed with H₂O (2×) and sat. NaCl before being dried over Na₂SO₄, filtered and evaporated to dryness to give 17.0 gm (0.05 mol, quantitative yield) of the title compound suitable for use in the next step.

NMR (CDCl₃, δ from TMS): 1.03 (t, 3H, J=7 Hz), 1.06 (t, 3H, J=7 Hz), 1.65-2.05 (m, 4H), 3.60 (s, 2H), 4.59 (d of t, 2H, J=6 Hz, J=1 Hz), 5.2-5.4 (m, 2H), 5.34 (s, 1H), 6.57 (br s, 1H), 6.82 (m, 2H), 7.27 (m, 2H)

EXAMPLE 31

(R)-5-[(1-Isocyanate)butan-1-yl]benzofuran

Step A: Preparation of (4-Bromo-2-formyl)phenoxyacetic acid, monohydrate

To a solution of 5-bromosalicylaldehyde (5 kg) in THF (12.1 L) at 40° C. under a N₂ blanket was added a solution of bromoacetic acid (3.8 kg) in H₂O (50 L). This mixture was stirred at 40° C. and a solution of NaOH (2.09 kg) in H₂O (8.1 L) was added over 20 min. The deep red solution so formed was warmed to gentle reflux for 18 hr. THF (approx. 7 L) was then distilled from the reaction mixture at atmospheric pressure and the resultant yellow solution was cooled to room temperature. The pH was then adjusted to 8±0.2 by the addition of sat. NaHCO₃ solution and the resultant mixture was extracted with isopropylacetate (2×15 L). The aqueous layer was acidified to pH 3±0.2 with conc. HCl (2.4 L) and the resultant slurry was aged at 20° C. for 1 hr and the product was then filtered off, washing the pad with H₂O (7 L) to give the title compound as a pale yellow solid (3.77 kg).

Step B: Preparation of 5-bromobenzofuran

A slurry of the material prepared above in Example 31, Step A (3.70 kg) and sodium acetate (7.40 kg) in acetic acid (18.5 L) was heated to gentle reflux under a N₂ blanket and acetic anhydride (7.4 L) was then added dropwise over 6 hr. This mixture was then heated at reflux until HPLC indicated no remaining starting material. The reaction was then cooled to 80° C. and H₂O (11.1 L) was added dropwise over 1 hr. The mixture was then reheated to gentle reflux for 1 hr, cooled to 25° C., and transferred to a separating funnel. H₂O (15 L) and hexane (15 L) were added and the phases separated. The lower layer was re-extracted with hexane (15 L) and the combined organic extracts were washed successively with H₂O (2×10 L) and sat. NaHCO₃ (15 L) before being dried over Na₂SO₄, filtered and evaporated to dryness to give the title compound, 2.40 kg.

Step C: Preparation of 5-formylbenzofuran

A slurry of powdered magnesium (11.44 g) and iodine (0.12 g) in THF (120 mL) was heated to 50° C. under a N₂ blanket for 0.5 hr. A 30 mL portion of the material prepared above in Example 31, Step B (90 g) in THF (225 mL) was then added at 50° C., without stirring. This mixture was aged for 0.5 hr and the the remaining 195 mL of the THF solution was added over 1.5 hr (with stirring) while maintaining a gentle reflux. When the addition was complete, the mixture was aged at 50° C. for 1 hr and then was cooled to 5° C. before DMF (45 mL) was added dropwise over 30 min while maintaining the reaction temperature between 5°-10° C. The mixture was then aged at 10° C. for 1 hr and then cooled to 5° C. before a mixture of 3N HCl (300 mL) and a 50% sat. solution of brine (225 mL) was added while maintaining the reaction temperature below 15° C. The pH was also monitored and when the pH of the aqueous layer had fallen to 6, EtOAc (200 mL) was added and the remaining 3N HCl/brine mixture was added (final pH approx. 1.2). This mixture was stirred for 1 hr and the aqueous layer was removed and extracted with EtOAc (150 mL). The combined organic layers were washed successively with 2N HCl (100 mL) and brine (3×80 mL), dried over Na₂SO₄, filtered and evaporated to dryness to give 63.6 g of the title compound as an orange oil that was of sufficient purity for use in the next step.

Step D: Preparation of (S)-1-(benzofuran-5-yl)-1-butanol

To a solution of (R,R)-di-(trifluoromethylsulfonyl)-1,2-diaminocyclohexane (1.92 g) in dry toluene (80 mL) at 23° C. under a N₂ blanket was added titanium tetraisopropoxide (15 mL) and the slurry was warmed to 40° C. for 20 min, and then was cooled to 0° C. In a separate vessel di-n-propylzinc (52 mL) was mixed with dry hexane (400 mL) and the resulting homogeneous solution was added to the solution prepared above while maintaining the temperature between −5°-0° C. This mixture, at 0° C., was then added to a solution of the material prepared above in Example 31, Step C (40 g) in toluene (150 mL) over 30 min. The resulting yellow mixture was then stirred at 0° C. for 18 hr and then was cooled to −5° C. and quenched by the addition of 2N HCl (500 mL) over 1.5 hr, while maintaining the reaction temperature between −5°-0° C. The resulting two phase mixture was stirred at 0° C. for 1.2 hr and EtOAc (100 mL) was added. The aqueous layer was removed and extracted with EtOAc (150 mL). The combined organic layers were washed successively with 2N HCl (100 mL) and brine (2×150 mL) and then were dried over Na₂SO₄, filtered and evaporated to dryness to afford 50 g of a yellow oil which solidifed on standing. The optical purity of this material is 95.5% ee.

Step E: Preparation of (R)-1-amino-1-(benzofuran-5-yl)-butane

To a solution of triphenylphosphine (132.3 g) in THF (960 mL) at 0° C. was added ethyl azodicarboxylate (79.2 mL). The resulting solution was stirred at 0° C. until a thick slurry was obtained and then diphenylphosphoryl azide (54.2 mL) was added. To this mixture was added a solution of the material prepared above in Example 31, Step D (47.7 g) in THF (125 mL) over a 1.5 hr time period while maintaining the reaction temperature between −3°−−2° C., and the resulting homogeneous solution was stirred at 0° C. for 0.5 hr. To this mixture was added triphenylphosphine (96.2 g) and the solution was allowed to warm to 23° C. over 1 hr and then was heated at 50° C. for 2.5 hr. 20% Aqueous NaOH (580 mL) was then added to the mixture which was stirred at 50° C. for an additional 1 hr. The two phases mixture was cooled to 23° C. and the lower aqueous layer was separated and extracted with THF (300 mL). The combined organic layers were washed with brine (2×500 mL) and then concentrated in vacuo to give 460 g of an orange oil which was dissolved in t-butylmethyl ether (1 L) and allowed to stand for 18 hr. The solid which formed was filtered off and washed with t-butylmethyl ether (100 mL) and the filtrate was concentrated to dryness to afford 302 g of an orange oil which was purified by silica gel chromatography (1.5 kg column developed successively with hexane:EtOAc (1:1, 8L), EtOAc (4 L) and then EtOAc containing 1% $Et_3N$). Fractions containing the required product (and triphenylphosphine oxide) were pooled and evaporated to dryness. The oily residue so obtained was swished with hexane:EtOAc (5:1, 200 mL) and filtered. The filtrate was concentrated in vacuo to afford 35.3 g of an oil which was dissolved in EtOAc (80 mL) and washed with 2N HCl (2×45 mL). The pooled aqueous layers were cooled to 5° C. and treated with 50% NaOH (20 mL) before being extracted with $Et_2O$ (2×50 mL). The combined organic layers were dried over $Na_2SO_4$, filtered and evaporated to dryness to afford 20.3 g of the title compound as an orange oil with an optical purity of 88% ee.

Step F: Preparation of (R)-5-[(1-isocyanate)butan-1-yl]benzofuran

To a solution of the material prepared above in Example 31, Step E (19.2 g) in toluene (192 mL) was added conc. HCl (12.7 mL) dropwise, while maintaining the reaction temperature between 20°-25° C. The white viscous slurry was stirred for 30 min at 20° C. and then toluene (200 mL) was added and the slurry was heated at reflux with the azeotropic removal of water. The dried slurry was then cooled to 100° C. and a solution of phosgene in toluene (1.93M, 150 mL) was added slowly over 1 hr. Complete solution was obtained after 1 additional hr. This solution was cooled to 10° C. and sat. $NaHCO_3$ (200 mL) was added followed by EtOAc (300 mL). The organic layer was separated and washed successively with sat. $NaHCO_3$ (200 mL) and brine (200 mL) and then dried over $Na_2SO_4$, filtered and evaporated to dryness to give the title compound (21.5 g) as an orange oil suitable for use in the next step.

EXAMPLE 32

(4S)-3,3-Diethyl-1-[[(R)-1-(benzofuran-5-yl)butylamino]carbonyl]-4-[4-(carboxymethyl)phenoxy]azetidin-2-one Method A:

Step A: Preparation of ethyl 4-[(2,2-diethoxy)-ethoxy]-phenylacetate

To a solution of 4-hydroxyphenylacetic acid (50.0 gm, 0.33 mol) in DMSO (300 mL) was added 50% aqueous NaOH (57.0 gm, 0.71 mol) with stirring. After stirring for 10 min at room temperature bromoacetaldehyde diethyl acetal (66.0 gm, 0.33 mol) was added. The solution was heated at 100°-110° C. for 2 hr when an additional 2 gm of 50% NaOH was added. After heating for another hour the reaction mixture was cooled and poured into a mixture of aqueous HCl (30 mL of conc. HCl in 400 mL ice-$H_2O$) and $Et_2O$. The layers were separated and hexane was added to the $Et_2O$ layer. The organic layer was washed successively with $H_2O$ (twice) and saturated NaCl before being dried over $Na_2SO_4$, filtered and evaporated to dryness to give 83.7 gm (0.31 mol) of 4-[(2,2-diethoxy)ethoxy]phenylacetic acid which was suitable for use in the next step.

NMR ($CDCl_3$), δ from TMS: 1.25 (t, 6H, J=7 Hz), 3.56-3.90 (m, 4H), 3.61 (s, 2H), 4.03 (d, 2H, J=7 Hz), 4.86 (t, 1H, J=7 Hz), 6.91 (d, 2H, J=8 Hz), 7.21 (d, 2H, J=8 Hz).

The residue prepared above was dissolved in EtOH (500 mL) containing conc. $H_2SO_4$ (1 mL) and the solution was heated under reflux for 6 hr. The reaction mixture was then cooled, concentrated to 300 mL and this solution was partitioned between $H_2O$ and $Et_2O$. The aqueous layer was extracted with $Et_2O$ and the pooled organic layers were washed successively with $H_2O$, sat. $NaHCO_3$, and sat. NaCl before being dried over $Na_2SO_4$, filtered and evaporated to dryness to give 86.0 gm (0.29 mol), of the title compound.

NMR ($CDCl_3$), δ from TMS: 1.25 (t, 9H, J=7 Hz), 3.55-3.90 (m, 4H), 3.56 (s, 2H), 4.02 (d, 2H, J=7 Hz), 4.16 (q, 2H, J=7 Hz), 4.86 (t, 1H, J=7 Hz), 6.89 (d, 2H, J=8 Hz), 7.20 (d, 2H, J=8 Hz).

Step B: Preparation of ethyl benzofuran-5-ylacetate

In a 1 L 3-necked flask equipped with a mechanical stirrer and a condenser was added polyphosphoric acid (80 gm) and benzene (450 mL). This mixture was heated to reflux for 15 min and then ethyl 4-[(2,2-diethoxy)ethoxy]phenylacetate (86 gm, 0.29 mol) in benzene (50 mL) was added and the reflux was continued for 40 min. The reaction mixture was cooled and the mobile phase was decanted off. This benzene solution was washed successively with $H_2O$, sat. $NaHCO_3$, and sat. NaCl before being dried over $Na_2SO_4$, filtered and evaporated to dryness. This residue was dissolved in 10-15% EtOAc in hexane and passed through a short silica gel column (5 cm×10 cm dia.) in the same solvent. The eluent was evaporated to dryness to give a yellow liquid which was further purified by preparative LC using 10% EtOAc in hexane as eluent to give 17.4 gm of ethyl benzofuran-5-ylacetate.

NMR ($CDCl_3$), δ from TMS: 1.26 (t, 3H, J=7 Hz), 3.70 (s, 2H), 4.19 (q, 2H, J=7 Hz), 6.75 (m, 1H), 7.2-7.7 (m, 4H).

Step C: Preparation of (R,S)-α-Allylbenzofuran-5-ylacetic acid

Ethyl benzofuran-5-ylacetate (17.42 gm, 0.085 mol) was dissolved in dry THF (120 mL) and the solution was cooled under a nitrogen blanket in a dry ice bath. After 10 min, a solution of 1M lithium bis(trimethylsilyl)amide in THF (90 mL) was added via an addition funnel over a 15 min time period. After stirring for 15 min, allyl bromide (7.9 mL, 11.04 gm, 0.091 mol) was added and the stirred solution was allowed to rise to room temperature over 1 hr. The solution was poured into ice-$H_2O$ containing 20 mL of 1.2N HCl and extracted with $Et_2O$. The organic layer was washed successively with 1.2N HCl and sat. NaCl before being dried over $Na_2SO_4$, filtered and evaporated to dryness to give 21.6 gm of crude ethyl (R,S)-α-allylbenzofuran-5-ylacetate.

The ethyl (R,S)-α-allylbenzofuran-5-ylacetate obtained above was dissolved in EtOH (200 mL) and treated with $H_2O$ (30 mL) and 5N NaOH (30 mL). This solution was heated at 60° C. for 1.5 hr, stirred overnight at room temperature and then heated at 60° C. for an additional 1 hr before being worked up. The reaction mixture was cooled and poured into ice-$H_2O$ (400 mL) containing conc. HCl (14 mL) and $Et_2O$. The layers were separated and the aqueous layer was further extracted with $Et_2O$. The pooled $Et_2O$ layers were washed successively with H₂O and sat. NaCl, dried over Na₂SO₄, filtered and evaporated to dryness to give 16.88 gm of (R,S)-α-allylbenzofuran-5-ylacetic acid which solidified on standing.

NMR (CDCl₃), δ from TMS: 2.58 (m, 1H), 2.84 (m, 1H), 3.72 (m, 1H), 5.00–5.20 (m, 2H), 5.64–5.84 (m, 1H), 6.74 (m, 1H), 7.20–7.70 (m, 4H).

Step D: Preparation of (R)-α-allylbenzofuran-5-ylacetic acid, (R)-(+)-α-methylbenzylamine salt To a solution of the racemate prepared above in Example 32, Method A, Step C (39.43 gm, 0.18 mol) in iPrOH (285 mL) was added (R)-α-methylbenzylamine (14.4 gm, 0.12 mol). A solid formed immediately and the mixture was allowed to stand at room temperature for 1 hr. The solid was filtered off, washed with cold iPrOH and dried. This solid ($\alpha_D = -4.55$) was recrystallized from iPrOH (750 mL) to give 26.9 gm of material with $\alpha_D = -14.1$. An additional recrystallization from iPrOH (800 mL) gave 20.3 gm (0.06 mol) of product with $\alpha_D = -22.61$ which was suitable for use in the next step.

Note that the mother liquors from these crystallizations can be racemized (via conversion to the free acid and esterification, followed by successive treatments with lithium bis(trimethylsilyl)amide, acetic acid and then de-esterification with NaOH in MeOH) and then resolution of this material can be realized as described above. In this fashion the bulk of the racemate can be converted into the required enantiomer.

Step E: Preparation of (R)-α-allylbenzofuran-5-ylmethyl isocyanate

The material prepared above in Example 32, Method A, Step D (20.3 gm, 0.06 mol) was added to 2N HCl (35 mL) in a mixture of ice-H₂O (150 mL) and Et₂O (150 mL). This mixture was stirred for a few minutes until the solid dissolved and the layers were then separated and the aqueous layer was extracted with Et₂O. The Et₂O layer was washed with sat. NaCl, dried over Na₂SO₄, filtered and evaporated to dryness. The residue so obtained was dissolved in CH₂Cl₂ (200 mL) and 25 drops of DMF were added. This solution was cooled in an ice bath and a solution of oxalyl chloride (5.5 mL, 0.063 mol) in CH₂Cl₂ (20 mL) was added over a 10 min period. The reaction mixture was stirred for 1 hr (gas evolution stopped after approximately 45 min) and then was evaporated to dryness. The residue so obtained was dissolved in acetone (120 mL) and the solution was added to a cooled (ice bath) solution of NaN₃ (4.11 gm, 0.063 mol) in H₂O (80 mL) while maintaining the temperature between 2°–5° C. After the addition was completed, the reaction was stirred for 30 min and then poured into a mixture of ice-H₂O/CHCl₃. The layers were separated and the aqueous layer was extracted with CHCl₃. The pooled organic layers were washed with cold H₂O and sat. NaCl before being dried over Na₂SO₄, filtered and concentrated to 250 mL. This solution was heated in an oil bath at 60° C. for 30 min (gas evolution ceased) and then was evaporated to dryness. The residue so obtained was dried by azeotropic concentration from a benzene solution (150 mL) and then was stored in the freezer overnight as a benzene solution before being used in the next step. Upon evaporation to dryness, this solution contained 12.8 gm (0.06 mol) of product.

Step F: Preparation of (4S)-3,3-diethyl-1-[{(R)-1-(benzofuran-5-yl)-but-3-enylaminocarbonyl]-4-[4-(allyloxycarbonylmethyl)phenoxy]azetidin-2-one (R)-α-Allylbenzofuran-5-ylmethyl isocyanate (8.52 gm, 0.04 mol), prepared as described above in Step E, was added to a solution of (S)-3,3-diethyl-4-[(4-allyloxycarbonylmethyl)phenoxy]azetidin-2-one (11.33 gm, 0.035 mol, prepared as described in Example 30) in DMF (70 mL) and powdered K₂CO₃ (0.97 gm) was added. This mixture was stirred vigorously for 1.5 hr and was then poured into H₂O/Et₂O. The layers were separated and the Et₂O layer was washed with H₂O (twice) and sat. NaCl before being dried over Na₂SO₄, filtered and evaporated to dryness. The residue so obtained was purified by preparative LC using hexane /EtOAc/CH₂Cl₂ (82:15:3) as the eluent, to give 13.9 gm (0.026 mol) of the required product.

NMR (CDCl₃), δ from TMS: 0.95 (t, 3H, J=7 Hz), 1.07 (t, 3H, J=7 Hz), 1.7–2.1 (m, 4H), 2.63 (t, 3H, J=7 Hz), 3.59 (s, 2H), 4.58 (d of t, 2H, J=6 Hz, J=1 Hz), 5.04–5.32 (m, 5H), 5.57 (s, 2H), 5.57–6.06 (m, 2H), 6.74 (d of d, 1H, J=2 Hz, J=1 Hz), 7.1–7.56 (m, 8H), 7.61 (d, 1H, J=2 Hz)

Step G: Preparation of (4S)-3,3-diethyl-1-[{(R)-1-(benzofuran-5-yl)-but-3-enylaminocarbonyl]-4-[4-(carboxymethyl)phenoxy]azetidin-2-one To a solution of (4S)-3,3-diethyl-1-[{(R)-1-(benzofuran-5-yl)-but-3-enylaminocarbonyl]-4-[4-(allyloxycarbonylmethyl)phenoxy]azetidin-2-one (15.04 gm, 0.028 mol) in EtOAc (250 mL) was added triphenylphosphine (0.5 gm, 0.002 mol) and acetic acid (10 mL). The solution was degassed and maintained under an atmosphere of nitrogen. Tetrakis(triphenylphosphine)palladium(0) (0.5 gm, 0.00043 mol) was then added and the reaction mixture was stirred for 3 hr and then an additional 10 mL of acetic acid was added. After stirring for a total of 6.5 hr, the reaction was diluted with Et₂O and the mixture was extracted with H₂O (twice) and sat. NaCl. The organic phase was dried over Na₂SO₄, filtered and evaporated to dryness to give 17.9 gm of crude product as an oil which was suitable for use in the next step.

NMR (CDCl₃), δ from TMS: 0.95 (t, 3H, J=7 Hz), 1.07 (t, 3H, J=7 Hz), 1.7–2.1 (m, 4H), 2.63 (t, 2H, J=7 Hz), 3.59 (s, 2H), 5.04–5.30 (m, 3H), 5.58 (s, 1H), 5.58–5.90 (m, 1H), 6.74 (d of d, 1H, J=2 Hz J=1 Hz), 7.10–7.56 (m, 8H), 7.60 (d, 1H, J=2 Hz).

Step H: Preparation of (4S)-3,3-diethyl-1-[[(R)-1-(benzofuran-5-yl)butylamino]carbonyl]-4-[4-(carboxymethyl)phenoxy]azetidin-2-one The crude (4S)-3,3-diethyl-1-[{(R)-1-(benzofuran-5-yl)-but-3-enylaminocarbonyl]-4-[4-(carboxmethyl)-phenoxy]azetidin-2-one prepared as described above in Example 32, Method A, Step G (17.9 gm) was dissolved in EtOAc (60 mL) and diluted with abs. EtOH (110 mL). This solution was hydrogenated for 30 min on a Parr shaker in three portions using 5% Pd on C as catalyst (0.5 g in each portion). Hydrogen uptake was slow, and after 5 min, 0.15 gm of 10% Pd on C was added to each portion. After an additional 25 min, the reactions were pooled, filtered, and the filtrate was evaporated to dryness. The residue was dissolved in EtOAc (20 mL)-EtOH (80 mL), divided into two equal portions, 10% Pd on C (0.15 gm) was added to each, and the hydrogenation was continued for 15 min. The reaction mixture was then filtered, washed with EtOAc and evaporated to dryness. This residue was then purified by preparative LC to give 11.03 gm (0.022 mol) of the required product as a stiff clear foam.

NMR (CDCl₃), δ from TMS: 0.92 (t, 3H, J=7 Hz), 0.93 (t, 3H, J=7 Hz), 1.07 (t, 3H, J=7 Hz), 1.33 (m, 2H), 1.7–2.1 (m, 6H), 3.59 (s, 2H), 4.95 (q, 1H, J=8 Hz), 5.58

(s, 1H), 6.74 (d of d, 1H, J=1 Hz, J=2 Hz), 7.0–7.54 (m, 8H), 7.61 (d, 1H, J=2 Hz).

Step I: Preparation of (4S)-3,3-diethyl-1-[[(R)-1-(benzofuran-5-yl)butylamino]carbonyl]-4-[4-(carboxymethyl)phenoxy]azetidin-2-one, potassium salt A solution of the free acid (7.01 gm 0.014 mol), prepared as described above in Example 32, Method A, Step H in H$_2$O (100 mL) was treated with a solution of KHCO$_3$ (1.424 gm, 0.014 mol) in H$_2$O (100 mL). Warming of the mixture and the addition of MeOH (20 mL) was required to obtain a homogeneous milky solution. This was filtered and the filtrate was concentrated to 150 mL, diluted with H$_2$O (100 mL) and then lyophilized to give the required product as a hygrocopic white solid which analysed as a hydrate. Optical rotation $a_D$ (c=0.49, MeOH)= +55.31;

Anal. Calc. for C$_{28}$H$_{31}$N$_2$O$_6$K$_2$.75H$_2$O (580.21); C, 57.96, H, 6.34, N, 4.83, Found; C, 57.94, H, 6.10, N, 4.68

Method B:

Step A: Preparation of p-methoxybenzyl bromide p-Methoxybenzyl alcohol (13.8 g, 0.1 mol) was added dropwise to a solution of 48% HBr (50 gm, 0.3 mol of HBr) over a period of 15 min and the solution was then stirred for an additional 15 min before being poured into a mixture of ice-H$_2$O and Et$_2$O. The layers were separated and the aqueous layer was extracted with Et$_2$O. The combined Et$_2$O extracts were washed with sat. NaCl, dried over Na$_2$SO$_4$ and evaporated to dryness to give 23.4 gm of p-methoxybenzyl bromide suitable for use in the next step.

NMR (CDCl$_3$), δ from TMS: 3.80 (s, 3H), 4.49 (s, 2H), 6.86 (d, 2H, J=8 Hz), 7.32 (d, 2H, J=8 Hz).

Step B: Preparation of (S)-3,3-diethyl-4-[4-({p-methoxybenzyloxycarbonylmethyl)phenoxy]azetidin-2-one (S)-3,3-Diethyl-4-[4-(carboxymethyl)phenoxy]azetidin-2-one, (S)-(−)-α-methylbenzylamine salt (31.8 gm, 0.08 mol) was added to a mixture of H$_2$O, 2N HCl, and Et$_2$O and was mixed thoroughly until dissolution occured. The layers were separated and the organic layer was washed successively with H$_2$O and sat. NaCl, before being dried over Na$_2$SO$_4$, filtered and evaporated to dryness. This residue was dissolved in DMF (100 mL) and powdered K$_2$CO$_3$ (11.81 gm, 0.085 mol) was added. After 5 min, p-methoxybenzyl bromide (23.4 gm, 0.08 mol) in DMF (20 mL) was added and the solution was stirred at room temperature overnight and then poured into a mixture of H$_2$O and Et$_2$O. The layers were separated and the organic layer was washed successively with H$_2$O (twice), and sat. NaCl before being dried over Na$_2$SO$_4$, filtered and evaporated to dryness to give 32.82 gm of (S)-3,3-diethyl-4-[4-({p-methoxybenzyloxycarbonylmethyl)phenoxy]azetidin-2-one as a yellow oil suitable for use without further purification.

NMR (CDCl$_3$), δ from TMS: 1.03 (t, 3H, J=7 Hz), 1.06 (t, 3H, J=7 Hz), 1.65–2.05 (m, 4H), 3.59 (s, 2H), 3.80 (s, 3H), 5.05 (s, 2H), 5.53 (s, 1H), 6.65 (br s, 1H), 6.80–7.40 (m, 8H).

Step C: Preparation of (4S)-3,3-diethyl-1[{(R)-1-(benzofuran-5-yl)-but-3-enylaminocarbonyl]-4-[4-({p-methoxybenzyloxycarbonylmethyl)phenoxy]azetidin-2-one (R)-α-Allylbenzofuran-5-ylmethyl isocyanate (12.8 gm, 0.06 mol), prepared as described in Example 32, Method A, Step E was dissolved in DMF (50 mL) and a solution of (4S)-3,3-diethyl-4-[4-({p-methoxybenzyloxycarbonylmethyl)phenoxy]azetidin-2-one, prepared as described above in Example 32, Method B, Step B (19.85 gm, 0.05 mol) in DMF (50 mL) was added. Powdered K$_2$CO$_3$ (1.39 gm) was added and the mixture was vigorously stirred for 2 hr at room temperature. The reaction mixture was then partitioned between Et$_2$O and H$_2$O and the aqueous layer was further extracted with Et$_2$O. The pooled organic layers were washed successively with H$_2$O (twice) and sat. NaCl before being dried over Na$_2$SO$_4$, filtered and evaporated to dryness. This residue so obtained was purified in two batches on preparative LC, using 25–50% EtOAc in hexane as eluent, to give 20.3 gm (0.033 mol) of the desired product.

NMR (CDCl$_3$), δ from TMS: 0.95 (t, 3H, J=7 Hz), 1.08 (t, 3H, J=7 Hz), 1.65–2.05 (m, 4H), 2.63 (t, 2H, J=7 Hz), 3.58 (s, 2H), 3.81 (s, 3H), 5.00–5.22 (m, 3H), 5.05 (s, 2H), 5.58 (s, 1H), 5.60–5.80 (m, 1H), 6.70–7.70 (m, 14H).

Step D: Preparation of (4S)-3,3-diethyl-1-[{(R)-1-(benzofuran-5-yl)butylaminocarbonyl]-4-[4-({p-methoxybenzyloxycarbonylmethyl)phenoxy]-azetidin-2-one The (4S)-3,3-diethyl-1-[{(R)-1-(benzofuran-5-yl)-but-3-enylaminocarbonyl]-4-[4-({p-methoxybenzyloxycarbonylmethyl)phenoxy]azetidin-2-one prepared as described above in Example 32, Method B, Step C (20.3 gm, 0.033 mol) was dissolved in EtOAc (50 mL) and EtOH (150 mL). This solution was divided into four equal portions and each was hydrogenated at <35 psi using 5% Pd/C (0.5 gm) in a Parr apparatus. The hydrogenation was stopped after initial hydrogen absorption had stopped (3.5–4 min) and the catalyst was removed by filtration and washed with EtOAc. The filtrates from the four runs were pooled and evaporated to dryness to give 19.0 gm (0.031 mol) of the required product which was suitable for use in the next step without further purification.

NMR (CDCl$_3$), δ from TMS: 0.92 (t, 3H, J=7 Hz), 0.94 (t, 3H, J=7 Hz), 1.08 (t, 3H, J=7 Hz), 1.30 (m, 2H), 1.65–2.10 (m, 6H), 3.59 (s, 2H), 3.81 (s, 3H), 4.97 (q, 1H, J=7 Hz), 5.06 (s, 2H), 5.58 (s, 1H), 6.70–7.70 (m, 14H).

Step E: Preparation of (4S)-3,3-Diethyl-1-[[(R)-1-(benzofuran-5-yl)butylamino]carbonyl]-4-[4-(carboxymethyl)phenoxy]azetidin-2-one The (4S)-3,3-diethyl-1-[{(R)-1-(benzofuran-5-yl)butylaminocarbonyl]-4-[4-({p-methoxybenzyloxycarbonylmethyl)phenoxy]azetidin-2-one prepared as described above in Example 32, Method B, Step D (13.53 gm, 0.022 mol) was dissolved in anisole (15 mL) and the solution was cooled in an ice bath for 15 min. This chilled solution was then divided into three portions and to each was added ice cold CF$_3$CO$_2$H (20 mL). After 10 min at ice bath temperature, dichloroethane (50 mL) was added to each portion and the solutions were rapidly evaporated to dryness (bath temperature <30° C.) and the residues were diluted with Et$_2$O and poured into ice-H$_2$O. The layers were separated and the aqueous layer was extracted with Et$_2$O. The Et$_2$O layers from the three reactions were pooled and washed successively with cold H$_2$O and sat. NaCl before being dried over Na$_2$SO$_4$, filtered and evaporated to dryness. This residue was purified by preparative LC to give 6.68 gm (0.014 mol) of the required product as a thick oil. This material was identical in all respects to that prepared via Method A.

Method C:

Step A: Preparation of methyl benzofuran-5-ylacetate

4-Hydroxyphenylacetic acid (20 gm, 0.13 mol) was dissolved in DMF (50 ml) and then slowly added to washed NaH (0.26 mol) in DMF (100 ml). Bromoacetaldehyde diethyl acetal (29 ml, 0.195 mol) was then added and the mixture was heated at 160° C. (oil bath) for 3 hr. The mixture was cooled, water was added and the mixture was rendered basic by the addition of 2N NaOH. The solution was heated to 80° C. for 1 hr and then was cooled and extracted twice with Et$_2$O, acidified to pH 3 and then extracted twice more with Et$_2$O. The second Et$_2$O extracts were pooled, dried and evaporated to dryness. This residue was purified by preparative LC to give 8 gm of a pure oil which was dissolved in Et$_2$O and 120 ml of a CH$_2$N$_2$ solution was added (slight molor excess). Upon completion of the esterification, the excess CH$_2$N$_2$ was destroyed by the addition of acetic acid and the mixture was evaporated to an oil. This was dissolved in benzene (100 ml) and polyphosphoric acid (5 gm) was added and the mixture was heated at 90°–100° C. with good mechanical stirring for 3 hr. The mixture was decanted and evaporated to dryness and the residue was purified by flash chromatography to give 1.3 gm of the title compound as an oil.

NMR (CDCl$_3$): δ 3.58–3.83 (m, 5H), 6.74 (d of d, 1H), 7.18–7.54 (m's, 5H), 7.62 (d, 1H)

Step B: Preparation of benzofuran-5-ylacetic acid 1.20 gm (6.3 mmol) of material prepared as described in Step A above was treated with 2N NaOH (6.5 ml) and MeOH (10 ml) at room temperature for 3 hr. The reaction mixture was then diluted with H$_2$O and the resultant solution was washed with Et$_2$O. The aqueous layer was acidified and extracted twice with EtOAc. The combined EtOAc layers were dried over Na$_2$SO$_4$, filtered and evaporated to dryness to give 1.1 gm (6.25 mmol) of the title compound suitable for direct use in the next step.

Step C: Preparation of (R)-α-allyl-benzofuran-5-ylacetic acid, (R)-(+)-α-methylbenzylamine salt (alternate route to that described in Example 32 Method A, Step D 10.0 gm (56.76 mmol) of material prepared as described in Step B above was dissolved in THF (300 ml) and added dropwise over 15 min to a cold (−5° to −10° C.) solution of lithium diisopropylamine [prepared from diisopropylamine (20.45 ml, 141.88 mmol) and 2.5M n-BuLi (48 ml, 120 mmol)] in THF. The reaction mixture was stirred at −10° C. for 30 min and then a solution of allyl bromide (10.81 ml, 113.52 mmol) in THF (20 ml) was added quickly. This mixture was stirred at −10° C. for 30 min and then cooled and added to a mixture of ice-H$_2$O (900 ml), 2N HCl (300 ml) and Et$_2$O (500 ml). After stirring for 5 min the layers were separated and the aqueous layer was washed with Et$_2$O (100 ml) and the pooled organic layers were washed successively with aqueous NaHSO$_3$ and brine and then dried over Na$_2$SO$_4$, filtered and evaporated to dryness. The orange-yellow oil so obtained was dissolved in isopropanol (255 ml) and (R)-(+)-α-methylbenzylamine (5.43 ml, 42.57 mmol) was added, with stirring. Any solids which formed were redissolved by heating and the solution was allowed to cool in the freezer overnight. Several recrystallizations from isopropanol gave the title compound (7.19 gm) as a white solid which was identical to material prepared in Example 32, Method A, Step D.

Step D: Preparation of (R)-α-allyl-benzofuran-5-ylmethyl isocyanate

This was prepared as described in Example 32, Method A, Step E.

Step E: Preparation of (4S)-3,3-diethyl-1-[[(R)-1-(5-benzofuran-5-yl)-but-3-enylamino]carbonyl]-4-[(4-t-butoxycarbonylmethyl) phenoxy]azetidin-2-one A solution of the material prepared in Step D above (470 mg, 2.2 mmol) and the material prepared in Example 22 (600 mg, 1.8 mmol) in Et$_3$N (0.38 ml, 2.7 mmol), DMAP (5 mg) and CH$_2$Cl$_2$ (5 ml) was stirred overnight at room temperature and then was heated at 40°–50° C. The reaction mixture was evaporated to dryness and the residue was purified by repeated chromatography to give 350 mg of the title compound (higher Rf isomer).

NMR (CDCl$_3$): δ 0.92 (2t's, 6H), 1.08 (t, 3H), 1.34 (m, 2H), 1.43 (s, 9H), 1.68–2.1 (m, 6H), 3.46 (s, 2H), 4.95 (q, 1H), 5.55 (s, 1H), 6.74 (m, 1H), 6.96–7.56 (m's, 8H), 7.61 (d, 1H)

The lower R$_f$ isomer, (4R)-3,3-diethyl-1-[(R)-α-allyl-(5-benzofuranyl)methylaminocarbonyl]-4-[(4-t-butoxycarbonylmethyl)phenoxy]azetidin-2-one, was also obtained, 400 mg.

Step F: Preparation of (4S)-3,3-diethyl-1-[(R)-1-(benzofuran-5-yl)butylamino]carbonyl]-4-[(4-carboxymethyl)phenoxy]azetidin-2-one The higher Rf isomer (350 mg) prepared as described above in Step D was dissolved in EtOAc (10 ml) and 5% Pd/C (50 mg) was added. This mixture was hydrogenated at 20 p.s.i. for 8 min, when tlc and NMR indicated complete reduction of the allyl group. The reaction was filtered and the filtrate was evaporated to dryness. The residue so obtained was dissolved in a mixture of cold CF$_3$CO$_2$H (5 ml) and anisole (1 ml) and the reaction was stored at 0° C. for 20 min before being evaporated to dryness. This crude product was purified by chromatography on thick layer silica gel plates developed with EtOAc/hexane/HOAc (35:64:1) to give 200 mg of the title compound.

NMR (CDCl$_3$): δ 0.92 (t, 3H), 0.94 (t, 3H), 1.04 (t, 3H), 1.34 (m, 2H), 1.68–2.10 (m, 6H), 3.58 (s, 2H), 4.95 (q, 1H), 5.57 (s, 1H), 6.74 (d of d, 1H), 6.98–7.54 (m, 8H), 7.61 (d, 1H)

Method D:

Step A Preparation of (4S)-3,3-diethyl-1-[[(R)-1-(5-benzofuran-5-yl)-butyl-1-amino]carbonyl]-4-[(4-allyloxycarbonylmethyl)phenoxy]-azetidin-2-one To a solution of the material prepared above in Example 31, Step F (19.0 g) in DMF (50 mL) at room temperature was added a solution of the material prepared in Example 30, Method B (26.5 g), also in DMF (100 mL). K$_2$CO$_3$ (1.22 g) was added and the slurry so obtained was stirred for 1 hr. The reaction mixture was then partitioned between EtOAc (250 mL) and 2N HCl (100 mL) and the the organic layer was washed successively with 2N HCl (100 mL), 0.1N HCl (2×100 mL) and brine (2×100 mL) before being evaporated to dryness to give 52.8 g of the title product (de=85%).

Step B: Preparation of (4S)-3,3-diethyl-1-[[(R)-1-(5-benzofuran-5-yl)-butyl-1-amino]carbonyl]-4-[(4-carboxymethyl)phenoxy]-azetidin-2-one, tris (hydroxymethyl)aminomethane salt To a solution of the material prepared above in Example 32, Method D, Step A (10.0 g) in DMF (150 mL) at 20° C. under a N$_2$ blanket was added 10% Pd on carbon (2.0 g), followed by a 55% solution of ammonium formate in H$_2$O (15.0 mL). This mixture was heated at 45° C. for 30 min and then was cooled to 20° C. and filtered (washing the pad with 30 mL of DMF). The filtrate was partitioned between 1N HCl (100 mL) and EtOAc (200 mL) and the organic layer was washed successively with 0.1N HCl (2×100 mL) and brine (2×100 mL) before being evaporated to dryness to give the title compound (free acid) as a pale yellow viscous gum (9.25 g).

A slurry of the free acid prepared as described above (39.0 g) and tris-(hydroxymethyl)aminomethane (9.6 g) in isopropanol (500 mL) was warmed to 60° C. to ensure dissolution. Hexanes (1.3 L) was then added dropwise until a slightly cloudy mixture was obtained. This mixture was seeded (200 mg) and allowed to cool to 20° C. overnight. Hexanes (700 mL) were then added and the slurry was aged at 5° C. for 2 hr and the solid so formed was filtered, washed with isopropanol/hexanes (1:4; 80 mL) and then dried in vacuo at 20° C. to give the title compound (29.9 g).

EXAMPLE 33

(4S)-3,3-Diethyl-1-[(R-α-n-propyl-(4-methyl)-benzylaminocarbonyl-4-[(4-carboxy-3-methyl)-phenoxy]azetidin-2-one Step A: Preparation of 4-hydroxy-2-methylbenzoic acid 4'-Hydroxy-2'-methylacetophenone (15 gm, 0.1 mol) was dissolved in pyridine and iodine (25.4 gm) was added. This mixture was heated to 100° C. for 1 hr and then allowed to stand at room temperature overnight. A thick precipitate was obtained and the mixture was diluted with Et₂O before filtering. The solid so obtained was added to 5N NaOH (200 ml) and heated on the steam bath for 1 hr before being cooled and acidified with HCl. This mixture was extracted twice with Et₂O and the pooled organic layers were washed with brine, dried over Na₂SO₄, filtered and evaporated to dryness. The residue was crystallized from Et₂O-hexane to give 9.8 gm of the title compound as a solid.

Step B: Preparation of benzyl 4-hydroxy-2-methylbenzoate 9.5 gm (63 mmol) of material prepared as described in Step A above was dissolved in DMF (100 ml) and benzyl bromide (8.4 ml, 69.3 mmol) was added followed by powdered K₂CO₃ (13 gm, 94 mmol). This mixture was stirred at 60° C. for 2 hr and then was cooled, diluted with Et₂O and poured onto ice chilled aq. HCl. The layers were separated and the aqueous layer was extracted twice more with Et₂O. The pooled organic layers were washed with brine, dried over Na₂SO₄, filtered and evaporated to dryness. This crude product was purified by flash chromatography (silica gel, using 10%-30% EtOAc in hexane as eluant) to give the title compound as an oil which upon trituration with hexane and cooling gave 8.5 gm of a white solid.

Step C: Preparation of (R,S)-3,3-diethyl-4-[(3-methyl-4-benzyloxycarbonyl)-phenoxy]azetidin-2-one 4-Propionyloxy-3,3-diethylazetidin-2-one (6.2 gm, 31 mmol, prepared in an analogous fashion as described in Example 22, Step B) was dissolved in toluene (100 ml) and material prepared as described in Step B above (5.0 gm, 21 mmol) was added followed by powdered Ba(OH)₂·8H₂O (6.7 gm, 31 mmol). This mixture was heated at 50°-60° C. for 3 hr and then poured into ice-chilled 2N HCl. The mixture was extracted twice with Et₂O and the pooled organic layers were washed with brine, dried over Na₂SO₄, filtered and evaporated to dryness. This residue was purified by flash chromatography (silica gel, using 20%-40% EtOAc in hexane as eluant) to give 5.3 gm of the title compound as a a white solid.

Step D: Preparation of (4S)-3,3-diethyl-1-[(R)-α-n-propyl-(4-methyl)benzylaminocarbonyl]-4-[(4-carboxy-3-methyl)phenoxy]azetidin-2-one A solution of the material prepared in Step C above (2.5 gm, 6.8 mmol) and the material prepared as in Example 28, Method B, Step B (2.0 gm, 10.2 mmol) in Et₃N (1.5 ml, 10.2 mmol) and CH₂Cl₂ (5 ml) was stirred at 50°-60° C. for 20 hr and then overnight at room temperature. The reaction mixture was then cooled and added to dilute HCL. The mix was extracted twice with Et₂O and the pooled organic layers were washed with brine, dried over Na₂SO₄, filtered and evaporated to dryness. The residue was purified by flash chromatography (silica gel, using 10%-20% EtOAc in hexanes as eluant) to give 150 mg of pure (4S)-3,3-diethyl-1-[(R)-α-allyl-(4-methyl)-benzyl-aminocarbonyl-4-[(4-benzyloxycarbonyl-3-methyl)phenoxy]azetidin-2-one. Additional pure material was obtained by repeated chromatography of overlapping fractions. 650 mg of this pure material was dissolved in EtOH (10 ml) and hydrogenated for 2 hr at 40 p.s.i. using 100 mg of 10% Pd/C as catalyst. The reaction was filtered and evaporated to dryness to give 500 mg of the title compound as a pure foam.

NMR (CDCl₃): δ 0.91 (t, 3H), 0.96 (t, 3H), 1.06 (t, 3H), 1.30 (m, 2H), 1.6-2.1 (m, 6H), 2.31 (s, 3H), 2.60 (s, 3H), 4.83 (q, 2H), 5.70 (s, 1H), 6.92 (d, 1H), 6.98-7.22 (m, 6H), 7.99 (d, 1H)

EXAMPLE 34

(4S)-3,3-Diethyl-1-[(R)-α-n-propyl-(4-methyl)benzylaminocarbonyl]-4-[(4-carboxy-3-chloro)phenoxy]-azetidin-2-one Starting with 4-propionyloxy-3,3-diethylazetidin-2-one (prepared in an analogous fashion as described in Example 22, Step B and as shown in Scheme (d)), followed by displacement with benzyl 2-chloro-4-hydroxybenzoate (prepared from 2-chloro-4-hydroxybenzoic acid in a fashion analogous to that described in Example 23, for benzyl 4-hydroxy-phenyl acetate) as described in Example 24, Method A, Step C and acylation of the nitrogen with the isocyanate prepared as described in Example 28, followed by catalytic reduction and deblocking gave the title compound.

NMR (CDCl₃): δ 0.9 (t, 3H), 0.97 (t, 3H), 1.05 (t, 3H), 1.31 (m, 2H), 1.7-2.1 (m, 6H), 2.33 (3, 3H), 4.82 (q, 1H), 5.68 (s, 1H), 6.90 (d, 1H), 7.1-7.4 (m, 6H), 7.98 (d, 1H)

EXAMPLE 35

(4S)-3,3-Diethyl-1-[(R)-α-n-propyl-(4-methyl)benzylaminocarbonyl]-4-[(4-carboxy-3-fluoro)phenoxy]-azetidin-2-one This was prepared as described above in Example 33 except that benzyl 2-fluoro-4-hydroxybenzoate (prepared from 2-fluoro-4-nitrotoluene by oxidation with KMnO₄ to give 2-fluoro-4-nitrobenzoic acid, followed by catalytic reduction to give 4-amino-2-fluorobenzoic acid, followed by diazotization/hydrolysis to give 4-hydroxy-2-fluorobenzoic acid which was converted to benzyl 2-fluoro-4-hydroxybenzoate in a fashion analogous to that described in Example 23) was used as starting material in place of benzyl 2-chloro-4-hydroxybenzoate.

NMR (CDCl₃): δ 0.91 (t, 3H), 0.97 (t, 3H), 1.02 (t, 3H), 1.30 (m, 2H), 1.7-2.1 (m, 6H), 2.32 (s, 3H), 4.83 (q, 1H), 5.70 (s, 1H), 6.9-7.3 (m, 6H), 7.94 (t, 1H)

EXAMPLE 36

(4S)-3,3-Diethyl-1-[(R)-α-n-propyl-(4-ethoxy)benzylaminocarbonyl]-4-[(4-carboxymethyl)phenoxy]azetidin-2-one Step A: Preparation of (R)-α-allyl-(4-ethoxyphenyl)-methyl acetic acid, (R)-(+)-α-methylbenzylamine salt A solution of 4-ethoxyphenylacetic acid (9.4 gm) in THF (50 ml) was cooled in a dry-ice bath under a nitrogen atmosphere and 110 ml of a 1M solution of lithium bis(trimethylsilyl)amide in THF was added dropwise. After 10 min the cooling bath was removed and and the solution was allowed to warm up. After an additional 30 min the flask was chilled in an ice-bath and allyl bromide (5.1 ml) was added. The reaction mixture was allowed to rise to room temperature over 1 hr and then was poured into aq. HCl/ice. This was extracted with $Et_2O$ and the organic layer was washed with brine, dried over $Na_2SO_4$, filtered and evaporated to dryness. The residue so obtained was diluted with isopropanol (40 ml) and (R)-(+)-α-methylbenzylamine (3.5 gm) was added. A solid formed which was filtered off, and washed with cold isopropanol to give 4.08 gm of crude product. This solid was recrystallized twice from isopropanol to give 2.23 gm of the title compound as a white solid. $[\alpha]_D -20.42$.

Step B: Preparation of (R)-α-allyl-(4-ethoxy)benzylisocyanate 2.2 gm of the material prepared in Step A above was acidified with 1.2N HCl in the presence EtOAc. The organic layer was separated, washed with brine, dried over $Na_2SO_4$, filtered and evaporated to dryness. The residue so obtained was dissolved in acetone (12 ml) and added to a solution of $NaN_3$ (0.5 gm) in $H_2O$ (9 ml), while maintaining the temperature below 5° C. After stirring for 0.5 hr, the solution was partitioned between $H_2O$ and $CHCl_3$ and the organic layer was washed successively with $H_2O$ and brine, and then dried over $Na_2SO_4$, filtered and concentrated to approximately 20 ml. This solution was heated on an oil bath at 60° C. for 1 hr and then evaporated to dryness to give 1.4 gm of the title compound which was sufficiently pure for the next step.

Step C: Preparation of (4S)-3,3-diethyl-1-[(R)-α-allyl-(4-ethoxy)benzylaminocarbonyl]-4-[(4-benzyloxycarbonylmethyl)phenoxy]-azetidin-2-one To a solution of the material prepared in Example 27 (0.5 gm) in $CH_2Cl_2$ (1 ml), 0.25 ml of $Et_3N$ was added followed by 0.35 gm of the material prepared in Step B above and a trace of 4-dimethylaminopyridine. This solution was heated at 40° C. for 3 days and the mixture was then diluted with $CH_2Cl_2$, washed successively with 1.2N HCl and brine, and then dried over $Na_2SO_4$, filtered and evaporated to dryness. The residue so obtained was purified by flash chromatography (silica gel, 10% to 30% EtOAc in hexane) to give 0.395 gm of the title compound.

Step D: Preparation of (4S)-3,3-diethyl-1-[(R)-α-n-propyl-(4-ethoxy)benzylaminocarbonyl]-4-[(4-carboxymethyl)-phenoxy]azetidin-2-one To a solution of 0.395 gm of the the material prepared in Step C above in EtOH (4 ml) was added 5% Pd/C (50 mg) and the mixture was hydrogenated in a Parr apparatus for 5 hr. The catalyst was filtered off and washed with EtOAc. The filtrate was evaporated to dryness and the residue was purified by flash chromatography (silica gel, 30% to 40% EtOAc in hexane containing 0.5% HOAc) to give 0.298 gm of the title compound.

NMR (CDCl13): δ0.91 (t, 3H), 0.95 (t, 3H), 1.08 (t, 3H), 1.30 (m, 2H), 1.41 (t, 3H), 1.7–2.1 (m, 6H), 3.61 (s, 2H), 4.04 (q, 2H), 4.82 (q, 1H), 5.58 (s, 1H), 6.8–7.3 (m, 9H)

EXAMPLE 37

(4S)-3,3-Diethyl-1-[(R)-α-n-propyl-(4-methyl)benzylaminocarbonyl]-4-[(4-carboxymethyl-3-chloro)phenoxy]azetidin-2-one 0.2 gm of material prepared in Example 34 was dissolved in $CH_2Cl_2$ (2 ml) and DMF (3 drops) and oxalyl chloride (0.06 ml) was added. Gas evolution occurred and after 30 min the solution was concentrated to dryness and the residue was diluted with $Et_2O$ (3 ml). To this solution was added an ethereal solution of $CH_2N_2$. After 1 hr the reaction was added to a mixture of $AgNO_3$ (50 mg) and AgO (25 mg) in $H_2O$ (5 ml)/THF (5 ml) at 70° C. After an additional 1 hr, the mixture was filtered through Celite and the fitrate was extracted with EtOAc. The organic layer was washed successively with $H_2O$ and brine and then dried over $Na_2SO_4$, filtered and evaporated to dryness. The residue so obtained was purified by flash chromatography (silica gel, using 30–40% EtOAc 1% acetic acid in hexane as eluant) to give 0.112 gm of the title compound.

NMR (CDCl$_3$): δ 0.90 (t, 3H), 0.94 (t, 3H), 1.06 t, 3H), 1.32 (m, 2H), 1.6–2.1 (m, 6H), 2.32 (s, 3H), 3.76 (s, 2H), 4.85 (q, 1H), 5.55 (s, 1H), 6.93 (d, 1H), 7.1–7.4 (m, 6H), 7.98 (m, 1H)

EXAMPLE 38

(4S)-3,3-Diethyl-1-[(R)-α-n-propyl-(4-methyl)benzylaminocarbonyl]-4-[(4-carboxymethyl-3-fluoro)phenoxy]azetidin-2-one The title compound was prepared essentially as described above for Example 37 except that the material prepared in Example 35 was used as starting material.

NMR (CDCl$_3$): δ 0.91 (t, 3H), 0.94 (t, 3H), 1.06 (t, 3H), 1.30 (m, 2H), 1.6–2.1 (m, 6H), 2.31 (s, 3H), 3.63 (s, 2H), 4.82 (q, 1H), 5.55 (s, 1H), 6.8–7.3 (m, 8H)

EXAMPLE 39

Starting with 3,3-diethyl-4-acetoxyazetidin-2-one as prepared in Example 22, Step B (Scheme (d)) followed by displacement of the acetate with the appropriate phenol and acylation of the nitrogen with the corresponding chiral isocyanate as shown in Scheme (h) and Example 20, Steps C-E, the following compounds were prepared. The diastereomers obtained on acylation were separated by silica gel chromatography using 10–30% ethylacetate/hexane solvent mixtures.

(4S)-3,3-diethyl-1-[(R)-α-ethylbenzylaminocarbonyl]-4-[(4-carboxymethyl)phenoxy]azetidin-2-one.

NMR (CDCl$_3$): δ 0.9 (t,3H,J=7 Hz), 0.94 (t,3H,J=7 Hz), 1.07 (t,3H,J=7 hz) 1.65-2.05 (m,6H), 3.58 (s,2H), 4.8 (q,1H, J=8 Hz), 5.58 (s,1H), 7.0 (d, 1H, J=8 Hz), 7.1–7.45 (m,9H)

(4S)-3,3-diethyl-1-[(R)-α-n-propylbenzylaminocarbonyl]-4-[(4-carboxymethyl)phenoxy]azetidin-2-one.

NMR (CDCl$_3$): δ 0.91 (t, 3H,J=7 Hz), 0.94 (t,3H,J=7 Hz), 1.07 (t,3H,J=7 hz) 1.34 (m,2H), 1.65-2.05 (m,6H), 3.57 (s,2H), 4.88 (q, 1H, J=7 Hz), 5.58 (s,1H), 7.0 (d, 1H, J=7 Hz) 7.1–7.5 (m, 9H)

(4S)-3,3-diethyl-1-[(R)-α-allyl-(4-methyl)benzylaminocarbonyl]-4-[(4-carboxymethyl)phenoxy]azetidin-2-one. NMR (CDCl₃): δ 0.96 (t,3H,J=7 Hz), 1.07 (t,3H,J=7 Hz), 1.7-2.1 (m, 4H), 2.32 (s, 3H), 2.57 (t, 2H, J=7 Hz), 3.58 (s, 2H), 4.95 (q, 1H, J=7 Hz), 5.14 (m, 2H), 5.58 (s, 1H), 5.66 (m, 1H), 7.03 (d, 1H, J=7 Hz), 7.16 (s, 4H), 7.19 (s, 4H).

(4S)-3,3-diethyl-1-[(R)-α-allyl(3,4-methylenedioxy)-benzylaminocarbonyl]-4-[(4-carboxymethyl)phenoxy]-azetidin-2-one. NMR (CDCl₃): δ 0.96 (t,3H,J=7 Hz), 1.05 (t,3H,J=7 Hz), 1.65-2.05 (m, 4H), 2.54 (t, 2H J=6 Hz) 4.87 ((q, 1H, J=7 Hz), 5.05-5.2 (m, 2H), 5.58 (s, 1H), 5.66 (m, 1H), 5.94 (s, 2H), 6.76 (s, 3H), 6.98 41, 1H, J32 7 Hz), 7.2 (m,4H)).

(4S)-3,3-diethyl-1-[(R)-α-n-propyl(3,4-methylenedioxy)-benzylaminocarbonyl]-4-[(4-carboxymethyl)-phenoxy]azetidin-2-one. NMR (CDCl₃): δ 0.9 (t,3H,J=7 Hz), 0.94 (t,3H,J=7 Hz), 1.06 (t, 3H J=7 Hz), 1.3 (m, 2H), 1.65-2.1 (m, 6H), 3.58(s, 2H), 4.76(q, 1H, J=7 hz), 5.58(s, 1H), 5.92 (s,2H), 6.15 (s, 3H), 6.88 (d, 1H, J=7 Hz), 7.2 (m, 4H).

(4S)-3,3-diethyl-1-[(R)-α-n-propyl(4-methyl)benzylaminocarbonyl]-4-[(4-carboxy)phenoxy]azetidin-2-one. NMR (CDCl₃): δ 0.91 (t,3H,J=7 Hz), 0.98 (t,3H,J=7 Hz), 1.07 (t, 3H, J=7 Hz) 1.32 (m, 2H), 1.65-2.1 (m, 6H), 2.33(s, 3H), 4.83(q, 1H, J=7 hz), 5.71(s, 1H), 6.93 (d, 1H, J=7 Hz), 7.16 (s, 4H), 7.25 (d,2H,J=8 Hz), 8.04 (d, 2H, J=8 Hz).

(4S)-3,3-diethyl-1-[(R)-α-n-propyl(4-methyl)-benzylaminocarbonyl]-4-[(4-carboxymethyl)phenoxy]azetidin-2-one. NMR (CDCl₃): δ 0.9 (t,3H,J=7 Hz), 0.93 (t,3H,J=7 Hz), 1.07 (t, 3H, J=7 Hz) 1.28 (m, 2H), 1.7-2.1 (m, 6H), 2.33(s, 2H), 3.6 (s,2H), 4.81 (q, 1H, J=7 hz), 5.56 (s, 1H), 6.93 (d, 1H, J=7 Hz), 7.15 (s, 4H), 7.2 (s, 4H).

(4S)-3,3-diethyl-1-[(R)-α-n-propyl(4-methoxy-3-methyl)-benzylaminocarbonyl]-4-[(4-carboxymethyl)-phenoxy]azetidin-2-one. NMR (CDCL₃):

What is claimed is:

1. A compound of the formula (A)

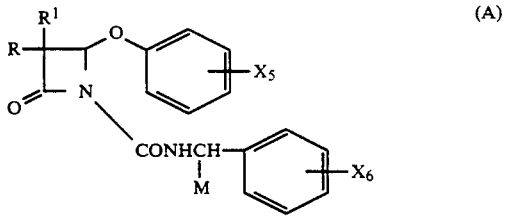

(A)

wherein:
R is $C_{1-6}$ alkyl;
$R^1$ is $C_{1-6}$ alkyl or alkoxy-$C_{1-6}$ alkyl;
M is
   (1) hydrogen,
   (2) $C_{1-6}$ alkyl,
   (3) $C_{2-6}$ alkenyl, or
   (4) $C_{1-6}$ alkoxy-$C_{1-6}$ alkyl;
$X_5$ is
   (1) hydrogen,
   (2) $C_{1-6}$ alkyl,
   (3) halo-$C_{1-6}$ alkyl,
   (4) $C_{2-6}$ alkenyl,
   (5) $C_{2-6}$ alkynyl,
   (6) carboxy,
   (7) carboxy-$C_{1-6}$ alkyl,
   (8) carboxy-$C_{1-6}$ alkylcarbonyl,
   (9) carboxy-$C_{1-6}$ alkylcarbonylamino,
   (10) carboxy-$C_{2-6}$ alkenyl,
   (11) hydroxy-$C_{1-6}$ alkyl,
   (12) $C_{1-6}$ alkylcarbonyl, or
   (13) $C_{1-6}$ alkylcarbonylamino; and
$X_6$ is
   (1) hydrogen,
   (2) $C_{1-6}$ alkyl,
   (3) halo
   (4) carboxy,
   (5) $C_{1-6}$ alkoxy,
   (6) phenyl,
   (7) $C_{1-6}$ alkylcarbonyl,
   (8) di-($C_{1-6}$alkyl)amino,
   (9) phenoxy, or
   (10) methylenedioxy; or
a pharmaceutically acceptable salt thereof.

2. A compound of claim 1 wherein:
$X_5$ is carboxy or carboxy-$C_{1-6}$ alkyl.

3. A compound of claim 2 wherein:
M is $C_{1-3}$ alkyl or allyl; and
$X_6$ is hydrogen, $C_{1-6}$ alkyl, or 3,4-methylenedioxy or phenyl.

4. A compound of claim 3 wherein:
R is ethyl; and
$R^1$ is methyl or ethyl.

5. A compound of claim 4 which is (4S)-3,3-diethyl-1-((R)-α-ethyl-benzyl-aminocarbonyl)-4-(4-carboxymethyl)-phenoxyazetidin-2-one.

6. A compound of claim 4 which is (4S)-3,3-diethyl-1-((R)-α-n-propyl-benzylamino-carbonyl)-4-(4-carboxymethyl)-phenoxyazetidin-2-one.

7. A compound of claim 4 which is (4S)-3,3-diethyl-1-((R)-α-allyl-(4-methyl)benzylaminocarbonyl)-4-(4-carboxymethyl)phenoxyazetidin-2-one.

8. A compound of claim 4 which is (4S)-3,3-diethyl-1-((R)-α-allyl-(3,4-methylenedioxy)-benzylaminocarbonyl)-4-(4-carboxymethyl)-phenoxyazetidin-2-one.

9. A compound of claim 4 which is (4S)-3,3-diethyl-1-((R)-α-n-propyl-(3,4-methylenedioxy)benzylaminocarbonyl)-4-(4-carboxymethyl)phenoxyazetidin-2-one.

10. A compound of claim 4 which is (4S)-3,3-diethyl-1-((R)-α-n-propyl-(4-methyl)-benzylaminocarbonyl)-4-(4-carboxy)phenoxyazetidin-2-one.

11. A compound of claim 4 which is (4S)-3,3-diethyl-1-((R)-α-n-propyl-(4-methyl)-benzylaminocarbonyl)-4-(4-carboxymethyl)-phenoxyazetidin-2-one.

12. A pharmaceutical composition for the inhibition of human leukocyte elastase which comprises a non-toxic therapeutically effective amount of a compound of claim 1 and a pharmaceutically acceptable carrier.

13. A composition of claim 12 wherein:
R is ethyl;
$R^1$ is methyl or ethyl;
M is $C_{1-3}$ alkyl or allyl;
$X_5$ is carboxy or carboxy-$C_{1-6}$ alkyl; and
$X_6$ is hydrogen, $C_{1-6}$ alkyl, 3,4-methylenedioxy or phenyl.

14. A composition of claim 13 wherein the active agent is selected from the group consisiting of:
   (1) (4S)-3,3-diethyl-1-((R)-α-ethylbenzyl-aminocarbonyl)-4-(4-carboxymethyl)-phenoxyazetidin-2-one;
   (2) (4S)-3,3-diethyl-1-((R)-α-n-propylbenzylaminocarbonyl)-4-(4-carboxymethyl)-phenoxyazetidin-2-one;

(3) (4S)-3,3-diethyl-1-((R)-α-allyl-(4-methyl)benzylaminocarbonyl)-4-(4-carboxymethyl)phenoxyazetidin-2-one;
(4) (4S)-3,3-diethyl-1-((R)-α-allyl-(3,4-methylenedioxy)-benzylaminocarbonyl)-4-(4-carboxymethyl)-phenoxyazetidin-2-one;
(5) (4S)-3,3-diethyl-1-((R)-α-n-propyl-(3,4-methylene-dioxy)-benzylaminocarbonyl)-4-(4-carboxymethyl)-phenoxyazetidin-2-one;
(6) (4S)-3,3-diethyl-1-((R)-α-n-propyl-(4-methyl)-benzylaminocarbonyl)-4-(4-carboxy)phenoxyazetidin-2-one; and
(7) (4S)-3,3-diethyl-1-((R)-α-n-propyl-(4-methyl)-benzylaminocarbonyl)-4-(4-carboxymethyl)-phenoxyazetidin-2-one.

15. A method of treatment for the inhibition of human leukocyte elastase which comprises the administration to a subject in need of such inhibition a nontoxic therapeutically effective amount of a compound of claim 1.

16. A method of claim 15 wherein:
R is ethyl;
$R^1$ is methyl or ethyl;
M is $C_{1-3}$ alkyl or allyl;
$X_5$ is carboxy or carboxy-$C_{1-6}$ alkyl; and
$X_6$ is hydrogen, $C_{1-6}$ alkyl, 3,4-methylenedioxy or phenyl.

17. A method of claim 16 wherein the active agent is selected from the group consisting of:
(1) (4S)-3,3-diethyl-1-((R)-α-ethylbenzyl-aminocarbonyl)-4-(4-carboxymethyl)-phenoxyazetidin-2-one;
(2) (4S)-3,3-diethyl-1-((R)-α-n-propylbenzylaminocarbonyl)-4-(4-carboxymethyl)phenoxyazetidin-2-one;
(3) (4S)-3,3-diethyl-1-((R)-α-allyl-(4-methyl)benzylaminocarbonyl)-4-(4-carboxymethyl)phenoxyazetidin-2-one;
(4) (4S)-3,3-diethyl-1((R)-α-allyl-(3,4-methylenedioxy)-benzylaminocarbonyl)-4-(4-carboxymethyl)-phenoxyazetidin-2-one;
(5) (4S)-3,3-diethyl-1-((R)-α-n-propyl-(3,4-methylenedioxy)-benzylaminocarbonyl)-4-(4-carboxymethyl)-phenoxyazetidin-2-one;
(6) (4S)-3,3-diethyl-1-((R)-α-n-propyl-(4-methyl)-benzylaminocarbonyl)-4-(4-carboxy)phenoxyazetidin-2-one; and
(7) (4S)-3,3-diethyl-1-((R)-α-n-propyl-(4-methyl)-benzylaminocarbonyl)-4-(4-carboxymethyl)-phenoxyazetidin-2-one.

* * * * *